United States Patent
Kagabu et al.

(10) Patent No.: US 9,717,242 B2
(45) Date of Patent: Aug. 1, 2017

(54) N-[1-((6-CHLOROPYRIDIN-3-YL)METHYL)PYRIDIN-2(1H)-YLIDENE]-2,2,2-TRIFLUOROACETAMIDE FOR CONTROL OF AGRICULTURAL/HORTICULTURAL PESTS

(71) Applicant: MEIJI SEIKA PHARMA CO., LTD., Chuo-ku, Tokyo (JP)

(72) Inventors: Shinzo Kagabu, Gifu (JP); Masaaki Mitomi, Yokohama (JP); Shigeki Kitsuda, Yokohama (JP); Ryo Horikoshi, Yokohama (JP); Masahiro Nomura, Yokohama (JP); Yasumichi Onozaki, Yokohama (JP)

(73) Assignee: MEIJI SEIKA PHARMA CO., LTD., Chuo-ku, Tokyo (JP)

( * ) Notice: Subject to any disclaimer, the term of this patent is extended or adjusted under 35 U.S.C. 154(b) by 0 days.

(21) Appl. No.: 15/080,971

(22) Filed: Mar. 25, 2016

(65) Prior Publication Data
US 2016/0205933 A1    Jul. 21, 2016

Related U.S. Application Data

(60) Continuation of application No. 14/573,344, filed on Dec. 17, 2014, now Pat. No. 9,328,068, which is a (Continued)

(30) Foreign Application Priority Data

Aug. 31, 2010    (JP) .................. 2010-194584

(51) Int. Cl.

| | | |
|---|---|---|
| *C07D 401/06* | (2006.01) | |
| *A61K 31/444* | (2006.01) | |
| *A01N 43/40* | (2006.01) | |
| *C07D 211/98* | (2006.01) | |
| *A01N 43/50* | (2006.01) | |
| *A01N 43/78* | (2006.01) | |
| *A01N 47/40* | (2006.01) | |
| *C07C 233/05* | (2006.01) | |
| *C07C 233/12* | (2006.01) | |
| *C07C 261/04* | (2006.01) | |
| *C07C 271/12* | (2006.01) | |
| *C07C 311/09* | (2006.01) | |
| *C07F 9/58* | (2006.01) | |
| *A01N 37/18* | (2006.01) | |
| *A01N 43/54* | (2006.01) | |
| *A01N 43/58* | (2006.01) | |

(Continued)

(52) U.S. Cl.
CPC ............ *A01N 43/40* (2013.01); *A01N 37/18* (2013.01); *A01N 43/50* (2013.01); *A01N 43/54* (2013.01); *A01N 43/58* (2013.01); *A01N 43/78* (2013.01); *A01N 47/02* (2013.01); *A01N 47/12* (2013.01); *A01N 47/40* (2013.01); *A01N 57/32* (2013.01); *C07C 233/05* (2013.01); *C07C 233/12* (2013.01); *C07C 261/04* (2013.01); *C07C 271/12* (2013.01); *C07C 311/09* (2013.01); *C07D 211/98* (2013.01); *C07D 213/36* (2013.01); *C07D 213/40* (2013.01); *C07D 213/42* (2013.01); *C07D 213/61* (2013.01); *C07D 213/75* (2013.01); *C07D 237/08* (2013.01); *C07D 277/32* (2013.01); *C07D 333/20* (2013.01); *C07D 401/06* (2013.01); *C07D 401/12* (2013.01); *C07D 405/12* (2013.01); *C07D 417/12* (2013.01); *C07F 9/582* (2013.01); *C07F 9/588* (2013.01)

(58) Field of Classification Search
None
See application file for complete search history.

(56) References Cited

U.S. PATENT DOCUMENTS

| | | |
|---|---|---|
| 3,867,447 A | 2/1975 | Cherkofsky |
| 4,206,141 A | 6/1980 | Mihailovski |

(Continued)

FOREIGN PATENT DOCUMENTS

| | | |
|---|---|---|
| DE | 2342331 | 3/1974 |
| EP | 0268915 A * | 9/1987 |

(Continued)

OTHER PUBLICATIONS

Braun et al., "Haftestigkeit organischer Reste", Berichte der Deutschen Chemischen Gesellschaft, 70B(6):1241-1249, Abstract No. XP055147650, 70B:1241-1249 (1937), Communication for EP 11821689.4.

(Continued)

*Primary Examiner* — Noble Jarrell
*Assistant Examiner* — Ben S Michelson
(74) *Attorney, Agent, or Firm* — Sughrue Mion, PLLC

(57) ABSTRACT

A compound of formula (Ie'):

wherein Ar', $R_1$, $R_{4e}$ and Y are as defined herein and a method of controlling pests using the compound.

1 Claim, 8 Drawing Sheets

Related U.S. Application Data division of application No. 13/814,753, filed as application No. PCT/JP2011/069352 on Aug. 26, 2011, now Pat. No. 8,957,214.

(51) Int. Cl.

| | | |
|---|---|---|
| *A01N 47/02* | (2006.01) | |
| *A01N 47/12* | (2006.01) | |
| *A01N 57/32* | (2006.01) | |
| *C07D 213/36* | (2006.01) | |
| *C07D 213/40* | (2006.01) | |
| *C07D 213/42* | (2006.01) | |
| *C07D 213/61* | (2006.01) | |
| *C07D 213/75* | (2006.01) | |
| *C07D 237/08* | (2006.01) | |
| *C07D 277/32* | (2006.01) | |
| *C07D 333/20* | (2006.01) | |
| *C07D 401/12* | (2006.01) | |
| *C07D 405/12* | (2006.01) | |
| *C07D 417/12* | (2006.01) | |

(56) References Cited

U.S. PATENT DOCUMENTS

| | | | |
|---|---|---|---|
| 4,803,277 A | | 2/1989 | Shiokawa et al. |
| 5,250,498 A | * | 10/1993 | Andree .......... A01N 43/40 504/105 |
| 6,335,357 B1 | | 1/2002 | Okui et al. |
| 8,957,214 B2 | * | 2/2015 | Kagabu .......... C07D 211/98 546/265 |
| 9,328,068 B2 | * | 5/2016 | Kagabu .......... C07D 213/61 |
| 2007/0135497 A1 | | 6/2007 | Mitani et al. |
| 2009/0156643 A1 | | 6/2009 | Mita et al. |
| 2010/0160326 A1 | | 6/2010 | Kimura et al. |

FOREIGN PATENT DOCUMENTS

| | | | |
|---|---|---|---|
| EP | 259738 | | 3/1988 |
| EP | 0268915 | | 6/1988 |
| EP | 432600 | | 6/1991 |
| EP | 0976737 | | 2/2000 |
| EP | 1997813 | | 12/2008 |
| EP | 2030971 | | 4/2009 |
| GB | 1285390 | | 8/1972 |
| JP | 4985025 | | 8/1974 |
| JP | 63227552 | | 9/1988 |
| JP | 3190859 | | 8/1991 |
| JP | 578323 | | 3/1993 |
| JP | 5078323 | | 3/1993 |
| JP | 5078323 A | * | 3/1993 |
| JP | 2859301 | | 2/1999 |
| JP | 2002520384 | | 7/2002 |
| JP | 200326661 | | 1/2003 |
| JP | 2004524287 | | 8/2004 |
| JP | 2005225860 | | 8/2005 |
| JP | 2008260691 | | 10/2008 |
| JP | 2010138082 | | 6/2010 |
| WO | 9726243 | | 7/1997 |
| WO | 0003975 | | 1/2000 |
| WO | 0250035 | | 6/2002 |
| WO | 2005044007 | | 5/2005 |
| WO | 2005105748 | | 11/2005 |
| WO | 2006024411 | | 3/2006 |
| WO | 2006138147 | | 12/2006 |
| WO | WO 2006138147 A1 | * | 12/2006 |
| WO | 2007105814 | | 9/2007 |
| WO | 2009097992 | | 8/2009 |

OTHER PUBLICATIONS

Braun et al., "Haftestigkeit organischer Reste", Justus Liegigs Annalen der Chemie, 449:249-277, Abstract No. XP055147645 (1926), Communication for EP 11821689.4.

Caira et al., "Cyrstalline polymorphism of organic compounds", Topics in Current Chemistry, 198:163-208 (1998).

Chemische Berichte, 88:1103-1108 (1955).

Communication for EP 11821689 dated Nov. 28, 2013, with Supplementary European Search Report (dated Nov. 19, 2013).

Communication for EP Application No. 13157997 with European Search Report dated Oct. 1, 2013.

Communication for European Patent Application No. 11 821 689.4 dated Oct. 30, 2014.

Communication for European Patent No. 11 821 689.4, dated Oct. 30, 2014.

Database Accession No. 1247358-37-7, Dababase Registry, Chemical Abstract (Oct. 10, 2007).

Hendrickson et al., "Triflamides for Protection and Monoalkylation of Amines and a New Gabriel Synthesis" Tetrahedron Letters, 39:3839-3842 (1973).

Brunet, "In vivo metabolic fate of [14C]-acetamiprid in six biological compartments of the honeybee, Apis mellifera L", Pest Management Science, 61(8):742-748 (2005).

Matsumura et al., "Species-specific insecticide resistance to imidacloprid and fipronil in the rice planthoppers Nilaparvata lugens and Sogatella furcifera in East and South-east Asia", Pest Management Science, 64(11):1115-1121 (2008).

Schippers et al., "Journal of Photochemistry and Photobiology B: Biology", Journal of Photochemistry and Photobiology B: Biology, 98(1):57-60 (2010).

Shibuya Index, 14th Edition, p. 208 (2009).

Dai, "Metabolism of the Neonicotinoid Insecticides Acetamiprid and Thiacloprid by the Yeast Rhodotorula mucilaginosa Strain IM-2", Journal of Agricultural and Food Chemistry, 58(4):2419-2425 (2010).

\* cited by examiner

N-[1-((6-CHLOROPYRIDIN-3-YL)METHYL) PYRIDIN-2(1H)-YLIDENE]-2,2,2-TRIFLUOROACETAMIDE FOR CONTROL OF AGRICULTURAL/HORTICULTURAL PESTS

CROSS-REFERENCE TO RELATED APPLICATIONS

This application is Continuation of U.S. application Ser. No. 14/573,344, filed Dec. 17, 2014 (now allowed); which is a Divisional of U.S. application Ser. No. 13/814,753, filed Feb. 7, 2013 (now U.S. Pat. No. 8,957,214); which is a National Stage Entry under 35 U.S.C. 371 of International Application No. PCT/JP2011/069352, filed on Aug. 26, 2011; which claims priority to Japanese Patent Application No. 2010-194584, filed on Aug. 31, 2010; the contents of all of which are incorporated herein by reference in their entireties.

TECHNICAL FIELD

The present invention relates to novel amine derivatives and pest control agents which use the same.

BACKGROUND ART

Many pest control agents have been discovered to date. However, still novel pesticides are desired today owing to, for example, the resistant problem to pesticides and to concerns such as the persistence of the pesticide effects and safety at the time of use.

In paddy rice cultivation in East Asia and Southeast Asia in particular, as indicated in Non-Patent Document 1, damage by planthoppers which have developed chemical resistance to major insecticides, including neonicotinoids such as imidacloprid and phenylpyrazole pesticides such as fipronil has emerged. As a result, specific agents for planthoppers that have developed resistance are awaited.

With regard to heterocycle-containing amine derivatives, Patent Document 1 describes monoalkylamine compounds having a cyano group on the nitrogen atom, and the insecticidal activity of such compounds on aphids. However, no specific disclosure is made concerning dialkylamine compounds, nor is anything mentioned about the control activity on pests other than aphids.

Patent Document 2 mentions amine derivatives which contain a 2,6-dichloro-4-pyridyl group and have a carboxyl group on the nitrogen atom, as well as the fungicidal activities and insecticidal activities thereof, but discloses no other heterocycles.

In Non-Patent Documents 2 and 3, amine derivatives which contain a 6-chloro-3-pyridyl group and have an acetyl group on the nitrogen atom are disclosed as metabolites or reaction intermediates, but no mention is made of their pest control activities. Non-Patent Document 4 discloses amine derivatives which contain a 6-chloro-3-pyridyl group and have on the nitrogen atom a N-methylcarbamoyl group or a N-formylcarbamoyl group, but makes no mention of the pest control activities thereof.

Patent Document 3 discloses a plurality of compounds having ring structures similar to those of compounds of formula (Ie), but these are intended for use as herbicides; no mention is made of pest control.

Patent Document 4 discloses the structural formula of N-[1-((6-chloropyridin-3-yl)methyl)pyridin-2(1H)-ylidene]-2,2,2-trifluoroacetamide (Table 1, Compound No. 3 in Patent Document 4), but discloses nothing whatsoever concerning the method of preparation. Nor is this compound included in the lists of compounds for which pest control activities were observed (Tables 2 and 3 in Patent Document 4).

Patent Document 5 discloses the structural formula of N-[1-((6-chloropyridin-3-yl)methyl)pyridin-2(1H)-ylidene]-2,2,2-trifluoroacetamide (Table 7, Example No. 12 in Patent Document 5), but discloses nothing whatsoever concerning the method of preparation. Nor is this compound mentioned in the examples of compounds having pest control activities which are described in the working examples.

Non-Patent Document 5 discloses a plurality of compounds having ring structures similar to the compounds of subsequently mentioned formula (Ie), but these are merely disclosed as synthesis intermediates.

Patent Document 6 discloses a plurality of compounds having rings structures similar to the compounds of formula (Ie), but no mention or suggestion is made concerning compounds having a trifluoroacetic acid imino structure.

CITATION LIST

Patent Literatures

[PL 1] Japanese Unexamined Patent Application Publication No. 2003-26661 (JP 2003-26661 A)
[PL 2] International Publication No. WO 2002/050035 (WO 2002-050035)
[PL 3] European Unexamined Patent Application Publication No. 432600
[PL 4] Japanese Unexamined Patent Application Publication No. Hei 5-78323 (JP 5-78323 A)
[PL 5] European Unexamined Patent Application Publication No. 268915
[PL 6] European Unexamined Patent Application Publication No. 259738

Non Patent Literatures

[NPL 1] Pest Management Science, 64(11), 1115-1121 (2008)
[NPL 2] Journal of Agricultural and Food Chemistry, 58(4), 2419 (2010)
[NPL 3] Pest Management Science, 61(8), 742 (2005)
[NPL 4] Journal of Photochemistry and Photobiology B: Biology, 98(1), 57 (2010)
[NPL 5] Chemische Berichte, 88, 1103-8 (1955)

SUMMARY OF INVENTION

Technical Problem

It is therefore an object of the present invention to provide novel pest control agents and thereby, in the pest control field, to solve the problems of existing pesticides, such as resistance to the pesticides, persistence of the pesticide effects, and safety at the time of use.

One major object of the invention is to provide pesticides which have excellent control effects against the brown rice planthopper, the white-backed rice planthopper and the small brown planthopper, all major insect pests today in the field of paddy rice cultivation, which have a high activity even against pesticide-resistant planthoppers, and which reduce the chances for the exposure of workers to the pesticide during use in, for example, soil treatment, seed treatment and seedling box treatment and can thus be safely employed.

Solution to Problem

The inventors have conducted extensive investigations in order to solve the above problems, as a result of which they have discovered that amine derivatives of chemical formula (I) have excellent activities as pest control agents.

Accordingly, the invention provides:

(1) A pest control agent comprising at least one compound of the following formula (I) or a salt thereof

[Chem. 1]

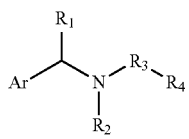

(I)

(wherein Ar is a phenyl group which may be substituted or a 5- or 6-membered heterocycle which may be substituted;

$R_1$ is a hydrogen atom or a $C_{1-6}$ alkyl group;

$R_2$ is a $C_{1-6}$ alkylcarbonyl group in which the alkyl moiety may be substituted with a halogen atom, a $C_{1-6}$ alkyloxycarbonyl group in which the alkyl moiety may be substituted with a halogen atom, a $C_{1-6}$ alkylsulfonyl group in which the alkyl moiety may be substituted with a halogen atom, $CONR_6R_7$, a $C_{1-6}$ O,O'-alkylphosphoryl group in which the alkyl moiety may be substituted with a halogen atom, a cyano group, a formyl group or a nitro group;

$R_3$ is a $C_{1-8}$ alkylene group which may be substituted with a halogen atom, a $C_{2-8}$ alkenylene group which may be substituted with a halogen atom, a $C_{2-8}$ alkynylene group which may be substituted with a halogen atom, a phenylene group which may be substituted, or a 5- or 6-membered heterocyclic divalent group which may be substituted; and $R_4$ is a hydrogen atom, a cyano group, a phenyl group which may be substituted, a 3- to 8-membered cyclic alkyl group which may be substituted, a 3- to 8-membered heterocyclic which may be substituted, a halogen atom, $OR_5$, $OCOR_5$, $OCOOR_5$, $COR_5$, $COOR_5$, $SR_5$, $SOR_5$, $SO_2R_5$, N—CO—$OR_8$, N—CO—$SR_8$, N—CS—$OR_8$, N—CS—$SR_8$, N—O—CO—$R_8$, O—CO—$R_8$, O—CO—$OR_B$, O—CO—$SR_8$, O—CS—$OR_B$, O—CS—$SR_8$, S—CS—$OR_8$, S—CS—$SR_8$, S—CO—$OR_8$, S—CO—$SR_8$, S—CS—$R_8$, $NR_9R_{10}$, O—CO—$NR_9R_{10}$, O—CS—$NR_9R_{10}$, S—CO—$NR_9R_{10}$ or S—CS—$NR_9R_{10}$;

wherein $R_5$ is a $C_{1-6}$ alkyl group which may be substituted with a halogen atom, an aryl group which may be substituted with a halogen atom or an aralkyl group which may be substituted with a halogen atom;

$R_6$ and $R_7$ are each independently a hydrogen atom or a $C_{1-6}$ alkyl group which may be substituted with a halogen atom;

$R_8$ is a $C_{1-6}$ alkyl group which may be substituted, the substituent being a halogen atom, a $C_{1-4}$ alkyloxycarbonyl group, a $C_{1-4}$ alkylcarbonyl group, a benzoyl group which may be substituted with a halogen atom or a $C_{1-4}$ alkyl group which may be substituted with a halogen atom, a $C_{1-4}$ alkyloxy group or a $C_{1-4}$ alkylthio group;

$R_9$ and $R_{10}$ are each independently a hydrogen atom, a formyl group, a $C_{1-6}$ alkyl group which may be substituted with a halogen atom, a $C_{1-6}$ alkylcarbonyl group in which the alkyl moiety may be substituted with a halogen atom, a $C_{1-6}$ alkylcarbonyloxy group in which the alkyl moiety may be substituted with a halogen atom, a phenyl group which may be substituted (the substituent being a halogen atom, a $C_{1-4}$ alkyl group which may be substituted with a halogen atom, or a $C_{1-4}$ alkyloxy group which may be substituted with a halogen atom), or a benzyl group which may be substituted (the substituent being a halogen, a $C_{1-4}$ alkyl group which may be substituted with a halogen or a $C_{1-4}$ alkyloxy group which may be substituted with a halogen), $R^9$ and $R^{10}$ together form a ring and denote a 3- to 10-membered heterocycloalkyl group containing at least one nitrogen atom, or N, $R_9$ and $R_{10}$ together form a ring and denote a 5- or 6-membered aromatic heterocycle containing at least one nitrogen atom, and N, $R_2$, $R_3$ and $R_4$ may together form a group of formula (E)

[Chem. 2]

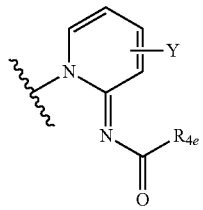

(E)

wherein Y is a hydrogen atom, a halogen atom, a hydroxyl group, a $C_{1-6}$ alkyl group which may be substituted with a halogen atom, a $C_{1-6}$ alkyloxy group which may be substituted with a halogen atom, a cyano group, a formyl group or a nitro group, and $R_{4e}$ is a $C_{1-6}$ alkyl group substituted with a halogen or a $C_{1-6}$ alkyloxy group which may be substituted with a halogen;

with the proviso that if Ar is a 2,6-dichloro-4-pyridyl group, then $R_2$ is not a $C_{1-6}$ alkyloxycarbonyl group in which the alkyl moiety may be substituted with a halogen atom).

(2) The pest control agent according to (1), wherein Ar in formula (I) is a 6-chloro-3-pyridyl group or a 5-chloro-3-thiazolyl group.

(3) The pest control agent according to (1) or (2), wherein $R_2$ in formula (I) is a $C_{1-6}$ alkylcarbonyl group in which the alkyl moiety may be substituted with a halogen atom, a $C_{1-6}$ alkylsulfonyl group in which the alkyl moiety may be substituted with a halogen atom, or a cyano group.

(4) The pest control agent according to (1), wherein the compound of formula (I) is a compound of formula (Ie) below.

[Chem. 3]

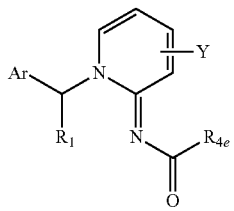

(Ie)

(5) The pest control agent according to (4), wherein $R_{4e}$ in formula (Ie) is a $C_{1-6}$ alkyl group substituted with a halogen atom.

(6) The pest control agent according to (4), wherein Y in formula (Ie) is a hydrogen atom or a halogen atom.

(7) The pest control agent according to (4), wherein $R_{4e}$ in formula (Ie) is a $C_{1-6}$ alkyl group substituted with a halogen atom, and Y is a hydrogen atom or a halogen atom.

(8) The pest control agent according to (4), wherein the compound of formula (Ie) is a compound selected from the group consisting of N-[1-((6-chloropyridin-3-yl)methyl)pyridin-2(1H)-ylidene]-2,2,2-trifluoroacetamide, N-[1-((6-chloro-5-fluoropyridin-3-yl)methyl)pyridin-2(1H)-ylidine]-2,2,2-trifluoroacetamide, N-[1-((6-fluoropyridin-3-yl)methyl)pyridin-2(1H)-ylidene]-2,2,2-trifluoroacetamide, N-[1-((6-bromopyridin-3-yl)methyl)pyridin-2(1H)-ylidene]-2,2,2-trifluoroacetamide, N-[1-(1-(6-chloropyridin-3-yl)ethyl)pyridin-2(1H)-ylidene]-2,2,2-trifluoroacetamide, N-[1-((6-chloropyridin-3-yl)methyl)pyridin-2(1H)-ylidene]-2,2-difluoroacetamide, 2-chloro-N-[1-((6-chloropyridin-3-yl)methyl)pyridin-2(1H)-ylidene]-2,2-difluoroacetamide, N-[1-((2-chloropyrimidin-5-yl)methyl)pyridin-2(1H)-ylidene]-2,2,2-trifluoroacetamide and N-[1-((6-chloropyridin-3-yl)methyl)pyridin-2(1H)-ylidene]-2,2,3,3,3-pentafluoropropanamide.

(9) The pest control agent according to any one of (1) to (8), which has a pest control activity on at least one type of pest selected from the group consisting of lepidopterous pests, hemipterous pests, thysanopterous pests, dipterous pests, coleopterous pests, animal parasitic fleas and ticks, and canine heartworms.

(10) The pest control agent according to any one of (1) to (9), wherein the pest is an agricultural/horticultural pest or an animal parasitic pest.

(11) The pest control agent according to any one of (1) to (9), wherein the pest is a pesticide-resistant pest.

(12) An amine derivative of the following formula (I) or a salt thereof

[Chem. 4]

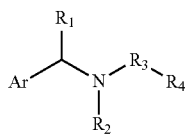

(I)

(wherein Ar is a phenyl group which may be substituted or a 5- or 6-membered heterocycle which may be substituted;

$R_1$ is a hydrogen atom or a $C_{1-6}$ alkyl group;

$R_2$ is a $C_{1-6}$ alkylcarbonyl group in which the alkyl moiety may be substituted with a halogen atom, a $C_{1-6}$ alkyloxycarbonyl group in which the alkyl moiety may be substituted with a halogen atom, a $C_{1-6}$ alkylsulfonyl group in which the alkyl moiety may be substituted with a halogen atom, $CONR_6R_7$, a $C_{1-6}$ O,O'-alkylphosphoryl group in which the alkyl moiety may be substituted with a halogen atom, a cyano group, a formyl group or a nitro group;

$R_3$ is a $C_{1-8}$ alkylene group which may be substituted with a halogen atom, a $C_{2-8}$ alkenylene group which may be substituted with a halogen atom, a $C_{2-8}$ alkynylene group which may be substituted with a halogen atom, a phenylene group which may be substituted, or a 5- or 6-membered heterocyclic divalent group which may be substituted; and $R_4$ is a hydrogen atom, a cyano group, a phenyl group which may be substituted, a 3- to 8-membered cyclic alkyl group which may be substituted, a 3- to 8-membered heterocyclic which may be substituted, a halogen atom, $OR_5$, $OCOR_5$, $OCOOR_5$, $COR_5$, $COOR_5$, $SR_5$, $SOR_5$, $SO_2R_5$, N—CO—$OR_8$, N—CO—$SR_8$, N—CS—$OR_8$, N—CS—$SR_8$, N—O—CO—$R_8$, O—CO—$R_8$, O—CO—$OR_8$, O—CO—$SR_8$, O—CS—$OR_8$, O—CS—$SR_8$, S—CS—$OR_8$, S—CS—$SR_8$, S—CO—$OR_8$, S—CO—$SR_8$, S—CS—$R_8$, $NR_9R_{10}$, O—CO—$NR_9R_{10}$, O—CS—$NR_9R_{10}$, S—CO—$NR_9R_{10}$ or S—CS—$NR_9R_{10}$;

wherein $R_5$ is a $C_{1-6}$ alkyl group which may be substituted with a halogen atom, an aryl group which may be substituted with a halogen atom or an aralkyl group which may be substituted with a halogen atom;

$R_6$ and $R_7$ are each independently a hydrogen atom or a $C_{1-6}$ alkyl group which may be substituted with a halogen atom;

$R_8$ is a $C_{1-6}$ alkyl group which may be substituted, the substituent being a halogen atom, a $C_{1-4}$ alkyloxycarbonyl group, a $C_{1-4}$ alkylcarbonyl group, a benzoyl group which may be substituted with a halogen atom or a $C_{1-4}$ alkyl group which may be substituted with a halogen atom, a $C_{1-4}$ alkyloxy group or a $C_{1-4}$ alkylthio group;

$R_9$ and $R_{10}$ are each independently a hydrogen atom, a formyl group, a $C_{1-6}$ alkyl group which may be substituted with a halogen atom, a $C_{1-6}$ alkylcarbonyl group in which the alkyl moiety may be substituted with a halogen atom, a $C_{1-6}$ alkylcarbonyloxy group in which the alkyl moiety may be substituted with a halogen atom, a phenyl group which may be substituted (the substituent being a halogen atom, a $C_{1-4}$ alkyl group which may be substituted with a halogen atom, or a $C_{1-4}$ alkyloxy group which may be substituted with a halogen atom), or a benzyl group which may be substituted (the substituent being a halogen, a $C_{1-4}$ alkyl group which may be substituted with a halogen or a $C_{1-4}$ alkyloxy group which may be substituted with a halogen), $R^9$ and $R^{10}$ together form a ring and denote a 3- to 10-membered heterocycloalkyl group containing at least one nitrogen atom, or N, $R_9$ and $R_{10}$ together form a ring and denote a 5- or 6-membered aromatic heterocycle containing at least one nitrogen atom; and if Ar is a pyridyl group which may be substituted or a pyrimidyl group which may be substituted, N, $R_2$, $R_3$ and $R_4$ may together form a group of formula (E)

[Chem. 5]

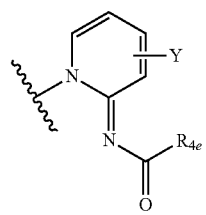

(E)

wherein Y is a hydrogen atom, a halogen atom, a hydroxyl group, a $C_{1-6}$ alkyl group which may be substituted with a halogen atom, a $C_{1-6}$ alkyloxy group which may be substituted with a halogen atom, a cyano group, a formyl group or a nitro group, and $R_{4e}$ is a $C_{1-6}$ alkyl group substituted with a halogen or a $C_{1-6}$ alkyloxy group which may be substituted with a halogen;

with the proviso that if Ar is a 2,6-dichloro-4-pyridyl group, then $R_2$ is not a $C_{1-6}$ alkyloxycarbonyl group in which the alkyl moiety may be substituted with a halogen atom, and if Ar is a 6-chloro-3-pyridyl group, then $R_1$ is not a hydrogen atom, Y is not a 5-methyl group and $R_{4e}$ is not a $CF_3$ group).

(13) The amine derivative or a salt thereof according to (12), wherein Ar in formula (I) is a 6-chloro-3-pyridyl group or a 5-chloro-3-thiazolyl group.

(14) The amine derivative or a salt thereof according to (12) or (13), wherein $R_2$ in formula (I) is a $C_{1-6}$ alkylcarbonyl group in which the alkyl moiety may be substituted with a halogen atom, a $C_{1-6}$ alkylsulfonyl group in which the alkyl moiety may be substituted with a halogen atom, or a cyano group.

(15) The amine derivative or a salt thereof according to (12), wherein the compound of formula (I) is a compound of formula (Ie') below.

[Chem. 6]

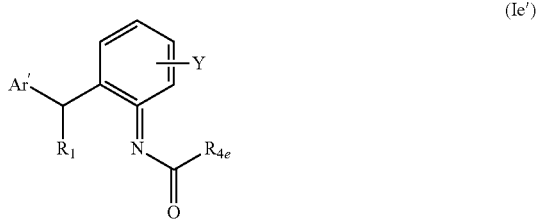

(Ie')

(wherein Ar' is a pyridyl group which may be substituted or a pyrimidyl group which may be substituted; Y is a hydrogen atom, a halogen atom, a hydroxyl group, a $C_{1-6}$ alkyl group which may be substituted with a halogen atom, a $C_{1-6}$ alkyloxy group which may be substituted with a halogen atom, a cyano group, a formyl group or a nitro group; and $R_{4e}$ is a $C_{1-6}$ alkyl group substituted with a halogen or a $C_{1-6}$ alkyloxy group which may be substituted with a halogen;
with the proviso that if Ar' is a 6-chloro-3-pyridyl group, then $R_1$ is not a hydrogen atom, Y is not a 5-methyl group and $R_{4e}$ is not a trifluoromethyl group).

(16) The amine derivative or a salt thereof according to (15), wherein $R_{4e}$ in formula (Ie') is a $C_{1-6}$ alkyl group substituted with a halogen atom.

(17) The amine derivative or a salt thereof according to (15), wherein Y in formula (Ie') is a hydrogen atom or a halogen atom.

(18) The amine derivative or a salt thereof according to (15), wherein $R_{4e}$ in formula (Ie') is a $C_{1-6}$ alkyl group substituted with a halogen atom and Y is a hydrogen atom or a halogen atom.

(19) The amine derivative or a salt thereof according to (15), wherein the compound of formula (Ie') is a compound selected from the group consisting of N-[1-((6-chloropyridin-3-yl)methyl)pyridin-2(1H)-ylidene]-2,2,2-trifluoroacetamide, N-[1-((6-chloro-5-fluoropyridin-3-yl)methyl)pyridin-2(1H)-ylidine]-2,2,2-trifluoroacetamide, N-[1-((6-fluoropyridin-3-yl)methyl)pyridin-2(1H)-ylidene]-2,2,2-trifluoroacetamide, N-[1-((6-bromopyridin-3-yl)methyl)pyridin-2(1H)-ylidene]-2,2,2-trifluoroacetamide, N-[1-(1-(6-chloropyridin-3-yl)ethyl)pyridin-2(1H)-ylidene]-2,2,2-trifluoroacetamide, N-[1-((6-chloropyridin-3-yl)methyl)pyridin-2(1H)-ylidene]-2,2-difluoroacetamide, 2-chloro-N-[1-((6-chloropyridin-3-yl)methyl)pyridin-2(1H)-ylidene]-2,2-difluoroacetamide, N-[1-((2-chloropyrimidin-5-yl)methyl)pyridin-2(1H)-ylidene]-2,2,2-trifluoroacetamide and N-[1-((6-chloropyridin-3-yl)methyl)pyridin-2(1H)-ylidene]-2,2,3,3,3-pentafluoropropanamide.

(20) The amine derivative or a salt thereof according to any one of (12) to (19), which has a pest control activity on at least one type of pest selected from the group consisting of lepidopterous pests, hemipterous pests, thysanopterous pests, dipterous pests, coleopterous pests, animal parasitic fleas and ticks, and canine heartworms.

(21) A method for controlling pests, comprising the step of using the pest control agent according to any one of (1) to (9) or the amine derivative or a salt thereof according to any one of (12) to (20).

(22) A method for controlling agricultural/horticultural pests, comprising the step of treating plant seeds, roots, tubers, bulbs, rhizomes, soil, a nutrient solution in hydroponics, a solid culture medium in hydroponics, or a carrier for growing plants, with the pest control agent according to any one of (1) to (9) or the amine derivative or a salt thereof according to any one of (12) to (20), thereby inducing the compound to penetrate and translocate into the plants.

(23) The method according to (21), wherein the pest is an agricultural/horticultural pest or an animal parasitic pest.

(24) The method according to (21), wherein the pest is a pesticide-resistant pest.

Advantageous Effects of Invention

By using the amine derivatives of the invention, it is possible to effectively carry out the control of the diamondback moth, the common cutworm, aphids, delphacid planthoppers, thrips and many other pests.

DESCRIPTION OF EMBODIMENTS

Figure 1:
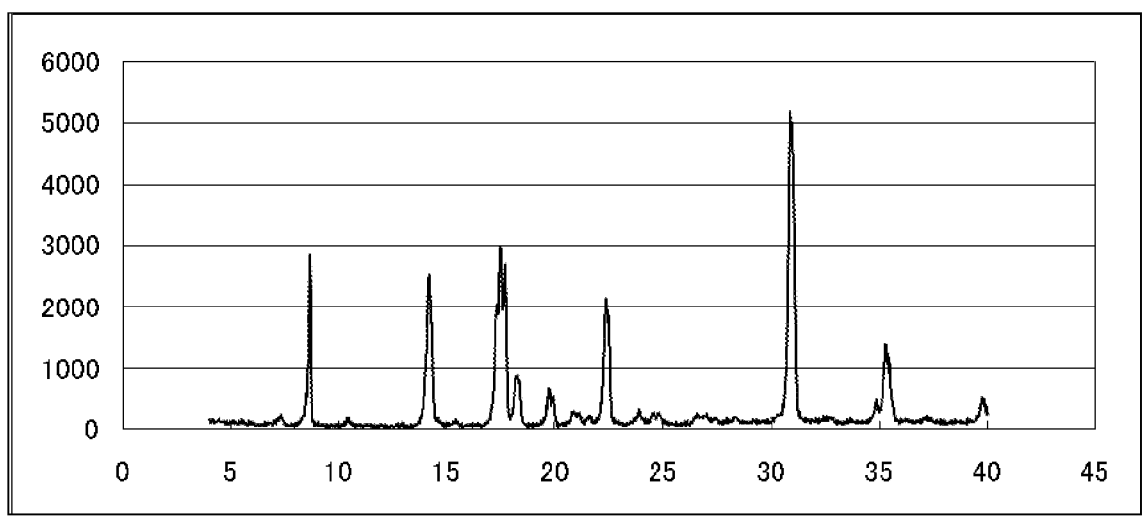
FIG. 1 is a graph showing the results of powder x-ray diffraction analysis on the crystals of N-[1-((6-chloropyridin-3-yl)methyl)pyridin-2(1H)-ylidene]-2,2,2-trifluoroacetamide prepared by a first preparation method.

In the amine derivatives of chemical formula (I) which serve as the active ingredients of the pest control agents provided by the invention, Ar is a phenyl group which may be substituted or a 5- or 6-membered heterocycle which may be substituted, and is preferably a 5- or 6-membered heterocycle which may be substituted.

Exemplary substituents include halogen atoms, $C_{1-4}$ alkyl groups which may be substituted with halogen atoms, alkyloxy groups which may be substituted with halogen atoms, hydroxyl groups, cyano groups and nitro groups. Halogen atoms and $C_{1-4}$ alkyl groups which may be substituted with halogen atoms are preferred.

Illustrative examples of phenyl groups which may be substituted include a phenyl group, a 3-chlorophenyl group, a 4-chlorophenyl group, a 3-cyanophenyl group, a 4-cyanophenyl group, a 3-nitrophenyl group, a 4-nitrophenyl group, a 3,5-dichlorophenyl group, a 4-methylphenyl group, a 4-methoxyphenyl group, a 3,5-dibromophenyl group, a 2,4-dibromophenyl group, a 4-fluorophenyl group, a 4-bromophenyl group, a 3-nitro-5-bromophenyl group and a 3,5-bistrifluoromethyphenyl group. A 4-nitrophenyl group, a 4-cyanophenyl group or a 3,5-dibromophenyl group is preferred.

Illustrative examples of 5- or 6-membered heterocycles which may be substituted include pyridine, thiazole, tetrahydrofuran and furan. 3-Pyridyl groups and 3-thiazolyl groups are preferred. A 6-chloro-3-pyridyl group, a 5-chloro-3-thiazolyl group, a 6-chloro-5-fluoro-3-pyridyl group, a 6-bromo-3-pyridyl group, a 6-fluoro-3-pyridyl group, a 5,6-dichloro-3-pyridyl group or a 6-trifluoromethyl-3-pyridyl group is more preferred. A 6-chloro-3-pyridyl group, a 6-fluoro-3-pyridyl group, a 6-chloro-5-fluoro-3-pyridyl group or a 6-bromo-3-pyridyl group is especially preferred.

In chemical formula (I), the "$C_{1-6}$ alkyl group" represented by $R_1$ is an alkyl group having from 1 to 6 carbons that is linear, branched, cyclic or a combination thereof. When a branched or cyclic alkyl group is included, it is apparent that the number of carbons is at least 3. Specific examples include a methyl group, an ethyl group, a propyl group, an isopropyl group and a cyclopropyl group. A methyl group or an ethyl group is preferred.

$R_2$ is a $C_{1-6}$ alkylcarbonyl group in which the alkyl moiety may be substituted with a halogen atom, a $C_{1-6}$ alkyloxycarbonyl group in which the alkyl moiety may be substituted with a halogen atom, a $C_{1-6}$ alkylsulfonyl group in which the alkyl moiety may be substituted with a halogen atom, $CONR_6R_7$, a $C_{1-6}$ O,O'-alkylphosphoryl group in which the alkyl moiety may be substituted with a halogen atom, a cyano group, a formyl group or a nitro group. A $C_{1-6}$ alkylcarbonyl group in which the alkyl moiety may be substituted with a halogen atom, a $C_{1-6}$ alkylsulfonyl group in which the alkyl moiety may be substituted with a halogen atom, or a cyano group is preferred.

$R_3$ is a $C_{1-8}$ alkylene group which may be substituted with a halogen atom, a $C_{2-8}$ alkenylene group which may be substituted with a halogen atom, a $C_{2-8}$ alkynylene group which may be substituted with a halogen atom, a phenylene group which may be substituted, or a 5- or 6-membered heterocyclic divalent group which may be substituted. A $C_{1-8}$ alkylene group which may be substituted with a halogen atom is preferred.

$R_4$ is a hydrogen atom, a cyano group, a phenyl group which may be substituted, a 3- to 8-membered cyclic alkyl group which may be substituted, a 3- to 8-membered heterocyclic which may be substituted, a halogen atom, $OR_5$, $OCOR_5$, $OCOOR_5$, $COR_5$, $COOR_5$, $SR_5$, $SOR_5$, $SO_2R_5$, N—CO—$OR_8$, N—CO—$SR_8$, N—CS—$OR_8$, N—CS—$SR_8$, N—O—CO—$R_8$, O—CO—$R_8$, O—CO—$OR_8$, O—CO—$SR_8$, O—CS—$OR_B$, O—CS—$SR_8$, S—CS—$OR_8$, S—CS—$SR_8$, S—CO—$OR_8$, S—CO—$SR_8$, S—CS—$R_8$, $NR_9R_{10}$, O—CO—$NR_9R_{10}$, O—CS—$NR_9R_{10}$, S—CO—$NR_9R_{10}$ or S—CS—$NR_9R_{10}$.

Here, $R_5$ is a $C_{1-6}$ alkyl group which may be substituted with a halogen atom, an aryl group which may be substituted with a halogen atom or an aralkyl group which may be substituted with a halogen atom.

$R_6$ and $R_7$ are each independently a hydrogen atom or a $C_{1-6}$ alkyl group which may be substituted with a halogen atom.

$R_8$ is a $C_{1-6}$ alkyl group which may be substituted, the substituent being a halogen atom, a $C_{1-4}$ alkyloxycarbonyl group, a $C_{1-4}$ alkylcarbonyl group, a benzoyl group which may be substituted with a halogen atom or a $C_{1-4}$ alkyl group which may be substituted with a halogen atom, a $C_{1-4}$ alkyloxy group or a $C_{1-4}$ alkylthio group.

$R_9$ and $R_{10}$ are each independently a hydrogen atom, a formyl group, a $C_{1-6}$ alkyl group which may be substituted with a halogen atom, a $C_{1-6}$ alkylcarbonyl group in which the alkyl moiety may be substituted with a halogen atom, a $C_{1-6}$ alkylcarbonyloxy group in which the alkyl moiety may be substituted with a halogen atom, a phenyl group which may be substituted (the substituent being a halogen atom, a $C_{1-4}$ alkyl group which may be substituted with a halogen atom, or a $C_{1-4}$ alkyloxy group which may be substituted with a halogen atom), or a benzyl group which may be substituted (the substituent being a halogen, a $C_{1-4}$ alkyl group which may be substituted with a halogen or a $C_{1-4}$ alkyloxy group which may be substituted with a halogen), $R^9$ and $R^{10}$ together form a ring and denote a 3- to 10-membered heterocycloalkyl group containing at least one nitrogen atom, or N, $R_9$ and $R_{10}$ together form a ring and denote a 5- or 6-membered aromatic heterocycle containing at least one nitrogen atom.

The "$C_{1-6}$ alkyl group which may be substituted with a halogen atom" that is represented by $R_5$, $R_6$, $R_7$, $R_8$, $R_9$ and $R_{10}$ is an alkyl group having from 1 to 6 carbons that is linear, branched, cyclic or a combination thereof. The upper limit in the number of halogen atoms which may be substituted is the number of hydrogen atoms on the alkyl group. When a branched or cyclic alkyl group is included, it is apparent that the number of carbons is at least 3.

Illustrative examples of the "$C_{1-6}$ alkyl group which may be substituted with a halogen atom" that is represented by $R_5$ include a methyl group, an ethyl group, an n-propyl group, a difluoromethyl group, a trifluoromethyl group, a chloromethyl group and a 2-trifluoroethyl group.

Illustrative examples of the "$C_{1-6}$ alkyl group which may be substituted with a halogen atom" that is represented by $R_6$ and $R_7$ include a methyl group, an ethyl group, an n-propyl group, a difluoromethyl group, a trifluoromethyl group, a chloromethyl group and a 2-trifluoroethyl group.

Illustrative examples of the "$C_{1-6}$ alkyl group which may be substituted with a halogen atom" that is represented by $R_8$ include a methyl group, an ethyl group, an n-propyl group, an isopropyl group, an n-butyl group, an n-pentyl group, a 2-trifluoroethyl group and a 2-chloroethyl group. A methyl group, an ethyl group, an n-propyl group, an isopropyl group, an n-butyl group or an n-pentyl group is preferred.

Illustrative examples of the "$C_{1-6}$ alkyl group which may be substituted with a halogen atom" that is represented by $R_9$ and $R_{10}$ include a methyl group, an ethyl group, an n-propyl group, an isopropyl group, an n-butyl group, an n-pentyl group, a 2-trifluoroethyl group and a 2-chloroethyl group. A methyl group or an ethyl group is preferred.

The alkyl moiety in the "$C_{1-6}$ alkylcarbonyl group in which the alkyl moiety may be substituted with a halogen atom" that is represented by $R_2$, $R_9$ and $R_{10}$, the "$C_{1-6}$ alkyloxycarbonyl group in which the alkyl moiety may be substituted with a halogen atom," the "$C_{1-6}$ alkylsulfonyl group in which the alkyl moiety may be substituted with a halogen atom" and the "$C_{1-6}$ O,O'-alkylphosphoryl group in which the alkyl moiety may be substituted with a halogen atom" that are represented by $R_2$, and the "$C_{1-6}$ alkylcarbonyloxy group in which the alkyl moiety may be substituted with a halogen atom" that is represented by $R_9$ and $R_{10}$ is an alkyl group having from 1 to 6 carbons that is linear, branched, cyclic or a combination thereof. The upper limit in the number of halogen atoms which may be substituted is the number of hydrogen atoms on the alkyl group. When a branched or cyclic alkyl group is included, it is apparent that the number of carbons is at least 3.

Illustrative examples of the "$C_{1-6}$ alkylcarbonyl group in which the alkyl moiety may be substituted with a halogen atom" that is represented by $R_2$ include an acetyl group, an ethylcarbonyl group, an n-propylcarbonyl group, a difluoroacetyl group, a trifluoroacetyl group, a pentafluoroacetyl group, a chloroacetyl group and a trichloroacetyl group. A trifluoroacetyl group is preferred.

Illustrative examples of the "$C_{1-6}$ alkyloxycarbonyl group in which the alkyl moiety may be substituted with a halogen atom" that is represented by $R_2$ include a methyloxycarbonyl group, an ethyloxycarbonyl group, an n-propyloxycarbonyl group, a chloromethyloxycarbonyl group and a 2-trifluoroethyloxycarbonyl group.

Illustrative examples of the "$C_{1-6}$ alkylsulfonyl group in which the alkyl moiety may be substituted with a halogen atom" that is represented by $R_2$ include a methylsulfonyl group, an ethylsulfonyl group, an n-propylsulfonyl group, a difluoromethylsulfonyl group, a trifluoromethylsulfonyl group, a trichloromethylsulfonyl group and a 2-trifluoromethylsulfonyl group. A trifluoromethylsulfonyl group is preferred.

Illustrative examples of the "$C_{1-6}$ O,O'-alkylphosphoryl group in which the alkyl moiety may be substituted with a halogen atom" that is represented by $R_2$ include an O,O'-dimethylphosphoryl group and an O,O'-diethylphosphoryl group.

Illustrative examples of the "$C_{1-6}$ alkylcarbonyl group in which the alkyl moiety may be substituted with a halogen atom" that is represented by $R_5$ include an acetyl group, an ethylcarbonyl group, an n-propylcarbonyl group, an isopropylcarbonyl group and a 2-chloroethylcarbonyl group.

Illustrative examples of the "$C_{1-6}$ alkylcarbonyl group in which the alkyl moiety may be substituted with a halogen atom" that is represented by $R_9$ and $R_{10}$ include a methyloxycarbonyl group, an ethyloxycarbonyl group, an n-propyloxycarbonyl group, an isopropyloxycarbonyl group and a 2-chloroethyloxycarbonyl group.

Illustrative examples of the "$C_{1-6}$ alkylcarbonyloxy group in which the alkyl moiety may be substituted with a halogen atom" that is represented by $R_9$ and $R_{10}$ include a methylcarbonyloxy group, an ethylcarbonyloxy group, an n-propylcarbonyloxy group, an isopropylcarbonyloxy group and a 2-chloroethylcarbonyloxy group.

The "$C_{1-8}$ alkylene group which may be substituted with a halogen atom" that is represented by $R_3$ is an alkylene group having from 1 to 8 carbons that is linear, branched, cyclic or a combination thereof. The upper limit in the number of halogen atoms which may be substituted is the number of hydrogen atoms on the alkyl group. When a branched or cyclic alkyl group is included, it is apparent that the number of carbons is at least 3. Illustrative examples include a methylene group, an ethylene group, a propylene group, a butylene group, a fluoromethylene group, a 1-chloroethylene group, a 2-methylethylene group, a cyclopropylene group, a 2-cyclopropylethylene group and a 1,3-cyclopentylene group. A methylene group, an ethylene group or a propylene group is preferred. An ethylene group is more preferred.

The "$C_{2-8}$ alkenylene group which may be substituted with a halogen atom" that is represented by $R_3$ is an alkenylene group having from 2 to 8 carbons that is linear, branched, cyclic or a combination thereof. The upper limit in the number of halogen atoms which may be substituted is the number of hydrogen atoms on the alkyl group. When a branched or cyclic alkyl group is included, it is apparent that the number of carbons is at least 3. Illustrative examples include a vinylene group, a 1-propenylene group, a 2-fluoro-1-propenylene group, a 2-methyl-1-propenylene group and a 2-cyclohexen-1,4-ylene group.

The "$C_{2-8}$ alkynylene group which may be substituted with a halogen atom" that is represented by $R_3$ is an alkynylene group having from 2 to 8 carbons that is linear, branched, cyclic or a combination thereof. The upper limit in the number of halogen atoms which may be substituted is the number of hydrogen atoms on the alkyl group. When a branched or cyclic alkyl group is included, it is apparent that the number of carbons is at least 3. Illustrative examples include a propynylene group and a butynylene group. 1-Propynylene is preferred.

The "phenylene which may be substituted" that is represented by $R_3$ is a divalent group from which two of the hydrogen atoms on benzene have been removed, and wherein the substituents are exemplified by halogen atoms, $C_{1-4}$ alkyl groups which may be substituted with a halogen atom, alkyloxy groups which may be substituted with a halogen atom, hydroxyl groups, cyano groups and nitro groups. Illustrative examples include a phenylene group, a 4-fluorophenylene group and a 2-methylphenylene group.

The "5- or 6-membered heterocyclic divalent group which may be substituted" that is represented by $R_3$ is a divalent group from which two of the hydrogen atoms on the 5- or 6-membered heterocycle have been removed, and wherein the substituents are exemplified by halogen atoms, $C_{1-4}$ alkyl groups which may be substituted with a halogen atom, alkyloxy groups which may be substituted with a halogen atom, hydroxyl groups, cyano groups and nitro groups. Illustrative examples include a 2-pyridinylene group.

Substituents which may substituted in the "pyridyl group which may be substituted" or the "pyrimidyl group which may be substituted" that is represented by Ar' in the compound of the formula (Ie') are exemplified by halogen atoms, $C_{1-4}$ alkyl groups which may be substituted with a halogen atom, alkyloxy groups which may be substituted with a halogen atom, hydroxyl groups, cyano groups and nitro groups. Halogen atoms are preferred.

Preferred examples of Ar in the compound of the formula (Ie) and of Ar' in the compound of the formula (Ie') include a 3-pyridyl group, a 6-chloro-3-pyridyl group, a 5-chloro-3-thiazolyl group, a 6-chloro-5-fluoro-3-pyridyl group, a 6-bromo-3-pyridyl group, a 6-fluoro-3-pyridyl group, a 5,6-dichloro-3-pyridyl group, a 6-trifluoromethyl-3-pyridyl group and a 2-chloro-5-pyrimidyl group. A 6-chloro-3-pyridyl group, a 6-fluoro-3-pyridyl group, a 6-chloro-5-fluoro-3-pyridyl group, a 6-bromo-3-pyridyl group or a 2-chloro-5-pyrimidyl group is more preferred.

Y in the compounds of formulas (Ie) and (Ie') represents from 1 to 3 substituents which may be the same or different.

The "$C_{1-6}$ alkyl group which may be substituted with a halogen atom" represented by Y in the compounds of formulas (Ie) and (Ie') is an alkyl group having from 1 to 6 carbons that is linear, branched, cyclic or a combination thereof. The upper limit in the number of halogen atoms which may be substituted is the number of hydrogen atoms on the alkyl group. When a branched or cyclic alkyl group is included, it is apparent that the number of carbons is at least 3.

Illustrative examples include a methyl group, an ethyl group, a n-propyl group, an isopropyl group, a n-butyl group, a t-butyl group, a trifluoromethyl group and a 2-chloroethyl group. A methyl group is preferred.

Illustrative examples of the "$C_{1-6}$ alkyloxy group which may be substituted with a halogen" represented by Y include a methoxy group, an ethoxy group, a trifluomethyl group and a difluoromethyl group.

Preferred examples of Y are a hydrogen atom and halogens. A hydrogen atom is more preferred.

The "$C_{1-6}$ alkyl group substituted with a halogen atom" represented by $R_{4e}$ in the compounds of formulas (Ie) and (Ie') is an alkyl group having from 1 to 6 carbons that is linear, branched, cyclic or a combination thereof. The upper limit in the number of halogen atoms which are substituted is the number of hydrogen atoms on the alkyl group. When a branched or cyclic alkyl group is included, it is apparent that the number of carbons is at least 3.

Illustrative examples include a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group and a difluorocyclopropyl group. A trifluoromethyl group, a trichloromethyl group, a dichloromethyl group, a difluoromethyl group, a difluorochloromethyl group, a chloromethyl group or a pentafluoroethyl group is preferred. A trifluoromethyl group, a difluoromethyl group, a difluorochloromethyl group, a chloromethyl group or a pentafluoroethyl group is more preferred.

Illustrative examples of the "$C_{1-6}$ alkyloxy group which may be substituted with a halogen" represented by $R_{4e}$ include a methoxy group, an ethoxy group, an isopropyloxy group and a trifluoromethoxy group.

Preferred examples of $R_{4e}$ are $C_{1-6}$ alkyl groups which may be substituted with a halogen. A trifluoromethyl group, a difluoromethyl group, a difluorochloromethyl group, a chloromethyl group or a pentafluoroethyl group is more preferred.

Salts of the amine derivatives of chemical formula (I) which act as the active ingredient in the pest control agent provided by the invention are acid addition salts allowable in agricultural and livestock chemicals. Illustrative examples include hydrochlorides, nitrates, sulfates, phosphates and acetates.

In a preferred form of the compound of formula (I),
Ar is a 4-nitrophenyl group, a 4-cyanophenyl group, a 3,5-dibromophenyl group, a 2,4-dibromophenyl group, a 6-chloro-3-pyridyl group, a 5-chloro-3-thiazolyl group, a 6-chloro-5-fluoro-3-pyridyl group, a 6-bromo-3-pyridyl group, a 6-fluoro-3-pyridyl group, a 5,6-dichloro-3-pyridyl group or a 6-trifluoromethyl-3-pyridyl group;
$R_1$ is a hydrogen atom or a methyl group;
$R_2$ is a $C_{1-6}$ alkylcarbonyl group in which the alkyl moiety may be substituted with a halogen atom, a $C_{1-6}$ alkylsulfonyl group in which the alkyl moiety may be substituted with a halogen atom, or a cyano group;
$R_3$ is a methylene group, an ethylene group, a propylene group or a 1-propynylene group; and $R_4$ is a hydrogen atom, a cyano group, $SR_5$ ($R_5$ being a $C_{1-6}$ alkyl group which may be substituted with a halogen), S—CS—$OR_8$ or S—CS—$SR_8$ ($R_8$ being a $C_{1-6}$ alkyl group which may be substituted with a halogen).

Preferred compounds are exemplified by the compounds of
(i) to (iii) below.
(i) Compounds wherein:
Ar is a 4-cyanophenyl group, a 4-nitrophenyl group, a 3,5-dichlorophenyl group, a 3,5-dibromophenyl group, a 2,4-dibromophenyl group, a 4-bromophenyl group, a 3-nitro-5-bromophenyl group, a 6-chloro-3-pyridyl group, a 5-chloro-3-thiazolyl group, a 6-chloro-5-fluoro-3-pyridyl group or a 6-trifluoromethyl-3-pyridyl group;
$R_1$ is a hydrogen atom;
$R_2$ is a trifluoromethylsulfonyl group;
$R_3$ is a methylene group, an ethylene group or a 1-propynylene group; and
$R_4$ is a hydrogen atom or a cyano group.
(ii) Compounds wherein:
Ar is a 6-chloro-3-pyridyl group, a 5-chloro-3-thiazolyl group or a 6-trifluoromethyl-3-pyridyl group;
$R_1$ is a hydrogen atom or a methyl group;
$R_2$ is a cyano group or a trifluoromethylcarbonyl group;
$R_3$ is an ethylene group; and
$R_4$ is a hydrogen atom, $SR_5$ ($R_5$ being a $C_{1-6}$ alkyl group which may be substituted with a halogen), S—CS—$OR_8$ or S—CS—$SR_8$ ($R_8$ being a $C_{1-6}$ alkyl group which may be substituted with a halogen).
(iii) Compounds of the formula (Ie).

Especially preferred compounds are exemplified by the compounds of (i) to (iii) below.
(i) Compounds wherein:
Ar is a 4-cyanophenyl group, a 4-nitrophenyl group, a 3,5-dichlorophenyl group, a 3,5-dibromophenyl group, a 2,4-dibromophenyl group, a 4-bromophenyl group, a 3-nitro-5-bromophenyl group, a 6-chloro-3-pyridyl group, a 5-chloro-3-thiazolyl group, a 6-chloro-5-fluoro-3-pyridyl group or a 6-trifluoromethyl-3-pyridyl group;
$R_1$ is a hydrogen atom;
$R_2$ is a trifluoromethylsulfonyl group;
$R_3$ is a methylene group, an ethylene group or a 1-propynylene group; and
$R_4$ is a hydrogen atom.
(ii) Compounds wherein:
Ar is a 6-chloro-3-pyridyl group, a 5-chloro-3-thiazolyl group or a 6-trifluoromethyl-3-pyridyl group;
$R_1$ is a hydrogen atom or a methyl group;
$R_2$ is a cyano group or a trifluoromethylcarbonyl group;
$R_3$ is an ethylene group; and
$R_4$ is $SR_5$ ($R_5$ being a $C_{1-6}$ alkyl group which may be substituted with a halogen), S—CS—$OR_8$ or S—CS—$SR_8$ ($R_8$ being a $C_{1-6}$ alkyl group which may be substituted with a halogen).
(iii) Compounds of the formula (Ie).

Preferred forms of the compound of formula (Ie) are compounds wherein:
Ar is a 3-pyridyl group, a 6-chloro-3-pyridyl group, a 5-chloro-3-thiazolyl group, a 6-chloro-5-fluoro-3-pyridyl group, a 6-bromo-3-pyridyl group, a 6-fluoro-3-pyridyl group, a 5,6-dichloro-3-pyridyl group, a 6-trifluoromethyl-3-pyridyl group or a 2-chloro-5-pyrimidyl group;
$R_1$ is a hydrogen atom, a methyl group or an ethyl group;
Y is a hydrogen atom, a halogen atom or a methyl group; and $R_{4e}$ is a trifluoromethyl group, a trichloromethyl group, a dichloromethyl group, a difluoromethyl group, a difluorochloromethyl group, a chloromethyl group or a pentafluoroethyl group.

Compounds wherein:

Ar is a 6-chloro-3-pyridyl group, a 6-fluoro-3-pyridyl group, a 6-chloro-5-fluoro-3-pyridyl group, a 6-bromo-3-pyridyl group or a 2-chloro-5-pyrimidyl group;

$R_1$ is a hydrogen atom or a methyl group;

Y is a hydrogen atom; and $R_{4e}$ is a trifluoromethyl group, a difluoromethyl group, a difluorochloromethyl group, a chloromethyl group or a pentafluoroethyl group are more preferred.

The compound of chemical formula (I) which serves as the active ingredient of the pest control agent of the invention is preferably a compound which has a control activity (e.g., an insect mortality or knockdown rate of at least 30%, at least 50%, at least 80%, or 100%) in foliar application at 500 ppm, soil drenching treatment at 0.1 mg/seedling, or local application at 2 μg/insect (see the test examples for the invention). Alternatively, the compound is one having a control activity (insecticidal effect), as determined by the evaluation of insect mobility, under the root immersion treatment at 20 μg/seedling described in Test Example 15 or under the culturing conditions at about 3 ppm described in Test Example 21.

In foliar application, the compound is more preferably one having a control activity at a concentration of below 500 ppm (e.g., 400 ppm, 300 ppm, 200 ppm, 100 ppm, 50 ppm, 30 ppm, 10 ppm, 5 ppm, 3 ppm, 1.5 ppm, 1.25 ppm, 1 ppm, or 0.5 ppm)

In soil drenching treatment, the compound is more preferably one having a control activity at a concentration below 0.1 mg/seedling (e.g., 0.05 mg/seedling, 0.01 mg/seedling, 0.005 mg/seedling, or 0.002 mg/seedling).

In local application, the compound is more preferably one having a control activity at a concentration below 2 μg/insect (e.g., 1 μg/insect, 0.5 μg/insect, or 0.2 μg/insect).

In dry film application, the compound is more preferably one having a control activity at a concentration below 200 ppm (e.g., 100 ppm, 50 ppm, 30 ppm, or 10 ppm).

In root immersion treatment, the compound is more preferably one having a control activity at a concentration below 20 μg/seedling (e.g., 10 μg/seedling, 5 μg/seedling, 2 μg/seedling, 1 μg/seedling, 0.5 μg/seedling, 0.1 μg/seedling, 0.05 μg/seedling, 0.03 μg/seedling, or 0.01 μg/seedling).

Illustrative examples of the compounds of the invention are listed in Tables 1 to 5.

TABLE 1

| Compound No. | Ar | $R_1$ | $R_2$ | $R_3$ | $R_4$ |
|---|---|---|---|---|---|
| 1 | (I) | H | CN | $CH_2CH_2$ | $SCH_3$ |
| 2 | (I) | H | CN | $CH_2CH_2$ | $SCH_2CH_3$ |
| 3 | (I) | H | CN | $CH_2CH_2$ | $SCH_2CH_2CH_3$ |
| 4 | (I) | H | CN | $CH_2CH_2CH_2$ | H |
| 5 | (I) | H | CN | $CH_2CH_2CH_2$ | $SCH_3$ |
| 6 | (I) | H | CN | $CH_2CH_2$ | $SCSSCH_3$ |
| 7 | (I) | H | CN | $CH_2CH_2$ | $SCSSCH_2CH_3$ |
| 8 | (I) | H | CN | $CH_2CH_2$ | $SCSSCH_2CH_2CH_3$ |
| 9 | (II) | H | CN | $CH_2CH_2$ | $SCSSCH_2CH_3$ |
| 10 | (II) | H | CN | $CH_2CH_2$ | $SCSSCH_2CH_2CH_3$ |
| 11 | (I) | H | CN | $CH_2CH_2$ | $OCH_3$ |
| 12 | (I) | H | CN | $CH_2CH_2CH_2CH_2$ | H |
| 13 | (I) | H | CN | $CH_2$ | H |
| 14 | (I) | H | CN | $CH_2CH_2$ | H |
| 15 | (I) | H | CN | $CH(CH_3)CH_2$ | H |
| 16 | (I) | H | CN | $CH_2CH_2$ | $N(CH_3)_2$ |
| 17 | (I) | H | CN | $CH_2$ | (I) |
| 18 | (I) | Me | CN | $CH_2CH_2$ | H |
| 19 | (II) | H | CN | $CH_2CH_2$ | H |
| 20 | (I) | H | COMe | $CH_2CH_2$ | H |
| 21 | (I) | H | $COCF_3$ | $CH_2CH_2$ | H |
| 22 | (I) | H | COOMe | $CH_2CH_2$ | H |
| 23 | (II) | H | CN | $CH_2CH_2$ | $SCH_3$ |
| 24 | (I) | H | COMe | $CH_2CH_2$ | $SCH_3$ |
| 25 | (I) | H | COOPh | $CH_2CH_2$ | $SCH_3$ |
| 26 | (I) | H | SOOPh | $CH_2CH_2$ | $SCH_3$ |
| 27 | (I) | H | COOMe | $CH_2CH_2$ | $SCH_3$ |
| 28 | (I) | H | SOOMe | $CH_2CH_2$ | $SCH_3$ |
| 29 | (I) | H | CHO | $CH_2CH_2$ | $SCH_3$ |
| 30 | (I) | H | COPh | $CH_2CH_2$ | $SCH_3$ |
| 31 | (I) | H | $COCF_3$ | $CH_2CH_2$ | $SCH_3$ |
| 32 | (II) | H | CN | $CH_2CH_2$ | $SCH_2CH_3$ |
| 33 | (I) | H | $PO(OC_2H_5)_2$ | $CH_2CH_2$ | $SCH_3$ |
| 34 | (I) | H | $COCCl_3$ | $CH_2CH_2$ | $SCH_3$ |
| 35 | phenyl | H | CN | $CH_2CH_2$ | H |
| 36 | 3-pyridyl | H | CN | $CH_2CH_2$ | H |
| 37 | 4-chlorophenyl | H | CN | $CH_2CH_2$ | H |
| 38 | phenyl | H | CN | $CH_2$ | phenyl |
| 39 | phenyl | H | COMe | $CH_2CH_2$ | H |
| 40 | phenyl | H | COOMe | $CH_2CH_2$ | H |
| 41 | 3-thienyl | H | CN | $CH_2CH_2$ | H |
| 42 | (I) | H | CN | $CH_2C \equiv C$ | H |
| 43 | (I) | H | CN | $CH_2CH = CH$ | H |
| 44 | (I) | H | CN | $CH_2$ | phenyl |

TABLE 1-continued

| Compound No. | Ar | $R_1$ | $R_2$ | $R_3$ | $R_4$ |
|---|---|---|---|---|---|
| 45 | 3-cyanophenyl | H | CN | $CH_2CH_2$ | H |
| 46 | 6-trifluoromethyl-3-pyridyl | H | CN | $CH_2CH_2$ | H |
| 47 | 6-trifluoromethyl-3-pyridyl | H | CN | $CH_2CH_2$ | $SCH_3$ |
| 48 | 6-trifluoromethyl-3-pyridyl | H | CN | $CH_2CH_2$ | $SCH_2CH_3$ |
| 49 | (I) | H | CN | $CH_2CH_2$ | $S-CH_2$-(2-furanyl) |
| 50 | (I) | H | CN | $CH_2CH_2$ | $S-CH_2$-phenyl |
| 51 | (I) | H | CN | $CH_2CH_2$ | SOO-phenyl |
| 52 | (I) | H | CN | $CH_2CH_2$ | S-phenyl |
| 53 | (I) | H | CN | $CH_2CH_2$ | O-phenyl |
| 54 | (I) | H | CN | $CH_2CH_2$ | $NHCOCH_3$ |
| 55 | 4-chlorophenyl | H | CN | $CH_2$ | 4-chlorophenyl |
| 56 | (I) | H | CN | $CH_2$ | COOMe |
| 57 | (I) | H | CN | $CH_2CH_2$ | phenyl |
| 58 | (I) | H | CN | $CH_2CH_2$ | COO-phenyl |
| 59 | (I) | H | CN | $CH_2$ | CN |
| 60 | (I) | H | CN | CH(Me) | CN |

TABLE 2

| Compound No. | Ar | $R_1$ | $R_2$ | $R_3$ | $R_4$ |
|---|---|---|---|---|---|
| 61 | (I) | H | CN | $CH_2CH_2$ | OCOMe |
| 62 | (I) | H | CN | $CH_2$ | $SCH_3$ |
| 63 | (II) | H | CN | $CH_2CH_2$ | OCOMe |
| 64 | (II) | H | CN | $CH_2$ | $SCH_3$ |
| 65 | (II) | H | CN | $CH_2CH_2$ | COOMe |
| 66 | (II) | H | CN | $CH_2$ | cyclopropyl |
| 67 | (II) | H | CN | CH(Me)CH | $SCH_3$ |
| 68 | (I) | H | CN | 2-thiiranylene | H |
| 69 | (I) | H | CN | 2-oxyranylen | H |
| 70 | (I) | H | CN | $CH_2CH_2$ | COOMe |
| 71 | (I) | H | CN | $CH_2$ | cyclopropyl |
| 72 | 5,6-dichloro-3-pyridyl | H | CN | $CH_2CH_2$ | $SCH_3$ |
| 73 | (I) | Me | CN | $CH_2CH_2$ | $SCH_3$ |
| 74 | (II) | H | CN | $CH_2CH_2$ | $SCH_3$ |
| 75 | (II) | H | CN | $CH_2CH_2$ | $SCH_2CH_3$ |
| 76 | (I) | H | CN | 3-tetrahydrothiophenylene | H |
| 77 | (I) | H | CN | CH(Me)CH | $SCH_3$ |
| 78 | 6-fluoro-3-pyridyl | H | CN | $CH_2CH_2$ | $SCH_3$ |
| 79 | 6-chloro-5-fluoro-3-pyridyl | H | CN | $CH_2CH_2$ | $SCH_3$ |
| 80 | 6-chloro-5-fluoro-3-pyridyl | H | CN | $CH_2CH_2$ | H |
| 81 | (I) | H | $COCF_3$ | $CH_2CHF$ | H |
| 82 | (I) | H | CN | $CH_2CHF$ | H |
| 83 | (I) | H | CN | $CH_2$ | (II) |
| 84 | (I) | H | CN | $CH_2CH_2$ | OTs |
| 85 | (I) | H | CN | $CH_2CH_2$ | $SCSN(Et)CH_2Ph$ |
| 86 | (I) | H | CN | $CH_2CH_2$ | SCSOEt |
| 87 | (II) | H | CN | $CH_2CH_2$ | SCSOEt |
| 88 | (I) | H | CN | $CH_2CH_2$ | $SCSN(Me)CH_2Ph$ |
| 89 | (I) | Me | $COCF_3$ | $CH_2CHF$ | H |
| 90 | (I) | H | CN | $CH_2CH_2$ | SCSOiPr |
| 91 | (I) | H | CN | $CH_2CH_2$ | SCSO—n-pentyl |
| 92 | (I) | Me | CN | $CH_2CHF$ | H |
| 93 | (I) | H | CN | $CH_2CH_2$ | SCSO—n-Pr |
| 94 | (I) | H | CN | $CH_2CH_2$ | SCSO—n-Bu |
| 95 | (II) | H | CN | $CH_2CF_2$ | H |
| 96 | (I) | Me | $COCF_3$ | $CH_2CF_2$ | H |
| 97 | (I) | H | $COCF_3$ | $CH_2CF_2$ | H |
| 98 | (I) | H | $COCF_2Cl$ | $CH_2CF_2$ | H |
| 99 | (I) | H | $COCCl_3$ | $CH_2CF_2$ | H |
| 100 | (I) | H | CN | $CH_2CH_2CH_2$ | OTs |

TABLE 2-continued

| Compound No. | Ar | $R_1$ | $R_2$ | $R_3$ | $R_4$ |
|---|---|---|---|---|---|
| 101 | (I) | H | CN | $CH_2CH_2CH_2$ | SCSOEt |
| 102 | (I) | H | CN | $CH_2CH_2CH_2$ | SCSO—n-Pr |
| 103 | (I) | H | CN | $CH_2CH_2CH_2$ | SCSN(Et)$CH_2$Ph |
| 104 | (I) | H | $SO_2CF_3$ | $CH_2CF_2$ | H |
| 105 | (I) | Me | $COCF_3$ | $CH_2CH_2$ | H |
| 106 | (I) | Me | $COCF_3$ | $CH_2CH_2CF_2$ | H |
| 107 | (I) | Me | $SO_2CF_3$ | $CH_2CH_2$ | H |
| 108 | (I) | Me | $SO_2CF_3$ | $CH_2CF_2$ | H |
| 109 | (I) | Et | $COCF_3$ | $CH_2CF_2$ | H |
| 110 | (I) | Et | $SO_2CF_3$ | $CH_2CF_2$ | H |
| 111 | (I) | Et | $COCF_3$ | $CH_2CH_2$ | H |
| 112 | (I) | Et | $SO_2CF_3$ | $CH_2CH_2$ | H |
| 113 | (I) | H | CN | $CH_2CH_2$ | S—$CH_2$-(2-imidazolyl) |
| 114 | 6-trifluoromethyl-3-pyridyl | Me | $SO_2CF_3$ | $CH_2CH_2$ | H |
| 115 | 6-trifluoromethyl-3-pyridyl | Me | $COCF_3$ | $CH_2CH_2$ | H |
| 116 | (II) | Me | $SO_2CF_3$ | $CH_2CH_2$ | H |
| 117 | (II) | Me | $SO_2CF_3$ | $CH_2CF_2$ | H |
| 118 | (II) | Et | $COCF_3$ | $CH_2CF_2$ | H |
| 119 | (II) | H | CN | $CH_2CH=CH$ | H |
| 120 | (II) | H | CN | $CH_2C\equiv C$ | H |

TABLE 3

| Compound No. | Ar | $R_1$ | $R_2$ | $R_3$ | $R_4$ |
|---|---|---|---|---|---|
| 121 | (II) | H | CN | $CH_2$ | H |
| 122 | (II) | H | CN | $CH_2CH_2CH_2$ | H |
| 123 | (II) | Et | $SO_2CF_3$ | $CH_2CF_2$ | H |
| 124 | 2-pyridyl | Me | $SO_2CF_3$ | $CH_2CH_2$ | H |
| 125 | (II) | Et | $SO_2CF_3$ | $CH_2CF_2$ | H |
| 126 | (II) | Et | $COCF_3$ | $CH_2CH_2$ | H |
| 127 | (II) | Et | $SO_2CF_3$ | $CH_2CH_2$ | H |
| 128 | (I) | H | $SO_2CF_3$ | $CH_2C\equiv C$ | H |
| 129 | (I) | H | $SO_2CF_3$ | $CH_2$ | CN |
| 130 | 4-trifluoromethyl-3-pyridyl | H | $COCF_3$ | $CH_2CH_2$ | H |
| 131 | 6-trifluoromethyl-3-pyridyl | H | $SO_2CF_3$ | $CH_2CH_2$ | H |
| 132 | 4-pyridyl | Me | $COCF_3$ | $CH_2CH_2$ | H |
| 133 | 3-pyridyl | Me | $COCF_3$ | $CH_2CH_2$ | H |
| 134 | 2-pyridyl | Me | $COCF_3$ | $CH_2CH_2$ | H |
| 135 | (I) | H | $SO_2CF_3$ | $CH_2$ | H |
| 136 | (II) | H | CN | $CH_2CH_2$ | OTs |
| 137 | (II) | H | CN | $CH_2CH_2$ | SCSOEt |
| 138 | (II) | H | CN | $CH_2CH_2$ | SCSN($CH_2$Ph)Et |
| 139 | (I) | H | CN | $CH_2CH_2$ | S(=O)Ph |
| 140 | (I) | H | $SO_2CF_3$ | $CH_2CH_2CH_2$ | H |
| 141 | (I) | H | $SO_2CF_3$ | $CH_2CH_2CH_2CH_2$ | H |
| 142 | (I) | H | $SO_2CF_3$ | $CH_2CH_2$ | SOOPh |
| 143 | (I) | H | $SO_2CF_3$ | $CH_2CH_2$ | OPh |
| 144 | (I) | H | $SO_2CF_3$ | $CH_2CH_2$ | H |
| 145 | (I) | H | $SO_2CF_3$ | $CH_2CH_2CH_2$ | H |
| 146 | (I) | H | $SO_2CF_3$ | $CH_2CH=CH$ | H |
| 147 | (I) | H | $SO_2CF_3$ | $CH_2$ | Ph |
| 148 | 4-fluoro-3-pyridyl | H | CN | $CH_2CH_2$ | H |
| 149 | 4-bromo-3-pyridyl | H | CN | $CH_2CH_2$ | H |
| 150 | (I) | H | $SO_2CF_3$ | $CH_2CH_2$ | $NMe_2$ |
| 151 | (I) | Me | $SO_2CF_3$ | $CH_2CH_2$ | $NMe_2$ |
| 152 | (I) | H | $SO_2CF_3$ | $CH_2CH_2C\equiv C$ | H |
| 153 | 3-chloro-4-pyridyl | H | CN | $CH_2CH_2$ | H |
| 154 | 3-chloro-2-pyridyl | H | CN | $CH_2CH_2$ | H |
| 155 | (I) | H | $SO_2CF_3$ | $CH_2CH_2$ | $OCH_3$ |
| 156 | (II) | H | $SO_2CF_3$ | $CH_2CH_2$ | $OCH_3$ |
| 157 | 6-chloro-3-pyridazyl | H | $COCF_3$ | $CH_2CH_2$ | H |
| 158 | 3,5-dichlorophenyl | H | CN | $CH_2CH_2$ | H |
| 159 | (I) | H | $SO_2CF_3$ | $CH_2CH_2$ | CN |
| 160 | (I) | H | $SO_2CF_3$ | $CH_2$ | COOMe |

TABLE 3-continued

| Compound No. | Ar | $R_1$ | $R_2$ | $R_3$ | $R_4$ |
|---|---|---|---|---|---|
| 161 | (I) | H | $SO_2CF_3$ | $CN_2$ | COOH |
| 162 | 4-fluorophenyl | H | $SO_2CF_3$ | $CH_2CH_2$ | $OCH_3$ |
| 163 | (II) | H | $SO_2CF_3$ | $CH_2$ | CN |
| 164 | 4-methylphenyl | H | $SO_2CF_3$ | $CH_2CH_2$ | $OCH_3$ |
| 165 | 6-trifluoromethyl-3-pyridyl | H | $SO_2CF_3$ | $CH_2$ | CN |
| 166 | 2-pyridyl | H | $SO_2CF_3$ | $CH_2CH_2$ | $OCH_3$ |
| 167 | 6-chloro-5-fluoro-3-pyridyl | H | $SO_2CF_3$ | $CH_2$ | CN |
| 168 | 3-pyridyl | H | $SO_2CF_3$ | $CH_2CH_2$ | $OCH_3$ |
| 169 | 4-pyridyl | H | $SO_2CF_3$ | $CH_2CH_2$ | $OCH_3$ |
| 170 | (I) | Me | $SO_2CF_3$ | $CH_2$ | CN |
| 171 | (I) | Me | $SO_2CF_3$ | $CH_2C\equiv C$ | H |
| 172 | (II) | H | $SO_2CF_3$ | $CH_2C\equiv C$ | H |
| 173 | 6-fluoro-3-pyridyl | H | $SO_2CF_3$ | $CH_2CH_2$ | $OCH_3$ |
| 174 | 6-bromo-3-pyridyl | H | $SO_2CF_3$ | $CH_2CH_2$ | $OCH_3$ |
| 175 | 3,5-dichlorophenyl | Me | $COCF_3$ | $CH_2CH_2$ | H |
| 176 | 3,5-dichlorophenyl | H | $COCF_3$ | $CH_2CH_2$ | H |
| 177 | phenyl | H | $SO_2CF_3$ | $CH_2CH_2$ | H |
| 178 | (I) | H | $SO_2CH_2CF_3$ | $CH_2CH_2$ | H |
| 179 | (I) | H | $SO_2CH_2CF_3$ | $CH_2C\equiv C$ | H |
| 180 | 3-chlorophenyl | H | $SO_2CF_3$ | $CH_2CH_2$ | H |

TABLE 4

| Compound No. | Ar | $R_1$ | $R_2$ | $R_3$ | $R_4$ |
|---|---|---|---|---|---|
| 181 | 4-chlorophenyl | H | $SO_2CF_3$ | $CH_2CH_2$ | H |
| 182 | 3-cyanophenyl | H | $SO_2CF_3$ | $CH_2CH_2$ | H |
| 183 | 4-nitrophenyl | H | $SO_2CF_3$ | $CH_2CH_2$ | H |
| 184 | 3,5-dichlorophenyl | H | $SO_2CF_3$ | $CH_2C\equiv C$ | H |
| 185 | 4-methylphenyl | H | $SO_2CF_3$ | $CH_2CH_2$ | H |
| 186 | 4-cyanophenyl | H | $SO_2CF_3$ | $CH_2CH_2$ | H |
| 187 | 4-methoxyphenyl | H | $SO_2CF_3$ | $CH_2CH_2$ | H |
| 188 | 4-fluorophenyl | H | $SO_2CF_3$ | $CH_2CH_2$ | H |
| 189 | 3,5-dibromophenyl | H | $SO_2CF_3$ | $CH_2CH_2$ | H |
| 190 | 4-bromophenyl | H | $SO_2CF_3$ | $CH_2CH_2$ | H |
| 191 | 3,5-dimethylphenyl | H | $SO_2CF_3$ | $CH_2CH_2$ | H |
| 192 | 3-nitrophenyl | H | $SO_2CF_3$ | $CH_2CH_2$ | H |
| 193 | 2,4-dibromophenyl | H | $SO_2CF_3$ | $CH_2CH_2$ | H |
| 194 | 3-nitro-5-bromophenyl | H | $SO_2CF_3$ | $CH_2CH_2$ | H |
| 195 | 3,5-bistrifluoromethylphenyl | H | $SO_2CF_3$ | $CH_2CH_2$ | H |
| 196 | (I) | H | CN | $CH_2CH_2$ | $SCSSCH_2COOCH_3$ |
| 197 | (II) | Me | CN | $CH_2CH_2$ | $SCSSCH_2CH_2CH_3$ |
| 198 | (I) | H | CN | $CH_2CH_2$ | $SCSSCH_2OMe$ |
| 199 | (I) | H | CN | $CH_2CH_2$ | $SCSSCH_2SMe$ |
| 200 | (I) | H | CN | $CH_2CH_2$ | $SCSSCH_2CO$-(4-methylphenyl) |
| 201 | 3-tetrahydrofuranyl | H | CN | $CH_2CH_2$ | H |
| 202 | 3-tetrahydrofuranyl | H | CN | $CH_2CH_2$ | SMe |
| 203 | (I) | H | COPh | $CH_2CH_2$ | H |
| 204 | (I) | H | $COCH_2CH_3$ | $CF_2$ | H |
| 205 | (I) | H | $CONH_2$ | $CH_2CH_2$ | H |
| 206 | (I) | H | CONHMe | $CH_2CH_2$ | H |
| 207 | (I) | H | $CONMe_2$ | $CH_2CH_2$ | H |
| 208 | (I) | H | $NO_2$ | $CH_2CH_2$ | H |
| 209 | (I) | H | $COCClF_2$ | $CH_2CH_2$ | H |
| 210 | (I) | H | CN | phenylene | H |
| 211 | (I) | Me | $SO_2CF_3$ | $CH_2$ | H |
| 245 | (I) | H | COMe | $CH_2$ | CN |
| 246 | (I) | H | $COCF_3$ | $CH_2$ | CN |

(I): 6-chloro-3-pyridyl (II): 5-chloro-3-thiazolyl

TABLE 5

| Compound No. | Ar | $R_1$ | $R_{4e}$ | Y |
|---|---|---|---|---|
| 212 | (I) | H | $CF_3$ | H |
| 213 | (II) | H | $CF_3$ | H |
| 214 | (I) | H | $OCH_3$ | H |
| 215 | (I) | H | $CF_3$ | 5-Cl |
| 216 | (I) | H | $CF_3$ | 5-F |
| 217 | (I) | H | $CF_3$ | 4-Cl |
| 218 | (II) | H | $CF_3$ | 5-Cl |
| 219 | (II) | H | $CF_3$ | 5-F |
| 220 | (II) | H | $CF_3$ | 4-Cl |
| 221 | (I) | H | $CF_3$ | 3-Me |
| 222 | (I) | H | $CF_3$ | 4-Me |
| 223 | (I) | H | $CF_3$ | 5-Me |
| 224 | phenyl | H | $CF_3$ | H |
| 225 | 4-chlorophenyl | H | $CF_3$ | H |
| 226 | 3-pyridyl | H | $CF_3$ | H |
| 227 | 6-chloro-5-fluoro-3-pyridyl | H | $CF_3$ | H |
| 228 | 6-trifluoromethyl-3-pyridyl | H | $CF_3$ | H |
| 229 | 6-fluoro-3-pyridyl | H | $CF_3$ | H |
| 230 | 5,6-dichloro-3-pyridyl | H | $CF_3$ | H |
| 231 | 6-bromo-3-pyridyl | H | $CF_3$ | H |
| 232 | (I) | H | $CF_3$ | 4-F |
| 233 | (I) | H | $CF_3$ | 3-F |
| 234 | (I) | H | $CHCl_2$ | H |
| 235 | (I) | H | $CCl_3$ | H |
| 236 | (I) | H | $CH_2Cl$ | H |
| 237 | (I) | Me | $CF_3$ | H |
| 238 | (I) | H | $CHF_2$ | H |
| 239 | (I) | H | $CF_2Cl$ | H |
| 240 | (I) | H | $CHClBr$ | H |
| 241 | (I) | H | $CHBr_2$ | H |
| 242 | (I) | H | $CF_2CF_3$ | H |
| 243 | 2-chloro-pyrimidinyl | H | $CF_3$ | H |
| 244 | (I) | H | $CH_2Br$ | H |

The most preferred compounds are the following which appear in Table 5:
Compound No. 212: N-[1-((6-chloropyridin-3-yl)methyl)pyridin-2(1H)-ylidene]-2,2,2-trifluoroacetamide,
Compound No. 227: N-[1-((6-chloro-5-fluoropyridin-3-yl)methyl)pyridin-2(1H)-ylidene]-2,2,2-trifluoroacetamide,
Compound No. 229: N-[1-((6-fluoropyridin-3-yl)methyl)pyridin-2(1H)-ylidene]-2,2,2-trifluoroacetamide,
Compound No. 231: N-[1-((6-bromopyridin-3-yl)methyl)pyridin-2(1H)-ylidene]-2,2,2-trifluoroacetamide,
Compound No. 237: N-[1-(1-(6-chloropyridin-3-yl)ethyl)pyridin-2(1H)-ylidene]-2,2,2-trifluoroacetamide,
Compound No. 238: N-[1-((6-chloropyridin-3-yl)methyl)pyridin-2(1H)-ylidene]-2,2-difluoroacetamide,
Compound No. 239: 2-chloro-N-[1-((6-chloropyridin-3-yl)methyl)pyridin-2(1H)-ylidene]-2,2-difluoroacetamide,
Compound No. 242: N-[1-((6-chloropyridin-3-yl)methyl)pyridin-2(1H)-ylidene]-2,2,3,3,3-pentafluoropropanamide, and
Compound No. 243: N-[1-((2-chloropyrimidin-5-yl)methyl)pyridin-2(1H)-ylidene]-2,2,2-trifluoroacetamide.

Compound No. 212 in Table 5, N-[1-((6-chloropyridin-3-yl)methyl)pyridin-2(1H)-ylidene]-2,2,2-trifluoroacetamide, has the following physical properties. These properties have not been mentioned in any of the prior-art documents.
(a) In powder x-ray diffraction analysis, the compound has diffraction angle peaks at least at the following diffraction angles (2θ): 8.6±0.2°, 14.2±0.2°, 17.5±0.2°, 18.3±0.2°, 19.7±0.2°, 22.3±0.2°, 30.9±0.2°, 35.3±0.2°
(b) In differential scanning calorimetry (DSC), the compound exhibits a melting point of 155 to 158° C.

Examples of the types of pests on which pest control agents containing at least one of the inventive compounds of chemical formula (I) exhibit control effects are given below.

Examples of agricultural/horticultural pests include lepidopterous pests (e.g., common cutworm, cabbage armyworm, armyworm, cabbage butterfly caterpillar, diamondback moth, beet armyworm, rice stem borer, grass leaf roller, rice green caterpillar, leaf roller moth, codling moth, leaf miner moth, oriental tussock moth, pests belonging to the genus Agrotis (Agrotis spp.), pests belonging to the genus Helicoverpa (Helicoverpa spp.), and pests belonging to the genus Heliothis (Heliothis spp.)), hemipterous pests (e.g., aphids (Aphididae, Adelgidae, Phylloxeridae) such as the green peach aphid, cotton aphid, Aphis fabae, corn leaf aphid, pen aphid, foxglove aphid, Aphis craccivora, Macrosiphum euphorbiae, Macrosiphum avenae, Methopolophium dirhodum, grain aphid, Schizaphis graminum, cabbage aphid, turnip aphid, spiraea aphid, rosy apple aphid, woolly apple aphid, Toxoptera aurantii and brown citrus aphid; leafhoppers such as the green rice leafhopper and the tea green leafhopper; planthoppers such as the small brown planthopper and the white-backed rice planthopper; stink bugs such as the white-spotted bug, the southern green stink bug, the brown-winged green bug and the rice leaf bug; whiteflies (Aleyrodidae) such as the silverleaf whitefly, the sweet potato whitefly and the greenhouse whitefly; and scale insects such as Pseudococcus comstocki, the citrus mealybug, the white peach scale and the California red scale (e.g., Diaspididae, Margarodidae, Ortheziidae, Aclerdiae, Dactylopiidae, Kerridae, Pseudococcidae, Coccidae, Eriococcidae, Asterolecaniidae, Beesonidae, Lecanodiaspididae, Cerococcidae)), coleopterous pests (e.g., rice water weevil, adzuki bean weevil, yellow mealworm, Western corn root worm, Southern corn root worm, cupreous chafer, soy bean beetle, striped flea beetle, cucurbit leaf beetle, Colorado potato beetle, rice leaf beetle, codling moth larvae and longicorn beetles), pests belonging to the order Acarina (e.g., the two-spotted spider mite, the Kanzawa spider mite and Panonychus citri), hymenopterous pests (e.g., sawflies), orthopterous pests (e.g., grasshoppers and locusts), dipterous pests (e.g., the housefly and leaf miner flies), thysanopterous pests (e.g., melon thrips and Western flower thrips), and plant parasitic nematodes (the root knot nematode, the root lesion nematode, the rice white-tip nematode and the pine wood nematode).

Examples of animal parasitic pests include hard-bodied ticks (e.g., lone star tick, Gulf Coast tick, cattle tick, Rocky Mountain wood tick, West Coast tick, American dog tick, Haemaphysalis campanulata, Haemaphysalis flava, Haemaphysalis longicornis, Haemaphysalis megaspinosa, Ixodes nipponensis, Ixodes ovatus, Western black-legged tick, Ixodes persulcatus, castor bean tick, black-legged tick, Ornithodoros moubata and brown dog tick), Cheyletidae spp. (e.g., Cheyletiella blackei and Cheyletiella yasguri), demodex mites (e.g., Demodex canis and Demodex cati), Psoroptidae spp. (e.g., Psoroptes communis), mange mites (e.g., Chorioptes bovis and Otodectes cynotis), Dermanyssidae spp. (e.g., Ornithonyssus sylviarum), parasitoid mites, feather mites (e.g., Menacanthus cornutus and Pterolichus obtusis), Trombiculidae spp. (e.g., Helenicula miyagawai and Leptotrombidium akamusi), fleas, (e.g., the cat flea, dog flea, sticktight flea, human flea and Oriental rat flea), chewing lice (e.g., dog louse, chicken louse), sucking lice (e.g., hog louse, dog sucking louse, body louse, Pediculus humanus, pubic louse, common bed bug), muscid flies, warble flies, stable flies, horse flies, sand flies (e.g., biting sand fly), tsetse fly, tabanid flies, aedine mosquitoes (e.g., the Tiger mosquito and yellow fever mosquito), culicine mosquitoes (e.g., Culex pipiens pallens), anopheline mosquitoes, biting midges, buffalo gnats, assassin bugs, the pharaoh ant, nematodes (e.g., Strongyloididae, Ancylotomatoidea, Strongylida (e.g., *Haemonchus contortus, Nippostrongylus brasiliensis*), Trichostrongyloidea, Metastrongyloidea (e.g., *Metastrongylus apr, Anriostrongylus cantonesis, Aelurostrongylus abstrusus*), Oxyuroidea, Haterakoidea (e.g., *Ascaridiidae galli*), Ascaridoidea (e.g., *Anisakis simplex, Ascaris lumbricoides suum, Parascaris equorum, Toxocara canis, Toxocara cati*), Spirurida (e.g., Subuluroidea, *Gnathostoma spiniqerum, Physaloptea praeputialis, Ascarops strongylina, Draschia megastoma, Ascaria hamulosa, Dracunculus medinensis*), Filaroidea (e.g., *Dirofilaria immitis, Wuchereria bancrofti, Onchocerca volvulus, Loa loa*), Dioctophymatoidea, Trichinelloidea (e.g., *Trichuris vulpis, Trichinella spiralis*)), Trematoda (e.g., *Schistosoma japonicum, Fasciola* spp.), Acanthocephala, Cestoda (e.g., *Pseudophyllidea* (e.g., *Spirometra erinaceieuropaei*), Cyclophyllidea (e.g., *Dipylidium caninum*)), and Protozoa.

Health pests, nuisance pests, stored_ grain pests, stored food pests and household pests include mosquitoes (e.g., the Tiger mosquito and *Culex pipiens pallens*), cockroaches (e.g., the smoky-brown cockroach, *Periplaneta fuliginosa*, and the German cockroach), grain mites (e.g., the common grain mite), flies (e.g., the house fly, *Sarcophagidae* spp., sand flies, small fruit flies and *Chironomidae* spp.), buffalo gnats, biting midges, hymenopterous insects (e.g., ants such as *Camponotus japonicas* and fire ants, and hornets such as the Japanese giant hornet), arthropods of the order Isopoda (e.g., the rough woodlouse, wharf roach, pill bug), hemipterous insects (e.g., common bed bug), arthropods of the subphylum Myriapoda (e.g., centipedes, *Chilopoda* spp., millipedes), arthropods of the order Araneae (e.g., the huntsman spider), coleopterous insects (e.g., ground beetle), arthropods of the order Collembola (e.g., *Onychiurus folsomi*), insects of the order Dermaptera (e.g., the giant earwig), insects of the order Orthoptera (e.g., *Stenopelmatidae* spp.), insects of the order Coleoptera (e.g., adzuki bean weevil, rice weevil, cadelle, rust-red flour beetle, whitemarked spider beetle, deathwatch, bark beetles, dermestid beetles, *Chlorophorus diadema*), insects of the order Lepidoptera (e.g., pyralid moths, clothes moths), *Hemipeplidae* spp., insects of the order Isoptera (e.g., the house termite, western drywood termite, *Odontotermes formosanus*), and the order Thysanura (e.g., oriental silverfish).

Of these, preferred examples of pests on which suitable use may be made of the inventive pest control agent include lepidopterous pests, hemipterous pests, thysanopterous pests, dipterous pests, coleopterous pests, animal parasitic fleas and ticks, and canine heartworms (e.g., at least one pest selected from the group consisting of diamondback moth, common cutworm, cotton aphid, green peach aphid, small brown planthopper, brown rice planthopper, white-backed rice planthopper, green rice leafhopper, rice leaf bug, brown-winged green bug, western flower thrips, rice leaf beetle, rice water weevil, house fly, *Haemaphysalis longicornis* and canine heartworm). Hemipterous pests, coleopteous pests and hard-bodied ticks are more preferred. Planthoppers and the green rice leafhopper are especially preferred.

Therefore, the pest control agents provided by the present invention are exemplified by insecticides for agricultural and horticultural use, control agents for internal animal parasites, control agents for external animal parasites, control agents for sanitary pests, control agents for nuisance pests, control agents for stored grain/stored food pests, and control agents for household pests. Insecticides for agricultural and horticultural use, control agents for internal animal parasites and control agents for external animal parasites are preferred.

The pest control agents of the invention may be prepared using, aside from a compound of chemical formula (I), a carrier suitable for the intended method of use.

When the pest control agent of the invention is an agricultural pest control agent, the active ingredient is generally mixed with a suitable solid carrier, liquid carrier, gaseous carrier, surfactant, dispersant and other adjuvants, and the agent is furnished in any desired form, such as an emulsifiable concentrate, liquid formulation, suspension concentrate, wettable powder, flowable concentrate, dust, granules, tablets, oil solution, aerosol or smoking agent.

Illustrative examples of solid carriers include talc, bentonite, clay, kaolin, diatomaceous earth, vermiculite, white carbon and calcium carbonate.

Illustrative examples of liquid carriers include alcohols such as methanol, n-hexanol and ethylene glycol, ketones such as acetone, methyl ethyl ketone and cyclohexanone, aliphatic hydrocarbons such as n-hexane and kerosene, aromatic hydrocarbons such as toluene, xylene and methyl naphthalene, ethers such as diethyl ether, dioxane and tetrahydrofuran, esters such as ethyl acetate, nitriles such as acetonitrile and isobutyronitrile, acid amides such as dimethylformamide and dimethylacetamide, vegetable oils such as soy oil and cottonseed oil, dimethylsulfoxide, and water.

Illustrative examples of gaseous carriers include liquid propane gas, air, nitrogen, carbon dioxide and dimethyl ether.

Surfactants and dispersants which may be used for the purpose of emulsification, dispersion, spreading, sticking and the like include alkylsulfuric acid esters, alkyl(aryl) sulfonic acid salts, polyoxyalkylene alkyl(aryl) ethers, polyol esters, and ligninsulfonic acid salts.

Adjuvants which may be used for improving the properties of the formulation include carboxymethylcellulose, gum arabic, polyethylene glycol and calcium stearate.

The above carriers, surfactants, dispersants and adjuvants may each be used singly or in combination, as needed.

The active ingredient content within the above formulation, although not particularly limited, is typically set to from 1 to 75 wt % in emulsifiable concentrates, from 0.3 to 25 wt % in dusts, from 1 to 90 wt % in wettable powders, and from 0.5 to 10 wt % in granules.

The compounds of chemical formula (I), formulations containing these compounds, and mixtures of these with other pest control agents may be suitably applied to, for example, insect pests, plants, plant propagation materials (e.g., seeds, plant foliage, roots, germinated plants, and seedlings), soils, nutrient solutions in hydroponics, solid media in hydroponics, or rooms needed to prevent infestation by pests. Plants subjected to such application include genetically modified crops.

Such application may be carried out before and after pest infestation.

In particular, the compounds of chemical formula (Ie), formulations containing same, and combinations of these with other pest control agents, by being applied at an effective dose to a target selected from the gioup consisting of seeds, roots, tubers, bulbs, rhizomes, germinated plants, seedlings, soils, nutrient solutions in hydroponics and solid media in hydroponics, and thus being allowed to penetrate and translocate into the plant, are able to control pests.

In cases where the above targets of application are the seeds, roots, tubers, bulbs or rhizomes of plants, preferred examples of the method of application are not particularly limited provided penetration and translocation is unhindered and include, for example, dipping methods, dust coating methods, smearing methods, spraying methods, pellet methods and film coating methods.

In the case of seeds, examples of the method of application include dipping, dust coating, smearing, spraying, pellet application, film coating and fumigation. Dipping is a method for immersing the seeds in a liquid solution of the pest control agent. Dust coating methods include dry dust coating which involves coating the pest control agent in powdered form onto dry seeds, and wet dust coating which involves coating the pest control agent in powdered form onto lightly water-moistened seeds. Other methods are a smearing method for applying the pest control agent in a suspended form onto the surface of seeds within a mixer, and a spraying method for spraying the same onto the surface of the seeds. Additional methods of application include a pellet method in which, when the seeds are formed together with a filler into pellets of a given size and shape, treatment is carried out by mixing the pest control agent with the filler; a film coating method which entails coating the seeds with a film containing the pest control agent; and a fumigation method which entails disinfection of the seeds with the pest control agent that has been gasified within a closed vessel.

In the case of application to germinated plants and seedlings, these plants may be protected by application, via systemic or partial treatment by dipping, following germination and following emergence from the soil, but prior to transplantation.

In the case of application to seeds, roots, tubers, bulbs or rhizomes, an additional consideration is planting or dipping the seeds, roots, tubers, bulbs or rhizomes for a time sufficient to allow penetration and translocation of the pest control agent. In such a case, the time and temperature at which dipping is carried out may be suitably determined by a person skilled in the art in accordance with the target of application and the type and dose of the chemical. In addition, the penetration and translocation time is not subject to any particular limitation, and may be, for example, 1 hour or more. The temperature during penetration and translocation is, for example, from 5 to 45° C.

Methods of application to the soil are exemplified by the application of the inventive compound, formulations containing the same, or granules of mixtures thereof with other pest control agents, either into soil or onto soil. Preferred soil application methods are spraying, band application, furrow application and planting hole treatment. Here, spraying treatment is surface treatment over the entire surface area to be treated, and encompasses subsequent mechanical introduction into the soil.

Another useful method of soli treatment involves application by drenching soil with a solution of the inventive compounds, a formulation containing the same, or a mixture thereof with another pest control agent that has been emulsified or dissolved in water.

In the case of application to nutrient solutions in nutricultural systems for the production of vegetables and flowering plants, such as solid medium cultivation, including hydroponics, sand culture, the nutrient film technique (NFT) and the rock wool technique, it is obvious that the inventive compounds or formulations containing the same, or mixtures of these with other pest control agents, can be directly applied to an artificial plant growth medium containing vermiculite or a solid medium containing an artificial mat for raising seedlings.

In the above application step, the effective dose of the compound of formula (1) or a salt thereof, or of a compound of formula (Ie) or a salt thereof, is preferably an amount sufficient for the compound of formula (1) or formula (Ie) to penetrate and translocate in the subsequent penetration and translocation step.

This effective dose may be suitably decided while taking into consideration such factors as the properties of the compound, the type and amount of the target of application, the length of the subsequent penetration and translocation step, and the temperature. For example, in the case of application to seeds, the dose of the compound of formula (1) or a salt thereof, or of the compound of formula (Ie) or a salt thereof, is preferably from 1 g to 10 kg, and more preferably from 10 g to 1 kg, per 10 kg of seed. In the case of application to soil, the dose of the compound of formula (1) or a salt thereof, or of the compound of formula (Ie) or a salt thereof, is preferably from 0.1 g to 10 kg, and more preferably from 1 g to 10 kg, per 10 ares of cultivated land. In the case of foliar application to plants, the dose of the compound of formula (1) or a salt thereof, or of the compound of formula (Ie) or a salt thereof, is preferably from 0.1 g to 10 kg, and more preferably from 1 g to 1 kg, per 10 areas of cultivated land.

In cases where the pest control agent of the invention is an agent for controlling animal parasitic pests, it may be furnished as, for example, a liquid formulation, an emulsifiable concentrate, liquefied drop formulation, a spray, a foam formulation, tablets, granules, fine granules, a dust, capsules, tablets, a chewable preparation, an injection, a suppository, a cream, a shampoo, a rinse, a resin formulation, a smoking agent or as poisonous bait. Supply as a liquid formulation or a liquid formulation for drop is especially preferred.

In liquid formulations, adjuvants soon as common emulsifying agents, dispersants, spreaders, wetting agents, suspending agents preservatives and propellants may also be included, in addition to which ordinary film-forming agents may be included as well. Surfactants which may be used for emulsification, dispersion, spreading, sticking and the like include soaps, polyoxyalkylene alkyl(aryl) ethers, polyoxyethylene alkylallyl ethers, polyoxyethylene fatty acid esters, higher alcohols and alkyl aryl sulfonates. Examples of dispersants include casein, gelatin, polysaccharides, lignin derivatives, sugars and synthetic water-soluble polymers. Examples of spreading and wetting agents include glycerol and polyethylene glycol. Examples of suspending agents include casein, gelatin, hydroxypropyl cellulose and gum arabic. Examples of stabilizers include phenol-based antioxidants (e.g., BHT, BHA), amine-based antioxidants (e.g., diphenylamine), and organosulfur-based antioxidants. Examples of preservatives include methyl p-oxybenzoate, ethyl p-oxybenzoate, propyl p-oxybenzoate and butyl p-oxybenzoate. The above carriers, surfactants, dispersants and adjuvants may each be used, as needed, either singly or as combinations thereof. In addition, fragrances and synergists may also be included. In a liquid formulation, it is suitable for the active ingredient content in the pest control agents of the invention to be generally from 1 to 75 wt %.

Carriers used for preparing a cream formulation are exemplified by non-volatile hydrocarbons (e.g., liquid paraffin), lanolin fats added with water and oils, higher fatty acids, fatty acid esters, vegetable oils, silicone oils, and water. In addition, emulsifying agents, humectants, antioxidants, fragrances, borax and ultraviolet absorbers may each be used, either singly or in combination thereof, as needed. Examples of emulsifying agents include fatty acid sorbitans, polyoxyethylene alkyl ethers and fatty acid polyoxyethylenes. An active ingredient content within the inventive pest control agent of generally from 0.5 to 70 wt % is appropriate in cream formulations.

In the case of capsules, pills or tablets, the active ingredient within the inventive composition is suitably divided up and mixed with a diluting liquid or a carrier such as starch, lactose or talc, in addition to which a disintegrant such as magnesium stearate and/or a binder are added. If necessary, the formulation may be tableted prior to use.

In the case of injections, preparation must be carried out as a sterile solution. The injection may include sufficient salt or glucose to render the solution isotonic with blood. Examples of carriers that may be used to prepare the injection include organic solvents such as glycerides, benzyl benzoate, isopropyl myristate, the fatty acid derivatives of propylene glycol and other esters, and N-methylpyrrolidone and glycerol formal. An active ingredient content within the inventive pest control agent of generally from 0.01 to 10 wt % is appropriate in injections.

Examples an carriers for preparing a resin formulation include vinyl chloride-based polymers and polyurethane. If necessary, a plasticizer such as a phthalic acid ester, an adipic acid ester or stearic acid may be added as the base for such formulations. After kneading the active ingredient into this base, the resin formulation is shaped such as by injection molding, extrusion or molding under applied pressure. In addition, by suitably passing through such steps as molding and cutting, the formulation may be rendered into ear tags for animals and pest control collars for animals.

Examples of carriers for poisoned bait include teed substances and attractants (e.g., cereal flours such as wheat flour and cornmeal, starches such as corn starch and potato starch, sugars such as granular sugar, barley malt and honey, flood flavors such as glycerol, onion flavor and milk flavor, animal-based powders such as silkworm powder and fish Powder, and various pheromones). An active ingredient content within the inventive pest control agent of generally from 0.0001 to 90 wt % is appropriate in poisoned bait.

Pest control may be carried out by administering the inventive pest control agent within the body of the target animal, either orally or by injection, or by applying the inventive pest control agent to all or part of the body surface of the target animal. Alternatively, pest control may also be carried out by coating places where it is expected that pests will invade, parasitize or move through with the pest control agent of the invention.

The pest control agent of the invention may be used directly as is, or may, depending on the particular case, be applied after dilution with, for example, water, a liquid carrier, or a commercial shampoo, rinse, feed or animal bedding.

Also, the pest control agents according to the invention may be used in admixture with other chemicals, such as fungicides, insecticides, acaricides, herbicides, plant growth regulators and fertilizers. Chemicals which may be used in admixture include compounds cited in the *Pesticide Manual* (13$^{th}$ edition, published by The British Crop Protection Council) and the *Shibuya Index* (13$^{th}$ edition, 2008, published by the Shibuya Index Research Group). Specific examples of insecticides, acaricides and nematicides include organophosphate compounds such as acephate, dichlorvos, EPN, fenitothion, fenamifos, prothiofos, profenofos, pyraclofos, chlorpyrifos-methyl, diazinon, fosthiazate and imicyafos; carbamate compounds such as methomyl, thiodicarb, aldicarb, oxamyl, propoxur, carbaryl, fenobucarb, ethiofencarb, fenothiocarb, pirimicarb, carbofuran and benfuracarb; nereistoxin derivatives such as cartap and thiocyclam; organochlorine compounds such as dicofol and tetradifon; pyrethroid compounds such as permethrin, tefluthrin, cypermethrin, deltamethrin, cyhalothrin, fenvalerate, fluvalinate, ethofenprox and silafluofen; benzoyl urea compounds such as diflubenzuron, teflubenzuron, flufenoxuron and chlorfluazuron; juvenile hormone-like compounds such as methoprene; and molting hormone-like compounds such as chromafenozide. Examples of other compounds include buprofezin, hexythiazox, amitraz, chlordimeform, pyridaben, fenpyroxymate, pyrimidifen, tebufenpyrad, tolfenpyrad, fluacrypyrim, acequinocyl, cyflumetofen, flubendizmide, ethiprole, fipronil, ethoxazle, imidacloprid, clothianidin, thiamethoxam, acetamiprid, nitenpyram, thiazcloprid, dinotefuran, pymetrozine, bifenazate, spirodiclofen, spiromesifen, flonicamid, chlorfenapyr, pyriproxyfen, indoxacarb, pyridalyl, spinosad, avermectin, milbemycin, cyneopyrafen, spinetoram, pyrifluquinazon, chlorantraniliprole, cyantraniliprole, spirotetramat, lepimectin, metafluminzone, pyrafluprole, pyriprole, hydramethylnon, triazamate, sulfoxaflor, flupyradifurone, flometoquin, organometallic compounds, dinitro compounds, organosulfur compounds, urea compounds, triazine compounds and hydrazine compounds.

The pest control agents of the invention may also be used in admixture or concomitantly with microbial pesticides such as BT formulations and entomopathogenic virus formulations.

Examples of fungicides which may be used in admixture or concomitantly include strobilurin compounds such as azoxystrobin, kresoxym-methyl, trifloxystrobin, metominostrobin and orysastrobin; anilinopyrimidine compounds such as mepanipyrim, pyrimethanil and cyprodinil; azole compounds such as triadimefon, bitertanol, triflumizole, metoconazole, propiconazole, penconazole, flusilazole, myclobutanil, cyproconazole, tebuconazole, hexaconazole, prochloraz and simeconazole; quinoxaline compounds such as quinomethionate; dithiocarbamate compounds such as maneb, zineb, mancozeb, polycarbamate and propineb; phenylcarbamate compounds such as diethofencarb; organochlorine compounds such as chlorothalonil and quintozene; benzimidazole compounds such as benomyl, thiophanate-methyl and carbendazole; phenylamide compounds such as metalaxyl, oxadixyl, ofurase, benalaxyl, furalaxyl and cyprofuram; sulfenic acid compounds such as dichlofluanid; copper compounds such as copper hydroxide and oxine-copper; isoxazole compounds such as hydroxyisoxazole; organophosphorus compounds such as fosetyl-aluminum and tolclofos-methyl; N-halogenothioalkyl compounds such as captan, captafol and folpet; dicarboxyimide compounds such as procymidone, iprodione and vinchlozolin; carboxyanilide compounds such as flutolanil, mepronil, furamepyr, thifluzamide, boscalid and penthiopyrad; morpholine compounds such as fenpropimorph and dimethomorph; organotin compounds such as fenthin hydroxide and fenthin acetate; cyanopyrrole compounds such as fludioxonil and fenpiclonil; and also tricyclazole, pyroquilon, carpropamid, diclocymet, fenoxanil, fthalide, fluazinam, cymoxanil, triforine, pyrifenox, fenarimol, fenpropidin, pencycuron, ferimzone, cyazofamid, iprovalicarb, benthiavalicarb-isopropyl, iminoctadin-albesilate, cyflufenamid, kasugamycin, validamycin, streptomycin, oxolinic acid, tebufloquin, probenazole, tiadinil and isotianil.

Methods for Synthesizing the Compounds of the Invention (1) Compounds of chemical formula (Ia) below

[Chem. 7]

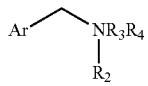

(Ia)

(wherein Ar is a phenyl group which may be substituted, or a 5- or 6-membered heterocycle which may be substituted; $R_2$ is a $C_{1-6}$ alkylcarbonyl group in which the alkyl moiety may be substituted with a halogen atom, a $C_{1-6}$ alkyloxycarbonyl group in which the alkyl moiety may be substituted with a halogen atom, a $C_{1-6}$ alkylsulfonyl group in which the alkyl moiety may be substituted with a halogen atom, $CONR_6R_7$ (wherein $R_6$ and $R_7$ are each independently a hydrogen atom or a $C_{1-6}$ alkyl group which may be substituted with a halogen), a $C_{1-6}$ O,O'-alkylphosphoryl group in which the alkyl moiety may be substituted with a halogen atom, a cyano group, a formyl group or a nitro group; $R_3$ is a $C_{1-8}$ alkylene group which may be substituted with a halogen atom, a $C_{2-8}$ alkenylene group which may be substituted with a halogen atom, a $C_{2-8}$ alkynylene group which may be substituted with a halogen atom, a phenylene group which may be substituted, or a 5- or 6-membered heterocyclic divalent group which may be substituted; and $R_4$ is a hydrogen atom, a phenyl group which may be substituted, a 3- to 8-membered carbocycle or heterocycle which may be substituted, a halogen atom, $OR_5$, $OCOR_5$, $OCOOR_5$, $COR_5$, $COOR_5$, $SR_5$, $SOR_5$, $SO_2R_5$ (wherein $R_5$ is a $C_{1-6}$ alkyl group, an aryl group or an aralkyl group, any of which may be substituted with a halogen), N—CO—$OR_8$, N—CO—$SR_8$, N—CS—$OR_8$, N—CS—$SR_8$, N—O—CO—$R_8$, O—CO—$R_8$, O—CO—$OR_8$, O—CO—$SR_8$, O—CS—$OR_8$, O—CS—$SR_8$, S—CS—$OR_8$, S—CS—$SR_8$, S—CO—$OR_8$, S—CO—$SR_8$ (wherein $R_8$ is a $C_{1-6}$ alkyl group which may be substituted, the substituent being a halogen, a $C_{1-4}$ alkyloxycarbonyl group, a $C_{1-4}$ alkylcarbonyl group, a benzoyl group which may be substituted with a halogen or a $C_{1-4}$ alkyl group which may be substituted with a halogen, a $C_{1-4}$ alkyloxy group or a $C_{1-4}$ alkylthio group), or $NR_9R_{10}$ (wherein $R_9$ and $R_{10}$ are each independently a hydrogen atom, a $C_{1-6}$ alkyl group which may be substituted with a halogen, a $C_{1-6}$ alkylcarbonyl group in which the alkyl moiety may be substituted with a halogen atom, or a $C_{1-6}$ alkylcarbonyloxy group in which the alkyl moiety may be substituted with a halogen atom);

with the proviso that when Ar is a 2,6-dichloro-4-pyridyl group, $R_2$ is not a $C_{1-6}$ alkyloxycarbonyl group in which the alkyl moiety may be substituted with a halogen atom) may be obtained by reacting, for example, a halide, anhydride or ester of $R_2$ ($R_2$ having the same meaning as defined in above chemical formula (I)) with a compound of the following chemical formula (II)

[Chem. 8]

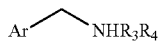

(II)

(wherein Ar, $R_3$ and $R_4$ have the same meanings as defined in above chemical formula (I)), either in the presence or absence of a base.

Carboxylic acid halides, carboalkyloxy halides, sulfonyl halides, O,O'-alkylphosphoryl halides, carboxylic anhydrides, dialkyldicarbonates, carboxylic acid esters and carbonic acid esters may be used as the halide, anhydride or ester of $R_2$. For example, the use of acetyl chloride, ethyl chloroformate, methanesulfonyl chloride, diethyl chlorophosphate, trifluoroacetic anhydride or ethyl formate is preferred.

When the reaction is carried out in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of dimethylformamide, acetonitrile, ethers, dichloromethane, chloroform or the like is preferred.

The reaction may generally be carried out at from −80 to 100° C., and is preferably carried out in the range of 20 to 50° C.

When $R_2$ in the above chemical compound (Ia) is a $C_{1-6}$ alkylcarbonyl group in which the alkyl moiety may be substituted with a halogen atom, the compound of formula (Ia) may be obtained by reacting the compound of chemical formula (II) with a carboxylic acid of the formula $R_{2'}$—COOH (wherein $R_{2'}$ is a $C_{1-6}$ alkyl group which may be substituted with a halogen atom) in the presence of a dehydration-condensation agent.

A carbodiimide compound such as dicyclohexylcarbodiimide or 1-ethyl-3-(3-dimethylaminopropyl)carbodiimide hydrochloride may be used as the dehydration-condensation agent.

The reaction is preferably carried out using a solvent. For example, amides such as dimethylformamide and dimethylacetamide, nitriles such as acetonitrile, sulfoxides such as dimethylsulfoxide, ethers such as diethyl ether and tetrahydrofuran, esters such as ethyl acetate and butyl acetate, aromatic hydrocarbons such as benzene, xylene and toluene, ketones such as acetone and methyl ethyl ketone, aliphatic hydrocarbons such as hexane, heptane and octane, and halogenated hydrocarbons such as dichloromethane, chloroform, chlorobenzene and dichlorobenzene may be used singly or as combinations of two or more thereof. The use of, for example, dichloromethane or chloroform is preferred.

The reaction may be carried out at generally from −80 to 100° C., and is preferably carried out in the range of 20 to 50° C.

When $R_2$ in above chemical formula (Ia) is a cyano group, the compound of formula (Ia) may be obtained by reacting the compound of formula (II) with a known cyanating reagent, either in the presence or absence of a base.

Cyanating reagents that may be used for this purpose include cyanogen bromide, cyanogen iodide, 1-cyanoimidazole, 1-cyanobenzotriazole, and substituted or unsubstituted benzenesulfonyl cyanide.

When the reaction is carried out in the presence of a base, the base may be, for example, an alkali metal hydride such as sodium hydride, a carbonate such as potassium carbonate or sodium carbonate, an alkali metal acetate such as sodium acetate, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of an ether such as diethyl ether or tetrahydrofuran, or a halogenated hydrocarbon such as dichloromethane or chloroform is preferred. The reaction may be carried out at generally from 0 to 100° C., although it is preferable to add the cyanating reagent at 0° C. and gradually raise the temperature to about 20 to 50° C.

The compound of chemical formula (II) may be synthesized from a compound of chemical formula (IIIa) or chemical formula (IIIb) below:

[Chem. 9]

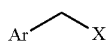
(IIIa)

(wherein X is a halogen, OTs or Oms)

[Chem. 10]

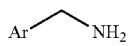
(IIIb)

(wherein Ar has the same meaning as defined in above chemical formula (I)).

When synthesis is carried out from the compound of formula (IIIa), the compound of formula (II) may be obtained by reacting the compound of formula (IIIa) with a compound of the chemical formula (IVa) below

[Chem. 11]

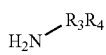
(IVa)

(wherein $R_3$ and $R_4$ have the same meanings as defined above in chemical formula (I)), either in the presence or absence of a base.

When the reaction is carried in the presence of a base, the base used for this purpose may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), or halogenated hydrocarbons (e.g., dichloromethane, chloroform, chlorobenzene, dichlorobenzene) may be used singly or as combinations of two or more thereof. The use of dimethylformamide, acetonitrile, an ether, dichloromethane or chloroform is preferred.

The reaction may be carried out at generally from 0 to 200° C., although it is preferable to add the reagent at 0° C., gradually raise the temperature to about 20 to 50° C., then let the temperature rise to a higher temperature as the reaction proceeds.

The amount of the compound of formula (IIIa) added is preferably not more than one mole per mole of the compound of formula (IVa).

In the case of synthesis from the compound of formula (IIIb), the compound of formula (II) may be obtained by reacting a compound of the following chemical formula (IVb) with the compound of formula (IIIb)

[Chem. 12]

(IVb)

(wherein $R_3$ and $R_4$ have the same meanings as defined in above chemical formula (I), and X is a halogen atom, OTs or OMs), either in the presence or absence of a base.

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of dimethylformamide, acetonitrile, an ether, dichloromethane or chloroform is preferred.

The reaction may be carried out at generally from 0 to 200° C., although it is preferable to add the reagent at 0° C., gradually raise the temperature to about 20 to 50° C., then let the temperature rise to a higher temperature as the reaction proceeds.

The amount of the compound of formula (IVb) added is preferably not more than one mole per mole of the compound of formula (IIIb).

Alternatively, the compound of formula (II) may be obtained by adding a compound of the formula (IVc) below, either in the presence or absence of an acid, to the compound of formula (IIIb) so as to form an imine, then carrying out a reducing reaction.

[Chem. 13]

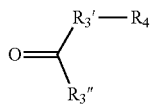

(IVc)

(In the formula, $R_{3'}$ and $R_{3''}$, which may be the same or different, are each independently a hydrogen atom or a $C_{1-7}$ alkyl group, and $R_{3'}$ and $R_{3''}$ may together form a ring, with the provisos that $R_{3'}$ and $R_{3''}$ are not both hydrogen atoms and that the sum of the numbers of carbon atoms on $R_{3'}$ and $R_{3''}$ is smaller than 7; and $R_4$ has the same meaning as defined in above chemical formula (I).)

It is preferable to use a solvent in the reaction. Illustrative examples of solvents that may be used include lower alcohols (e.g., methanol, ethanol), acetonitrile, dichloromethane and dichloroethane, with the use of methanol or ethanol being preferred.

In cases where an acid is used, the acid may be, for example, hydrochloric acid, a substituted or unsubstituted benzenesulfonic acid, or acetic acid.

The reducing reaction may be carried out using a hydride reducing reagent such as sodium borohydride, sodium cyanoborohydride or sodium triacetoxyborohydride.

Alternatively, the reducing reaction may be carried out by a catalytic hydrogenation reaction using a metal catalyst. Metal catalysts that may be used include palladium, platinum rhodium, nickel and iron.

The reaction may be carried out at generally from 20 to 100° C.

(2) Compounds of the formula (Ia) may be synthesized from compounds of the following chemical formula (Va)

[Chem. 14]

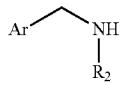

(Va)

(wherein Ar and $R_2$ have the same meanings as defined in above chemical formula (Ia).)

A compound of formula (Ia) can be obtained by reacting a compound of formula (Va) with a compound of the formula $X$—$R_3R_4$ (wherein $R_3$ and $R_4$ have the same meanings as defined in above chemical formula (I), and X is a halogen atom), either in the presence or absence of a base.

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine. The use of an alkali metal hydride such as sodium hydride is preferred.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of dimethylformamide, acetonitrile, an ether, dichloromethane or chloroform is preferred.

A compound of formula (Va) can be obtained by reacting a halide, anhydride, ester or the like of formula $R_2$ (wherein $R_2$ has the same meaning as defined in above chemical compound (I)) with a compound of formula (IIIb), either in the presence or absence of a base.

The halide, anhydride, ester or the like of formula $R_2$ which is used may be, for example, a carboxylic acid halide, a carboalkyloxy halide, a sulfonyl halide, a O,O'-alkylphosphoryl halide, a carboxylic anhydride, a dialkyl dicarbonate, a carboxylic acid ester, a carbonic acid ester or a cyanohalide.

The reaction is preferably carried out using a solvent, in which case solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of an ether such as diethyl ether or tetrahydrofuran is preferred.

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

A compound of formula (Va) can be obtained by reacting a compound of formula $R_2$—$NH_2$ (wherein $R_2$ has the same meaning as defined in above chemical compound (I)) with a compound of formula (IIIa), either in the presence or absence of a base.

The use of a solvent in the reaction is preferred, in which case solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of acetonitrile or the like is preferred.

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

(3) Compounds of the formula (Ia) may also be synthesized from compounds of the following chemical formula (Vb)

[Chem. 15]

(Vb)

(wherein $R_2$, $R_3$ and $R_4$ have the same meanings as defined in above chemical formula (I)).

Compounds of the formula (Ia) can be obtained by reacting a compound of the formula (Vb) with a compound of the formula Ar—CH$_2$—X (wherein Ar has the same meaning as defined in above chemical formula (I), and X is a halogen atom, OTs or OMs), either in the presence or absence of a base.

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine. The use of an alkali metal hydride such as sodium hydride is preferred.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of dimethylformamide, acetonitrile, an ether, dichloromethane or chloroform is preferred.

The compound of formula (Vb) may be obtained by reacting a halide, anhydride, ester or the like of the formula $R_2$ (wherein $R_2$ has the same meaning as defined in above chemical formula (I)) with a compound of the formula (IVa), either in the presence or absence of a base.

Examples of halides, anhydrides and esters of the formula $R_2$ that may be used include carboxylic acid halides, carboalkyloxy halides, sulfonyl halides, O,O'-alkylphosphoryl halides, carboxylic anhydrides, dialkyloxy dicarbonates, carboxylic acid esters, carbonic acid esters and cyanogen halides.

The use of a solvent in the reaction is preferred. Solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of an ether such as diethyl ether or tetrahydrofuran is preferred.

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

Alternatively, the compound of formula (Vb) can be obtained by reacting a compound of the formula $R_2$—NH$_2$ (wherein $R_2$ has the same meaning as defined in above chemical compound (I)) with a compound of the formula X—$R_3R_4$ (wherein $R_3$ and $R_4$ have the same meanings as defined in above chemical formula (I), and X is a halogen atom), either in the presence or absence of a base.

The use of a solvent in the reaction is preferred. Solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of acetonitrile or tetrahydrofuran is preferred.

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

(4) Compounds of the chemical formula (Ib) below can be obtained by reacting a compound of the formula ArCH$_2$X (wherein X is a halogen atom) with a compound of the formula $R_2$NH$_2$ (wherein $R_2$ has the same meaning as defined in above chemical compound (I)), either in the presence or absence of a base.

[Chem. 16]

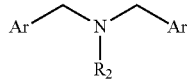

(Ib)

(In the formula, Ar and $R_2$ have the same meanings as defined in above chemical formula (I).)

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), or halogenated hydrocarbons (e.g., dichloromethane, chloroform, chlorobenzene, dichlorobenzene) may be used singly or as combinations of two or more thereof. The use of acetonitrile is preferred.

The reaction may be carried out at generally from 0 to 200° C., although it is preferable to add the reagent at 20 to 40° C., and to carry out the reaction at 60 to 80° C.

(5) Compounds of the following chemical formula (Ic)

[Chem. 17]

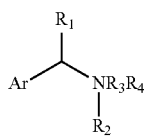

(Ic)

(wherein $R_1$ is a $C_{1-6}$ alkyl group, and Ar, $R_2$, $R_3$ and $R_4$ having the same meanings as defined in above chemical formula (I)) can be obtained by reacting a halide, anhydride, ester or the like of the formula $R_2$ ($R_2$ having the same meaning as defined in above chemical formula (I)) with a compound of the formula (VIa) below, either in the presence or absence of a base.

[Chem. 18]

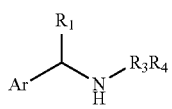

(VIa)

(In the formula, $R_1$ is a $C_{1-6}$ alkyl group, and Ar, $R_3$ and $R_4$ have the same meanings as defined in above chemical formula (I).)

Examples of halides, anhydrides and esters of the formula $R_2$ which may be used include carboxylic acid halides, carboalkyloxy halides, sulfonyl halides, O,O'-alkylphosphoryl halides, carboxylic anhydrides, dialkyl dicarbonates, carboxylic acid esters and carbonic acid esters. The use of, for example, acetyl chloride, ethyl chloroformate, methanesulfonyl chloride, diethyl chlorophosphate, trifluoroacetic anhydride or ethyl formate is preferred.

When the reaction is carried in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of dimethylformamide, acetonitrile, ethers, dichloromethane or chloroform is preferred.

The reaction may be carried out at generally from −80 to 100° C., although it is preferable to carry out the reaction in the range of 20 to 50° C.

When the alkyl moiety of $R_2$ in the compound of formula (Ic) is a $C_{1-6}$ alkyl carbonyl group which may be substituted with a halogen atom, the compound of formula (Ic) can be obtained by reacting a carboxylic acid of the formula $R_{2'}$—COOH (wherein $R_{2'}$ is a $C_{1-6}$ alkyl group which may be substituted with a halogen atom) with a compound of the formula (VIa) in the presence of a dehydration-condensation agent.

A carbodiimide compound such as dicyclohexylcarbodiimide or 1-ethyl-3-(3-dimethylaminopropyl)carbodiimide hydrochloride may be used as the dehydration-condensation agent.

The reaction is preferably carried out using a solvent. Solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), ketones (e.g., acetone, methyl ethyl ketone), aliphatic hydrocarbons (e.g., hexane, heptane, octane), or halogenated hydrocarbons (e.g., dichloromethane, chloroform, chlorobenzene, dichlorobenzene) may be used singly or as combinations of two or more thereof. The use of dichloromethane or chloroform is preferred.

The reaction may be carried out at generally from −80 to 100° C., although it is preferable to carry out the reaction in the range of 20 to 50° C.

When $R_2$ in the compound of formula (Ic) is a cyano group, the compound of formula (Ic) may be obtained by reacting a known cyanating reagent with the compound of formula (IVa), either in the presence or absence of a base.

Cyanating reagents which may be used for this purpose include cyanogen bromide, cyanogen iodide, 1-cyanoimidazole, 1-cyanobenzotriazole, and substituted and unsubstituted benzenesulfonyl cyanide.

When the reaction is carried out in the presence of a base, the base used for this purpose may be, for example, an alkali metal hydride such as sodium hydride, a carbonate such as potassium carbonate or sodium carbonate, an alkali metal acetate such as sodium acetate, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of an ether such as diethyl ether or tetrahydrofuran, or a halogenated hydrocarbon such as dichloromethane and chloroform is preferred.

The reaction may be carried out at generally from 0 to 100° C., although it is preferable to add the cyanating reagent at 0° C. and gradually raise the temperature to about 20 to 50° C.

The compound of formula (VIa) can be obtained by adding a compound of the formula $H_2N$—$R_3R_4$ (wherein $R_3$ and $R_4$ have the same meanings as defined in chemical formula (I)) to a compound of the following chemical formula (VII)

[Chem. 19]

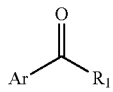

(VII)

(wherein $R_1$ is the same as above) in the presence or absence of an acid so as to form an imine, then carrying out a reducing reaction.

The reaction is preferably carried out using a solvent. It is preferable to use a lower alcohol such as methanol or ethanol, or dichloromethane or chloroform as the solvent, although the use of acetonitrile is also possible.

When an acid is used, the acid may be, for example, hydrochloride acid, a substituted or unsubstituted benzenesulfonic acid, or acetic acid.

The reducing reaction may be carried out using a hydride reducing reagent such as sodium borohydride, sodium cyanoborohydride or sodium triacetoxyborohydride.

The reducing reaction may be carried out by a catalyst hydrogenation reaction using a metal catalyst. Metal catalysts that may be used include palladium, platinum, rhodium, nickel and iron.

The reaction may be carried out at a temperature in the range of generally from 20 to 100° C.

(6) Compounds of the following chemical formula (Id)

[Chem. 20]

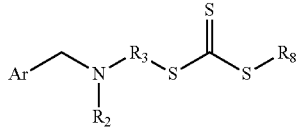

(Id)

(wherein Ar, $R_2$ and $R_8$ have the same meanings as defined in above chemical formula (I)) can be obtained by reacting carbon disulfide and a compound of the formula $R_8$—X (wherein $R_8$ has the same meaning as defined in above chemical formula (I), and X is a halogen atom), in the presence of a base, with a compound of the chemical formula (VIII) below that can be synthesized by a method described in the literature (*Journal of Medicinal Chemistry* 42(12), 2227-2234 (1999)).

[Chem. 21]

(VIII)

(In the formula, Ar has the same meaning as defined in above chemical formula (I).)

The base used for this purpose may be, for example, an alkali metal hydride such as sodium hydride, a carbonate such as potassium carbonate or copper carbonate, an alkali metal hydroxide such as potassium hydroxide or sodium hydroxide, a metal oxide such as copper oxide or magnesium oxide, a tertiary amine such as triethylamine, or a substituted or unsubstituted pyridine compound such as pyridine or 4-dimethylaminopyridine. The use of a strong base such as potassium t-butylate is preferred.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of an ether such as tetrahydrofuran is preferred.

The reaction may be carried out at generally from −80 to 100° C., although it is preferable to carry out the reaction in the range of 20 to 50° C.

A compound of the chemical formula (Ie)

[Chem. 22]

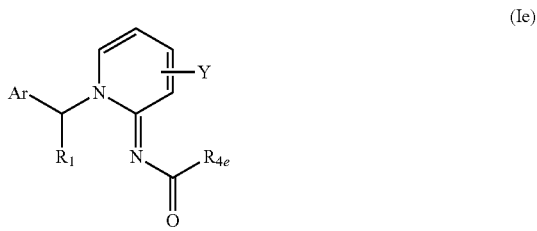

(Ie)

(wherein Ar, $R_1$, Y and $R_{4e}$ are the same as defined above) can be obtained by reacting a compound of the formula (IX) below with a compound of the formula ArCH($R_1$)X (wherein Ar and $R_1$ are the same as defined above, and X is a halogen, OTs or OMs), in the presence or absence of a base.

[Chem. 23]

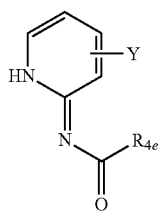

(IX)

(In the reaction, Y and $R_{4e}$ are the same as defined above.)

When the reaction is carried out in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), or halogenated hydrocarbons (e.g., dichloromethane, chloroform, chlorobenzene, dichlorobenzene) may be used singly or as combinations of two or more thereof. The use of acetonitrile is preferred.

The reaction may be carried out at generally from 0 to 200° C., although it is preferable to add the reagent at 20 to 40° C., and carry out the reaction at 60 to 80° C.

Compounds of the above chemical formula (IX) can be obtained by reacting a compound of the formula $R_{4e}$—C(=O)X, $R_{4e}$—C(=O)OC(=O)$R_{4e}$ or $R_{4e}$C(=O)OR' (wherein X is a halogen atom, OTS or OMs; R' is a $C_{1-6}$ alkyl group; and $R_{4e}$ is as defined above) with a compound of the formula (IXa) below, either in the presence or absence of a base.

[Chem. 24]

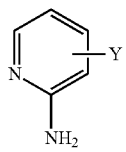

(IXa)

(In the formula, Y is as defined above.)

When the reaction is carried out in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of dimethylformamide, acetonitrile, ethers, dichloromethane or chloroform is preferred.

The reaction may be carried out at generally from −80 to 100° C., although it is preferable to carry out the reaction in the range of 20 to 50° C.

The compound of above formula (IX) may also be obtained by reacting a compound of above formula (IXa) with a carboxylic acid of the formula $R_{4e}$—COON (wherein $R_{4e}$ is the same as defined above) using a dehydration-condensation agent, either in the presence or absence of a base.

A carbodiimide compound such as dicyclohexylcarbodiimide or 1-ethyl-3-(3-dimethylaminopropyl)carbodiimide hydrochloride may be used as the dehydration-condensation agent.

When the reaction is carried out in the presence of a base, the base may be, for example, a carbonate such as potassium carbonate or sodium carbonate, a tertiary amine such as triethylamine, or a substituted or unsubstituted pyridine compound such as pyridine or 4-dimethylaminopyridine.

The reaction is preferably carried out using a solvent. For example, amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), ketones (e.g., acetone, methyl ethyl ketone), aliphatic hydrocarbons (e.g., hexane, heptane, octane), or halogenated hydrocarbons (e.g., dichloromethane, chloroform, chlorobenzene, dichlorobenzene) may be used singly or as combinations of two or more thereof. The use of dichloromethane or chloroform is preferred.

The reaction may be carried out at generally from −80 to 100° C., although it is preferable to carry out the reaction in the range of 20 to 50° C.

Compounds of above formula (Ie) can be obtained by reacting a compound of the formula $R_{4e}$—C(=O)X, $R_{4e}$—C(=O)OC(=O)$R_{4e}$ or R4e-C(=O)OR' (wherein X is a halogen atom, R' is a $C_{1-6}$ alkyl group, and $R_{4e}$ is as defined above) with a compound of the formula (IXb) below or a salt thereof, in the presence or absence of a base.

[Chem. 25]

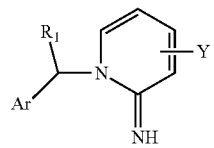

(IXb)

(In the formula, Ar, $R_1$ and Y are as defined above.)

When the reaction is carried out in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of dimethylformamide, acetonitrile, ethers, dichloromethane or chloroform is preferred.

The reaction may be carried out at generally from −80 to 100° C., although it is preferable to carry out the reaction in the range of 20 to 50° C.

Compounds of above formula (Ie) may also be obtained by reacting a compound of the above formula (IXb) or a salt thereof with a carboxylic acid of the formula $R_{4e}$—COON (wherein $R_{4e}$ is as defined above) using a dehydration-condensation agent, either in the presence or absence of a base.

A carbodiimide compound such as dicyclohexylcarbodiimide or 1-ethyl-3-(3-dimethylaminopropyl)carbodiimide hydrochloride may be used as the dehydration-condensation agent.

When the reaction is carried out in the presence of a base, the base may be, for example, a carbonate such as potassium carbonate or sodium carbonate, a tertiary amine such as triethylamine, or a substituted or unsubstituted pyridine compound such as pyridine or 4-dimethylaminopyridine.

The reaction is preferably carried out using a solvent. For example, amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), ketones (e.g., acetone, methyl ethyl ketone), aliphatic hydrocarbons (e.g., hexane, heptane, octane), or halogenated hydrocarbons (e.g., dichloromethane, chloroform, chlorobenzene, dichlorobenzene) may be used singly or as combinations of two or more thereof. The use of dichloromethane or chloroform is preferred.

The reaction may be carried out at generally from −80 to 100° C., although it is preferable to carry out the reaction in the range of 20 to 50° C.

Compounds of the above formula (IXb) can be obtained by reacting a compound of above formula (IXa) with a compound of the formula ArCH($R_1$)X (wherein Ar, $R_1$ and X are as defined above), in the presence or absence of a base.

When the reaction is carried out in the presence of a base, the base may be, for example, an alkali metal hydride such as sodium hydride, a carbonate such as potassium carbonate or sodium carbonate, an alkali metal hydroxide such as potassium hydroxide or sodium hydroxide, a tertiary amine such as triethylamine, or a substituted or unsubstituted pyridine compound such as pyridine or 4-dimethylaminopyridine.

The reaction may be carried out in the absence of a solvent or using a solvent which does not affect the reaction. In cases where a solvent is used, solvents such as amides (e.g., dimethylformamide, dimethylacetamide), nitriles (e.g., acetonitrile), sulfoxides (e.g., dimethylsulfoxide), ethers (e.g., diethyl ether, tetrahydrofuran), esters (e.g., ethyl acetate, butyl acetate), aromatic hydrocarbons (e.g., benzene, xylene, toluene), alcohols (e.g., methanol, ethanol, propanol), ketones (e.g., acetone, methyl ethyl ketone), aliphatic hydrocarbons (e.g., hexane, heptane, octane), halogenated hydrocarbons (e.g., dichloromethane, chloroform, chlorobenzene, dichlorobenzene), or water may be used singly or as combinations of two or more thereof. The use of dimethylformamide, acetonitrile, ethers, dichloromethane or chloroform is preferred.

The reaction may be carried out at generally from −80 to 100° C., although it is preferable to carry out the reaction in the range of 20 to 50° C.

In cases where (Ie) is synthesized via (IX) from a compound of chemical formula (IXa), or in cases where (Ie) is synthesized via (IXb) from a compound of chemical formula (IXa), the reactions may be carried out consecutively without removing the (IX) or (IXb), or the reactions from (IXa) to (Ie) may be allowed to proceed simultaneously within the same reaction vessel.

EXAMPLES

Next, the invention is described more fully below by way of working examples, although the invention is not limited by the working examples.

Reference Example 1: 2-chloro-5-[N-(2-methylthioethyl)]aminomethylpyridine (Compound 23)

2-methylthioethylamine (3.0 g, 33 mmol) was dissolved in 25 mL of anhydrous dimethylformamide, following which 5.3 g (33 mmol) of 2-chloro-5-chloromethylpyridine, 1.6 g of 60% sodium hydride (net weight, 950 mg; 40 mmol) were added in this order, and stirring at 70° C. was carried out for 90 minutes. The reaction mixture was cooled to 0° C. and the reaction was brought to completion by adding about 30 mL of water a little at a time, after which the reaction mixture was extracted twice with about 50 mL of dichloromethane. The dichloromethane phase was dried over anhydrous magnesium sulfate, concentrated, and subsequently purified by silica gel column chromatography (hexane/ethyl acetate=1:1-4→ethyl acetate→dichloromethane/methanol=1:19-4→dichloromethane/methanol=1:10), giving 4.6 g of the target compound (yield, 64%).

Synthesis Example 1: 2-chloro-5-[N-cyano-N-(2-methylthioethyl)]aminomethylpyridine (Compound 1)

Anhydrous diethyl ether, 4 mL, was added to 123 mg (1.16 mmol) of cyanogen bromide, and the mixture was cooled to 0° C. To this were added, in order, 250 mg (1.16 mmol) of 2-chloro-5-[N-(2-methylthioethyl)]aminomethylpyridine (Reference Example 1) dissolved in 3 mL of anhydrous diethyl ether, and 95 mg (1.16 mmol) of sodium acetate, following which the system was stirred overnight at room temperature. Next, about 10 mL of a 1% aqueous solution of sodium hydroxide was added to the reaction mixture and the mixture was stirred for 1 hour, following which about 20 mL of diethyl ether was added and liquid-liquid extraction was carried out. The diethyl ether phase was washed with, in order, about 10 mL of water and about 10 mL of 1% hydrochloric acid, then dried over anhydrous magnesium sulfate and concentrated under reduced pressure, giving 209 mg of the target compound (yield, 75%).

Synthesis Example 2: 2-chloro-5-[N-formyl-N-(2-methylthioethyl)]aminomethylpyridine (Compound 29)

Ethyl formate (10 mL) was added to 132 mg (0.61 mmol) of 2-chloro-5-[N-(2-methylthio)ethyl]aminomethylpyridine (Reference Example 1), and the system was refluxed for 3 hours. Once the reaction mixture had returned to room temperature, the solvent was distilled off under reduced pressure, and purification was carried out with silica gel column chromatography (hexane/ethyl acetate=7:3→4 1:1), giving 159 mg of the target compound (yield, 81%).

Synthesis Example 3: 2-chloro-5-[N-trifluoroacetyl-N-ethyl]aminomethylpyridine (Compound 21)

A solution of 140 mg (0.67 mmol) of trifluoroacetic anhydride dissolved in 5 mL of anhydrous dichloromethane was added dropwise under ice cooling to a solution of 120 mg (0.70 mmol) of ethyl-(2-chloro-5-pyridylmethyl)amine synthesized by the method described in U.S. Patent Application Publication No. 2009306041 and 101 mg (1 mmol) of triethylamine dissolved in 5 mL of anhydrous dichloromethane. Following dropwise addition, the system was stirred overnight at room temperature, then the reaction mixture was washed with, in order, ice-cooled 1% aqueous sodium hydroxide, water, 1% hydrochloric acid, then water, and subsequently dried over anhydrous magnesium sulfate. The solvent was distilled off under reduced pressure, giving 107 mg the target compound (yield, 78%).

Synthesis Example 4: 2-chloro-5-(N-cyano-N-2-isopropyl)aminomethylpyridine (Compound 15)

Acetone (2 mL) and 1 mL of methanol were added to 50 mg (0.26 mmol) of 2-chloro-5-aminoethylpyridine, 43 mg (0.52 mmol) of sodium acetate was added, and the mixture was stirred at room temperature for 4 hours. Next, 30 mg (0.78 mmol) of sodium borohydride was added, and the mixture was stirred at room temperature for 1 hour. The reaction mixture was filtered and then concentrated, after which ethyl acetate and water were added and liquid-liquid extraction was carried out. The organic phase was dried over anhydrous magnesium sulfate, then concentrated and subsequently purified on a preparative TLC plate, giving 17 mg of 2-chloro-5-[N-(2-isopropylaminomethyl)]pyridine (yield, 36%).

Using 57 mg of the resulting 2-chloro-5-[N-(2-isopropylaminomethyl)]pyridine, 54 mg of the target compound (yield, 47%) was obtained by the method described in Synthesis Example 1.

Synthesis Example 5: 2-chloro-5-[N-cyano-N-(2-propargyl)]aminomethylpyridine (Compound 42)

2-chloro-5-aminoethylpyridine (1.50 g, 10.6 mmol) was dissolved in 10 mL of anhydrous dimethylformamide, then 486 mg (net weight, 292 mg; 12.7 mmol) of 60% sodium hydride and 1.25 g (10.6 mmol) of propargyl bromide were added in this order, and stirring was carried out at 70° C. for 3.5 hours. The reaction mixture was returned to room temperature and the reaction was stopped by slowly adding water, after which the reaction mixture was extracted with ethyl acetate. The ethyl acetate phase was dried over anhydrous magnesium sulfate and subsequently concentrated, then purified by silica gel column chromatography (hexane/ethyl acetate=1:1), giving 892 mg of 2-chloro-5-[N-(2-propargyl)]aminomethylpyridine (yield, 47%).

Using 60 mg of the resulting 2-chloro-5-[N-(2-propargyl)]aminomethylpyridine, 20 mg of the target compound (yield, 30%) was obtained by the method described in Synthesis Example 1.

Synthesis Example 6: 2-chloro-5-[N-cyano-N-(6-chloro-3-pyridylmethyl)]aminomethylpyridine (Compound 17)

6-chloro-3-chloromethylpyridine (648 mg, 4 mmol), 50% aqueous ammonium cyanide solution (100 mg), and potassium carbonate (590 mg, 5 mmol) were suspended in acetonitrile (20 mL), and the mixture was refluxed under heating for 40 hours. The condensate was filtered while hot, the filtrate was concentrated, and the residue was washed with ether and water. The viscous mixture was recrystallized from a small amount of methanol, giving 28 mg of the target compound.

$^1$H-NMR (CDCl$_3$, δ, ppm): 4.17 (4H, s), 7.40 (2H, d), 7.68 (2H, dd), 8.31 (2H, d)

IR: 2207 (CN)

MS: m/z=293 (M+H)

Synthesis Example 7: 4-chloro-[N-cyano-N-(4-chlorobenzyl)]aminomethylbenzene (Compound 55)

The target compound was obtained in an amount of 450 mg (yield, 15%) from 1.61 g of 4-chlorobenzyl chloride by the same method as in Synthesis Example 6.

$^1$H-NMR (CDCl$_3$, δ, ppm): 4.10 (2H, s), 7.23 (2H, d), 7.36 (2H, d)

MS: m/z=291 (M+H)

Synthesis Example 8: N-[1-(6-chloro-3-pyridyl)ethyl]-N-cyanoethylamino (Compound 18)

6-chloro-3-acetylpyridine (1.03 g, 0.3 mmol) and a 30% ethylamine-methanol solution (1.0 mL) were mixed with 8 mL of chloroform, and the mixture was subjected to refluxing. After 8 hours, 1 mL of 30% ethylamine-methanol solution was added and stirring was continued for 12 hours at the same temperature. The chloroform was distilled off and the residue was dissolved in 10 mL of methanol, then ice-cooled. Sodium borohydride (1 g) was added a little at a time, and the system was stirred overnight. The methanol was distilled off, and the residue was extracted with acetonitrile. The extract was then concentrated under reduced pressure. Acetonitrile extraction and concentration under reduced pressure were each repeated another two times, following which the residue was dissolved in chloroform, washed with 1% aqueous NaOH, and the chloroform phase was dried over solid KOH. The chloroform was distilled off under reduced pressure, giving 790 mg of crude N-[1-(6-chloro-3-pyridyl)ethyl]-N-ethylamine product (purity, 80%).

Using 100 mg of the crude N-[1-(6-chloro-3-pyridyl)ethyl]-N-ethylamine thus obtained, 55 mg (yield, 60%) of the target product was obtained by the method described in Synthesis Example 1.

¹H-NMR (CDCl₃, δ, ppm): 1.25 (3H, t), 1.66 (3H, d), 2.91 (2H, m), 4.14 (1H, q), 7.37 (1H, d), 7.73 (1H, dd), 8.30 (1H, d) IR: 2211 (CN), 2206 (CN)

Synthesis Example 9: 2-[N-(6-chloro-3-pyridylmethyl)cyanamide]ethyl methylcarbonotrithioate (Compound 6)

Potassium t-butylate (112 mg, 1 mmol) was added to a solution of (6-chloro-3-pyridylmethyl)-2-imino-1,3-thiazolidine (228 mg, 1 mmol), synthesized by a method described in the literature (*Journal of Medicinal Chemistry*, 42(12), 2227 (1999)), in 15 mL of tetrahydrofuran, and the mixture was stirred for 30 minutes at room temperature, following which 228 mg (3 mmol) of carbon disulfide was added a little at a time and stirring was continued for 1 hour. Methyl iodide (142 mg, 1 mmol) was added dropwise and the system was stirred for 2 hours. The insoluble solid was removed by filtration through Celite, and the filtrate was concentrated under reduced pressure. The target compound was isolated as a yellow oil from the viscous residue by silica gel column chromatography using ethyl acetate/hexane (1:1 volumetric ratio) as the developing solvent. The yield was 130 mg (41%).

¹H-NMR (CDCl₃, δ, ppm): 2.76 (3H, s), 3.31 (2H, t), 3.63 (2H, t), 4.28 (2H, s), 7.38 (1H, d), 7.73 (1H, dd), 8.35 (1H, d) IR: 2211 (CN)

Synthesis Example 10: 2-chloro-5-[N-trifluorosulfonyl-N-(2-propynyl)]aminomethylpyridine (Compound 152)

An amount of 104 mg (0.58 mmol) of 2-chloro-5-[N-(2-propynyl)]aminomethylpyridine obtained by the method described in Synthesis Example 5 was dissolved in 10 mL of anhydrous dichloromethane, 191 μL (1.16 mmol, 326 mg) of trifluorosulfonic anhydride was added, and the mixture was stirred at room temperature for 2 hours. After reaction completion, the reaction mixture was diluted by adding dichloromethane, then washed with, in order, a 1% aqueous sodium hydroxide solution and a 1% aqueous hydrochloric acid solution, and subsequently dried over anhydrous magnesium sulfate, concentrated under reduced pressure, and purified by silica gel column chromatography (hexane/ethyl acetate=2:8), giving 55 mg of the target compound (yield, 30%).

Synthesis Example 11: 2-chloro-5-[N-cyano-N-(cyclopropylmethyl)]aminomethylpyridine (Compound 71)

The N-[(6-chloropyridin-3-yl)methyl]cyanamide (30 mg, 0.18 mL) synthesized by the method in a comparative example was dissolved in 3 mL of anhydrous dimethylformamide, 10 mg of 60% sodium hydride (net weight, 6 mg; 0.26 mmol) was added, and the mixture was stirred at room temperature for minutes. Next, 52 μg (0.57 mmol) of (chloromethyl)cyclopropane and 5 mg of potassium iodide were added in this order, and the mixture was stirred at room temperature for 20 hours. Following reaction completion, the reaction was stopped by adding a small amount of water to the reaction mixture, and liquid-liquid extraction was carried out with 1% hydrochloric acid and ethyl acetate. The organic phase was washed with 1% hydrochloric acid, then dried over anhydrous magnesium sulfate, concentrated under reduced pressure, and purified on a preparative TLC plate (one 0.5 mm plate; developed with hexane/ethyl acetate=1:1, giving 18 mg of the target compound (yield, 45%).

Synthesis Example 12: 2-[N-(6-Chloro-3-pyridylmethyl)cyanamide]ethyl O-ethylcarbonodithioate (Compound 86)

1,2-bis(tosyloxy)ethane (8.86 g; 24.0 mmol) was dissolved in 100 mL of anhydrous dimethylformamide, following which 2.00 g (12.0 mmol) of N-[(6-chloropyridin-3-yl)methyl]cyanamide synthesized by the method in a comparative example, 500 mg of 60% NaH (net weight, 300 mg; 13.2 mmol) and 44 mg of KI were added in this order under ice cooling, and the system was stirred at room temperature for 80 minutes. Following reaction completion, methanol was added a little at a time at 0° C., then the reaction was stopped by adding water. Next, ethyl acetate and 1% hydrochloric acid were added to the system and liquid-liquid extraction was carried out. The organic phase was washed with 1% hydrochloric acid, dried over anhydrous magnesium sulfate and concentrated under reduced pressure, then purified by silica gel column chromatography (hexane/ethyl acetate=2:8→6:4). When the fractions containing the target compound were collected and concentrated, dimethylformamide remained in the concentrate. Hence, a small amount of ethyl acetate was added and the concentrate was washed twice with 1% hydrochloric acid, then dried over anhydrous magnesium sulfate and concentrated under reduced pressure to remove the dimethylformamide, giving 1.43 g of 2-[N-(6-chloro-3-pyridylmethyl)cyanamide]ethyl 4-methylbenzenesulfonate (Compound 84). The yield was 33%.

Anhydrous acetonitrile (3 mL) was added to 45 mg (0.28 mmol) of potassium ethyl xanthate, a solution of 50 mg (0.14 mmol) of 2-[N-(6-chloro-3-pyridylmethyl)cyanamide]ethyl 4-methylbenzenesulfonate synthesized by the above-described method dissolved in 2 mL of acetonitrile was added thereto, and the mixture was stirred at 50° C. for 50 minutes. Following reaction completion, the reaction mixture was concentrated under reduced pressure, ethyl acetate and 1% hydrochloric acid were added, and liquid-liquid extraction were carried out. The organic phase was dried over anhydrous magnesium sulfate, then concentrated under reduced pressure, purified on a preparative TLC plate (one 0.5 mm plate, liquid-liquid extraction with hexane/ethyl acetate=2:3), giving 23 mg of the target compound (yield, 18%).

Synthesis Example 13: 2-[N-(6-chloro-3-pyridylmethyl)cyanamide]ethyl benzyl(ethyl)carbamodithioate (Compound 85)

Benzyl ethyl amine (55 mg, 0.41 mmol) was dissolved in 5 mL of anhydrous tetrahydrofuran, 46 mg (0.41 mmol) of potassium t-butylate was added, and the mixture was stirred at room temperature for 20 minutes. Next, 49 μg (62 mg, 0.41 mmol) of carbon disulfide, 50 mg (0.14 mmol) of 2-[N-(6-chloro-3-pyridylmethyl)cyanamide]ethyl 4-methylbenzenesulfonate (Compound 84) synthesized by the method of Synthesis Example 12 dissolved in 3 mL of anhydrous tetrahydrofuran, and 5 mg of potassium iodide were added in this order, and the system was stirred at 40° C. for 1 hour. Following reaction completion, a small amount of water was added to stop the reaction, the reaction mixture was filtered using Celite, and the filtrate was concentrated. The concentrate was purified by silica gel column chromatography (hexane/ethyl acetate=7:3), giving 41 mg of the target compound (yield, 72%).

Tables 6 to 9 below present spectral data on the compounds obtained in Synthesis Examples 1 to 13 and on other compounds obtained by similar methods.

In the tables, the synthesis methods are referred to as follows.

A: Methods similar to those used in Synthesis Examples 1 to 5 and 10

B: Methods similar to those used in Synthesis Examples 6 and 7

C: Methods similar to that used in Synthesis Example 8

D: Methods similar to that used in Synthesis Example 9

E: Methods similar to that used in Synthesis Example 11

F: Methods similar to those used in Synthesis Examples 12 and 13

TABLE 6

| Compound No. | Synthesis Method | $^1$H-NMR (CDCl$_3$, δ, ppm) | IR (KBr, v, cm$^{-1}$) or MS |
|---|---|---|---|
| 1 | A | 2.40 (3H, s), 2.89 (2H, s), 3.35 (2H, s), 4.27 (2H, s), 7.40 (1H, d), 7.75 (1H, dd), 8.36 (1H, d) | 2211 (CN) |
| 2 | A | 1.32 (3H, t), 2.68 (2H, q), 2.87 (2H, t), 3.34 (2H, t), 4.27 (2H, s), 7.41 (1H, d), 7.74 (1H, dd), 8.37 (1H, d) | 2211 (CN) |
| 3 | A | 0.99 (3H, t), 1.69 (2H, m), 2.65 (2H, t), 2.86 (2H, t), 3.34 (2H, t), 4.27 (2H, s), 7.40 (1H, d), 7.74 (1H, dd), 8.36 (1H, d) | 2211 (CN) |
| 4 | A | 0.97 (3H, t), 1.69 (2H, m), 2.92 (2H, t), 4.19 (2H, s), 7.39 (1H, d), 7.71 (1H, dd), 8.33 (1H, d) | 2209 (CN) |
| 5 | A | 1.96 (2H, m), 2.11 (3H, s), 2.58 (2H, t), 3.11 (2H, t), 4.21 (2H, s), 7.39 (1H, d), 7.71 (1H, dd), 8.35 (1H, d) | 2210 (CN) |
| 6 | E | 2.76 (3H, s), 3.31 (2H, t), 3.63 (2H, t), 4.28 (2H, s), 7.38 (1H, d), 7.73 (1H, dd), 8.35 (1H, d) | 2211 (CN), m/z = 318 (M + H) |
| 7 | E | 1.36 (3H, t), 3.30 (2H, t), 3.36 (2H, q), 3.61 (2H, t), 4.27 (2H, s), 7.39 (1H, d), 7.73 (1H, dd), 8.36 (1H, d) | m/z = 332 (M + H) |
| 8 | E | 1.02 (3H, t), 1.73 (2H, m), 3.30 (2H, t), 3.34 (2H, t), 3.61 (2H, t), 4.27 (2H, s), 7.38 (1H, s), 7.73 (1H, dd), 8.36 (1H, d) | m/z = 346 (M + H) |
| 9 | E | 1.37 (3H, t), 2.33 (2H, t), 3.38 (2H, q), 4.42 (2H, s), 7.51 (1H, s) | 2213 (CN), m/z = 338 (M + H) |
| 10 | E | 1.03 (3H, t), 1.75 (2H, q), 3.32 (2H, t), 3.36 (2H, t), 3.62 (2H, t), 4.42 (2H, s), 7.51 (1H, s) | 2214 (CN), m/z = 352 (M + H) |
| 11 | A | 3.19 (2H, t), 3.38 (3H, s), 3.61 (2H, t), 4.30 (2H, s), 7.38 (1H, d), 7.72 (1H, dd), 8.35 (1H, d) | 2212 (CN) |
| 12 | A | 0.93 (3H, t), 1.39 (2H, m), 1.65 (2H, m), 2.96 (2H, t), 4.19 (2H, s), 7.38 (1H, d), 7.71 (1H, dd), 8.33 (1H, d) | 2210 (CN) |
| 13 | A | 2.83 (3H, s), 4.17 (2H, s), 7.41 (1H, d), 7.71 (1H, dd), 8.34 (1H, d) | 2208 (CN) |
| 14 | A | 1.30 (3H, t), 3.03 (2H, q), 4.20 (2H, s), 7.39 (1H, d), 7.71 (1H, dd), 8.34 (1H, d) | 2210 (CN) |
| 15 | A | 1.29 (6H, d), 3.15 (1H, sept), 4.20 (2H, s), 7.39 (1H, d), 7.70 (1H, dd), 8.34 (1H, d) | 2210 (CN) |
| 16 | A | 2.23 (6H, s), 2.54 (2H, t), 3.06 (2H, t), 4.26 (2H, s), 7.37 (1H, d), 7.73 (1H, dd), 8.34 (1H, d) | 2211 (CN) |
| 17 | B | 1.66 (1H, m), 1.82 (2H, m), 2.20 (1H, m), 3.03 (1H, m), 3.17 (1H, m), 4.13 (1H, t), 7.22 (1H, m), 7.68 (1H, d), 8.45 (1H, d), 8.57 (1H, s) | 2207 (CN) |
| 18 | C | 1.24 (3H, t), 1.65 (3H, d), 2.91 (2H, m), 4.13 (1H, q), 7.36 (1H, d), 7.72 (1H, dd), 8.30 (1H, d) | 2206 (CN) |
| 19 | A | 1.28 (3H, t), 3.03 (2H, q), 4.32 (2H, s), 7.47 (1H, s) | 2213 (CN) |
| 20 | A | 1.12, 1.17 (3H, t), 2.12, 2.17 (3H, s), 3.29, 3.41 (2H, q), 4.53, 4.55 (2H, s), 7.29, 7.35 (1H, d), 7.41, 7.63 (2H, dd), 8.27 (1H, d) | 1635 (C=O) |
| 21 | A | 1.13, 1.26 (3H, t), 3.36, 3.44 (2H, q), 4.60, 4.61 (2H, s), 7.31, 7.38 (1H, d), 7.54, 7.61 (1H, dd), 8.28, 8.30 (1H, d) | 1691 (C=O) |
| 22 | A | 1.10 (3H, m), 3.25 (2H, m), 3.74 (3H, m), 4.44 (2H, m), 7.29 (1H, m), 7.58 (1H, m), 8.28 (1H, m) | 1702 (C=O) |
| 24 | A | 2.12, 2.13 (3H, s), 2.14, 2.21 (3H, s), 2.62, 2.67 (2H, t), 3.46, 3.54 (2H, t), 4.60, 4.63 (2H, s), 7.30, 7.36 (1H, d), 7.51, 7.63 (1H, dd), 8.27 (1H, d) | m/z = 259 (M + H) |
| 25 | A | 2.12, 2.13 (3H, s), 2.72 (3H, t), 3.57, 3.58 (3H, t), 4.58, 4.69 (2H, s), 7.07-7.43 (6H, m), 7.68 (1H, dd), 8.37 (1H, d) | m/z = 337 (M + H) |
| 26 | A | 1.98 (3H, s), 2.44 (2H, t), 3.29 (2H, t), 4.37 (2H, s), 7.33 (1H, d), 7.56 (2H, dd), 7.63 (1H, td), 7.74 (1H, dd), 7.84 (2H, dd), 8.23 (1H, d) | m/z = 357 (M + H) |
| 27 | A | 2.10 (3H, s), 2.63 (2H, m), 3.43 (2H, m), 3.76 (3H, m), 4.52 (2H, s), 7.30 (1H, m), 7.60 (1H, m), 8.30 (1H, m) | m/z = 275 (M + H) |
| 28 | A | 2.07 (3H, s), 2.58 (2H, t), 3.01 (3H, s), 3.38 (2H, t), 4.42 (2H, s), 7.36 (1H, d), 7.80 (1H, dd), 8.34 (1H, d) | m/z = 295 (M + H) |
| 29 | A | 2.09, 2.10 (3H, s), 2.57, 2.61 (2H, t), 3.37, 3.42 (2H, t), 4.52, 4.55 (2H, s), 7.32, 7.37 (1H, d), 7.56, 7.64 (1H, dd), 8.31, 8.32 (1H, d) | m/z = 245 (M + H) |
| 30 | A | 1.80 (3H, m), 2.60 (2H, m), 3.50 (2H, m), 4.74 (2H, m), 7.32 (1H, d), 7.42 (5H, m), 7.53, 7.68 (1H, dd), 8.16 (1H, d) | m/z = 321 (M + H) |
| 31 | A | 2.11, 2.13 (3H, s), 2.67 (2H, t), 3.50, 3.58 (2H, t), 4.67, 4.74 (2H, s), 7.34, 7.38 (1H, d), 7.55, 7.62 (1H, dd), 8.30, 8.32 (1H, d) | m/z = 313 (M + H) |
| 33 | A | 1.33 (6H, t), 2.06 (3H, s), 2.56 (2H, t), 3.09 (2H, m), 4.08 (4H, m), 4.26 (2H, m), 7.32 (1H, d), 7.72 (1H, dd), 8.33 (1H, d) | m/z = 353 (M + H) |
| 34 | A | 2.13 (3H, s), 2.90 (2H, t), 3.14 (2H, t), 4.19 (2H, s), 7.44 (1H, d), 8.17 (1H, dd), 8.47 (1H, d) | m/z = 361 (M + H) |
| 35 | A | 1.26 (3H, t), 2.98 (2H, q), 4.19 (2H, s), 7.35 (5H, m) | m/z = 161 (M + H) |
| 36 | A | 1.29 (3H, t), 3.02 (2H, q), 4.22 (2H, s), 7.36 (1H, dd), 7.73 (1H, dd), 8.56 (1H, d), 8.62 (1H, dd) | m/z = 162 (M + H) |
| 37 | A | 1.27 (3H, t), 3.00 (2H, q), 4.16 (2H, s), 7.27 (2H, d), 7.35 (2H, d) | m/z = 195 (M + H) |
| 39 | A | 1.12 (3H, t × 2), 2.11, 2.18 (3H, s), 3.28, 3.43 (2H, t), 4.51, 4.59 (2H, s), 7.29 (5H, m) | |

TABLE 6-continued

| Compound No. | Synthesis Method | ¹H-NMR (CDCl₃, δ, ppm) | IR (KBr, v, cm⁻¹) or MS |
|---|---|---|---|
| 40 | A | 1.07 (3H, m), 3.25 (2H, m), 3.74 (3H, s), 4.47 (2H, s), 7.28 (5H, m) | |
| 41 | A | 1.25 (3H, t), 2.99 (2H, q), 4.20 (2H, s), 7.11 (1H, m), 7.25 (1H, m), 7.36 (1H, m) | m/z = 167 (M + H) |
| 42 | A | 2.54 (1H, t), 3.81 (2H, s), 4.30 (2H, s), 7.40 (1H, d), 7.73 (1H, dd), 8.39 (1H, d) | m/z = 206 (M + H) |
| 43 | A | 3.62 (2H, dd), 4.19 (2H, s), 5.37 (2H, dd × 2), 5.85 (1H, tdd), 7.39 (1H, d), 7.71 (1H, dd), 8.33 (1H, d) | m/z = 208 (M + H) |
| 44 | A | 4.10 (2H, s), 4.17 (2H, s), 7.33 (6H, m), 7.65 (1H, dd), 8.23 (1H, d) | m/z = 258 (M + H) |
| 45 | A | 1.32 (3H, t), 3.03 (2H, q), 4.23 (2H, s), 7.53 (1H, m), 7.64 (3H, m) | m/z = 186 (M + H) |
| 46 | A | 1.32 (3H, t), 3.06 (2H, q), 4.31 (2H, s), 7.75 (1H, d), 7.93 (1H, dd), 8.68 (1H, d) | m/z = 230 (M + H) |
| 47 | A | 2.14 (3H, s), 2.78 (2H, t), 3.25 (2H, t), 4.38 (2H, s), 7.76 (1H, d), 7.97 (1H, dd), 8.72 (1H, d) | m/z = 276 (M + H) |

TABLE 7

| Compound No. | Synthesis Method | ¹H-NMR (CDCl₃, δ, ppm) | IR (KBr, v, cm⁻¹) or MS |
|---|---|---|---|
| 48 | A | 1.26 (3H, t), 2.56 (2H, m), 2.81 (2H, q), 3.24 (2H, t), 4.38 (2H, s), 7.75 (1H, d), 7.96 (1H, d), 8.71 (1H, s) | m/z = 290 (M + H) |
| 49 | A | 2.75 (2H, t), 3.05 (2H, t), 3.73 (2H, s), 4.20 (2H, s), 6.18 (1H, d), 6.31 (1H, dd), 7.35 (1H, d), 7.38 (1H, d), 7.71 (1H, dd), 8.31 (1H, d) | m/z = 308 (M + H) |
| 50 | A | 2.65 (2H, t), 2.99 (2H, t), 3.72 (2H, s), 4.11 (2H, s), 7.30 (6H, m), 7.64 (1H, dd), 8.26 (1H, d) | m/z = 318 (M + H) |
| 51 | A | 3.44 (2H, m), 3.48 (2H, m), 4.23 (2H, s), 7.37 (1H, d), 7.61 (2H, m), 7.70 (2H, m), 7.91 (2H, m), 8.33 (1H, d) | m/z = 336 (M + H) |
| 52 | A | 3.12 (2H, td), 3.17 (2H, td), 4.18 (2H, s), 7.31 (6H, m), 7.68 (1H, dd), 8.25 (1H, m) | m/z = 304 (M + H) |
| 53 | A | 3.43 (2H, t), 4.19 (2H, t), 4.35 (2H, s), 6.88 (2H, d), 7.02 (1H, m), 7.31 (3H, m), 7.72 (1H, dd), 8.36 (1H, d) | m/z = 288 (M + H) |
| 54 | A | 2.01 (3H, s), 3.17 (2H, t), 3.50 (2H, q), 4.24 (2H, s), 5.92 (1H, brs), 7.39 (1H, d), 7.69 (1H, dd), 8.36 (1H, d) | m/z = 253 (M + H) |
| 55 | B | 4.08 (4H, s), 7.23 (4H, d), 7.36 (4H, d) | m/z = 291 (M + H) |
| 57 | E | 2.96 (2H, t), 3.20 (2H, t), 4.07 (2H, s), 7.17 (2H, m), 7.29 (4H, m), 7.48 (1H, dd), 8.18 (1H, d) | m/z = 272 (M + H) |
| 58 | E | 3.43 (2H, t), 4.98 (2H, s), 4.53 (2H, t), 7.33 (1H, d), 7.47 (1H, m), 7.60 (1H, m), 7.71 (1H, dd), 8.03 (2H, m), 8.35 (1H, d) | m/z = 316 (M + H) |
| 59 | E | 3.98 (2H, s), 4.36 (2H, s), 7.45 (1H, d), 7.74 (1H, dd), 8.42 (1H, d) | m/z = 207 (M + H) |
| 61 | E | 2.11 (3H, s), 3.28 (2H, t), 4.27 (4H, m), 7.40 (1H, d), 7.71 (1H, dd), 8.36 (1H, d) | m/z = 254 (M + H) |
| 62 | E | 2.25 (3H, s), 4.17 (2H, s), 4.33 (2H, s), 7.39 (1H, d), 7.72 (1H, dd), 8.37 (1H, d) | m/z = 228 (M + H) |
| 68 | E | 2.21 (1H, dd), 2.58 (1H, dd), 3.08 (2H, m), 3.32 (1H, dd), 4.31 (2H, dd), 7.39 (1H, d), 7.72 (1H, dd), 8.36 (1H, d) | |
| 69 | E | 2.60 (1H, dd), 2.88 (2H, m), 3.21 (1H, m), 3.49 (1H, dd), 4.31 (2H, s), 7.38 (1H, d), 7.74 (1H, dd), 8.39 (1H, d) | |
| 70 | E | 2.70 (2H, t), 3.30 (2H, t), 3.73 (3H, s), 4.25 (2H, s), 7.38 (1H, d), 7.72 (1H, dd), 8.35 (1H, d) | |
| 71 | E | 0.27 (2H, m), 0/66 (2H, m), 1.06 (1H, m), 2.88 (2H, d), 4.26 (2H, s), 7.40 (1H, d), 7.75 (1H, dd), 8.34 (1H, d) | m/z = 222 (M + H) |
| 72 | A | 2.14 (3H, s), 2.77 (2H, t), 3.23 (2H, t), 4.28 (2H, s), 7.87 (1H, d), 8.28 (1H, d) | m/z = 276 (M + H) |
| 73 | C | 1.69 (3H, d), 2.90 (3H, s), 2.77 (2H, m), 3.08 (2H, m), 4.23 (1H, q), 7.38 (1H, d), 7.76 (1H, dd), 8.33 (1H, d) | m/z = 256 (M + H) |
| 74 | A | 2.15 (3H, s), 2.75 (2H, t), 3.23 (2H, t), 4.24 (2H, s), 7.51 (1H, s) | m/z = 248 (M + H) |
| 75 | A | 1.27 (3H, t), 2.58 (2H, q), 2.78 (2H, t), 3.21 (2H, t), 4.42 (2H, s), 7.51 (1H, s) | m/z = 262 (M + H) |
| 76 | A | 2.22 (2H, m), 2.92 (4H, m), 3.63 (1H, m), 4.26 (2H, s), 7.39 (1H, d), 7.73 (1H, dd), 8.36 (1H, d), | m/z = 254 (M + H) |
| 77 | A | 1.36 (3H, d), 2.11 (3H, d), 2.62 (1H, dd), 2.79 (1H, dd), 3.15 (1H, m), 4.29 (1H, d), 4.32 (1H, d), 7.38 (1H, d), 7.76 (1H, dd), 8.37 (1H, d) | m/z = 256 (M + H) |
| 78 | A | 2.11 (3H, s), 2.75 (2H, t), 3.21 (2H, t), 4.27 (2H, s), 7.00 (1H, dd), 7.89 (1H, td), 8.19 (1H, d) | m/z = 226 (M + H) |
| 79 | A | 2.14 (3H, s), 2.78 (2H, t), 3.23 (2H, t), 4.30 (2H, s), 7.59 (1H, dd), 8.21 (1H, s) | m/z = 260 (M + H) |
| 80 | A | 1.30 (3H, t), 3.01 (2H, q), 4.21 (2H, s), 7.54 (1H, d), 8.19 (1H, s) | m/z = 214 (M + H) |
| 81 | A | 3.60, 3.68, 3.70 (2H, dt × 2), 4.60, 4.69 (2H, t × 2), 4.77, 4.78 (2H, s × 2), 7.33, 7.39 (1H, d × 2), 7.55, 7.63 (1H, dd × 2), 8.30, 8.33 (1H, d × 2) | m/z = 285 (M + H) |
| 82 | A | 3.30 (2H, dt), 4.31 (2H, s), 4.31-4.73 (2H, m), 7.39 (1H, d), 7.73 (1H, dd), 8.36 (1H, d) | m/z = 214 (M + H) |
| 83 | E | 4.18 (2H, s), 4.32 (2H, s), 7.40 (1H, d), 7.48 (1H, s) 7.69 (1H, dd), 8.33 (1H, d) | m/z = 299 (M + H) |
| 84 | E | 2.47 (3H, s), 3.31 (2H, t), 4.21 (2H, t), 4.23 (2H, s), 7.37 (3H, m), 7.68 (1H, dd), 7.79 (2H, d), 8.30 (1H, d) | m/z = 366 (M + H) |
| 85 | F | 1.22 (3H, t × 2), 3.36 (2H, t × 2), 3.60 (2H, t × 2), 3.71 (2H, q), 4.02 (2H, q), 4.28, 4.32 (2H, s × 2), 4.94, 5.31 (2H, s × 2), 7.32 (6H, m), 7.74 (1H, dd), 8.38 (1H, m) | m/z = 405 (M + H) |
| 86 | F | 1.42 (3H, t), 3.31 (2H, t), 3.38 (2H, t), 4.28 (2H, s), 4.63 (2H, q), 7.38 (1H, d), 7.72 (1H, dd), 8.37 (1H, d) | m/z = 316 (M + H) |
| 88 | F | 3.25, 3.47 (3H, s × 2), 3.36 (2H, t × 2), 3.60 (2H, t × 2), 4.29, 4.32 (2H, s × 2), 4.98, 5.33 (2H, s × 2), 7.18-7.37 (6H, m), 7.73 (2H, m), 8.41 (1H, m) | m/z = 391 (M + H) |
| 89 | C | 1.74 (3H, m), 3.19 (1H, m), 3.37-3.82 (1H, m), 4.31-4.66 (2H, m), 5.33 (1H, m), 7.37 (1H, d × 2), 7.57, 7.70 (1H, dd × 2), 8.35, 8.38 (1H, d × 2) | m/z = 299 (M + H) |
| 90 | F | 1.39 (6H, d), 3.30-3.40 (4H, m), 5.73 (1H, m), 7.38 (1H, d), 7.73 (1H, dd), 8.37 (1H, d) | m/z = 330 (M + H) |

TABLE 7-continued

| Compound No. | Synthesis Method | ¹H-NMR (CDCl₃, δ, ppm) | IR (KBr, v, cm⁻¹) or MS |
|---|---|---|---|
| 91 | F | 0.92 (3H, t), 1.37 (4H, m), 1.79 (2H, m), 3.31 (2H, t), 3.38 (2H, t), 4.29 (2H, s), 4.57 (2H, t), 7.38 (1H, d), 7.73 (1H, dd), 8.37 (1H, d) | m/z = 358 (M + H) |
| 92 | C | 1.70 (3H, d), 3.22 (2H, m), 4.29 (1H, q), 4.64 (2H, m), 7.39 (1H, d), 7.74 (1H, dd), 8.33 (1H, d) | m/z = 228 (M + H) |
| 93 | F | 1.00 (3H, t), 1.38 (2H, m), 3.31 (2H, t), 3.38 (2H, t), 4.29 (2H, s), 4.53 (2H, t), 7.38 (1H, d), 7.73 (1H, dd), 8.37 (1H, d) | m/z = 330 (M + H) |
| 94 | F | 0.96 (3H, t), 1.41 (2H, m), 1.80 (2H, m), 3.31 (2H, t), 3.38 (2H, t), 4.28 (2H, s), 4.58 (2H, t), 7.38 (1H, d), 7.73 (1H, dd), 8.36 (1H, d) | m/z = 344 (M + H) |
| 95 | A | 3.68, 3.76 (2H, td × 2), 4.78, 4.88 (2H, s × 2), 5.85-6.15 (1H, m), 7.52, 7.56 (1H, s × 2) | m/z = 309 (M + H) |
| 96 | C | 1.73 (3H, d), 3.16, 3.49 (2H, m × 2), 5.27, 5.37 (1H, q × 2), 7.33, 7.40 (1H, d × 2), 7.56, 7.70 (1H, d × 2), 8.36 (1H, m) | m/z = 317 (M + H) |
| 97 | A | 3.60, 3.71 (2H, td × 2), 4.79 (2H, s), 5.85-6.18 (1H, m), 7.36, 7.40 (1H, d × 2), 7.53, 7.60 (1H, dd × 2), 8.30, 8.36 (1H, d × 2) | m/z = 303 (M + H) |

TABLE 8

| Compound No. | Synthesis Method | ¹H-NMR (CDCl₃, δ, ppm) | IR (KBr, v, cm⁻¹) or MS |
|---|---|---|---|
| 98 | F | 3.59, 3.87 (2H, td × 2), 4.76, 4.85 (2H, s × 2), 5.86-6.17 (1H, m), 7.37, 7.41 (1H, d × 2), 7.55, 7.62 (1H, d × 2), 8.31, 8.32 (1H, s × 2) | m/z = 319 (M + H) |
| 99 | A | 3.59 (2H, m), 5.11 (2H, m), 6.10 (1H, m), 7.37 (1H, d), 7.60 (1H, d), 8.32 (1H, s) | m/z = 351 (M + H) |
| 100 | F | 2.03 (2H, m), 2.47 (3H, s), 3.09 (2H, t), 4.12 (2H, t), 4.18 (2H, s), 7.38 (3H, m), 7.70 (1H, dd), 7.78 (1H, d), 8.33 (1H, d) | m/z = 380 (M + H) |
| 101 | F | 1.43 (3H, t), 2.10 (2H, m), 3.10 (2H, t), 3.20 (2H, t), 4.21 (2H, s), 4.66 (2H, q), 7.39 (1H, d), 7.71 (1H, dd), 8.34 (1H, d) | m/z = 330 (M + H) |
| 102 | F | 1.00 (2H, t), 1.83 (2H, q), 2.11 (2H, q), 3.09 (2H, t), 3.19 (2H, t), 4.21 (2H, s), 4.55 (2H, t), 7.38 (1H, d), 7.71 (1H, dd), 8.34 (1H, d) | m/z = 344 (M + H) |
| 103 | F | 1.25 (3H, m), 2.12 (2H, m), 3.06, 3.12 (2H, t × 2), 3.36, 3.40 (2H, t × 2), 3.71, 4.05 (2H, q × 2), 4.19, 4.23 (2H, s × 2), 4.94, 5.33 (2H, s × 2), 7.33 (7H, m), 7.72 (1H, m), 8.33 (1H, m) | m/z = 419 (M + H) |
| 104 | A | 3.58 (2H, m), 4.67 (2H, m), 5.77-6.07 (1H, m), 7.41 (1H, d), 7.72 (1H, dd), 8.37 (1H, d) | |
| 105 | C | 1.01, 1.17 (3H, t × 2), 1.72 (3H, d × 2), 3.02-3.54 (2H, m), 5.28, 5.38 (1H, q × 2), 7.34, 7.38 (1H, d × 2), 7.57, 7.66 (1H, dd × 2), 8.37 (1H, m) | m/z = 281 (M + H) |
| 107 | C | 1.02 (3H, t), 1.72 (3H, d), 3.28 (2H, m), 5.26 (1H, q), 7.37 (1H, d), 7.77 (1H, d), 8.44 (1H, d) | m/z = 317 (M + H) |
| 108 | C | 1.70, 1.75 (3H, d × 2), 3.16-3.58 (2H, m), 5.30 (1H, q), 5.61-5.96 (1H, m), 7.38, 7.41 (1H, d × 2), 7.73 (1H, dd), 8.41, 8.44 (1H, d × 2) | m/z = 353 (M + H) |
| 109 | C | 1.01 (3H, m), 2.03, 2.24 (2H, m × 2), 3.32, 3.72 (2H, m × 2), 5.03 (1H, q), 5.60-6.20 (1H, m), 7.37, 7.41 (1H, d × 2), 7.60, 7.76 (1H, dd × 2), 8.39 (1H, m) | m/z = 331 (M + H) |
| 110 | C | 0.97 (3H, t), 2.04-2.32 (2H, m), 3.30-3.60 (2H, m), 5.72-6.00 (1H, m), 7.41 (1H, d), 7.72 (1H, m), 8.44 (1H, s) | m/z = 367 (M + H) |
| 111 | C | 1.02 (3H, m), 2.00-2.30 (2H, m), 3.14-3.38 (2H, m), 4.94-5.12 (1H, m), 7.26-7.34 (1H, m), 7.60-7.76 (1H, m), 8.38 (1H, m) | m/z = 295 (M + H) |
| 112 | C | 0.98, 1.05 (3H, t), 2.06, 2.24 (2H, m × 2), 3.32 (2H, m), 4.90 (1H, q), 7.38 (1H, d), 7.75 (1H, m), 8.45 (1H, s) | m/z = 331 (M + H) |
| 114 | C | 1.03 (3H, t), 1.78 (3H, d), 3.20-3.45 (2H, m), 5.32 (1H, q), 7.73 (1H, d), 7.98 (1H, d), 8.82 (1H, s) | m/z = 351 (M + H) |
| 115 | C | 1.03, 1.23 (3H, t × 2), 1.78 (3H, d × 2), 3.00-3.60 (2H, m), 5.34 (1H, q), 7.69. 7.73 (1H, d × 2), 7.80. 7.88 (1H, d × 2), 8.70, 8.71 (1H, d × 2) | m/z = 315 (M + H) |
| 119 | E | 3.63 (2H, d), 4.33 (2H, s), 5.38 (2H, m), 5.83 (1H, m), 7.47 (1H, s) | m/z = 214 (M + H) |
| 120 | E | 2.55 (1H, t), 3.83 (2H, d), 4.46 (2H, s), 7.55 (1H, s) | m/z = 212 (M + H) |
| 121 | E | 2.86 (3H, s), 4.31 (2H, s), 7.50 (1H, s) | m/z = 188 (M + H) |
| 122 | E | 0.98 (3H, t), 1.69 (2H, m), 2.95 (2H, t), 4.33 (2H, s), 7.49 (1H, s) | m/z = 216 (M + H) |
| 124 | C | 0.95 (3H, m), 1.73 (3H, d), 3.47 (2H, m), 5.22 (1H, m), 7.25 (2H, m), 7.71 (1H, td), 8.58 (1H, d) | m/z = 283 (M + H) |
| 128 | A | 2.50 (1H, t), 4.23 (2H, m), 4.71 (2H, m), 7.41 (1H, d), 7.75 (1H, dd), 8.41 (1H, d) | m/z = 313 (M + H) |
| 129 | A | 3.96 (2H, m), 4.55 (2H, m), 7.44 (1H, d), 7.74 (1H, dd), 8.44 (1H, d) | m/z = 314 (M + H) |
| 130 | A | 1.23 (3H, t × 2), 3.49 (2H, q × 2), 4.86 (2H, s × 2), 7.56 (1H, d × 2), 8.58 (1H, s × 2), 8.74 (1H, d × 2) | m/z = 301 (M + H) |
| 131 | A | 1.20 (3H, t), 3.42 (2H, m), 4.64 (2H, m), 7.74 (1H, d), 7.96 (1H, dd), 8.70 (1H, d) | m/z = 337 (M + H) |
| 132 | C | 1.04, 1.16, 1.31 (3H, t × 3), 1.70 (3H, d × 2), 2.90-3.58 (2H, m), 5.25, 5.40 (1H, q × 2), 7.22, 7.34 (2H, d × 2), 8.60, 8.65 (2H, d × 2) | m/z = 247 (M + H) |
| 133 | C | 0.97, 1.10 (3H, t × 2), 1.73 (3H, d), 3.07-3.52 (2H, m), 5.32, 5.52 (1H, q × 2), 7.34 (1H, m), 7.62, 7.70 (1H, d × 2), 8.56, 8.60 (1H, d × 2) | m/z = 247 (M + H) |
| 134 | C | 0.92, 1.08 (3H, t × 2), 1.71 (3H, d), 3.18-3.58 (2H, m), 5.28, 5.53 (1H, q × 2), 7.20-7.36 (2H, m), 7.69 (1H, m), 8.57, 8.62 (1H, d × 2) | m/z = 247 (M + H) |
| 135 | A | 2.94 (3H, s), 4.52 (2H, m), 7.39 (1H, d), 7.71 (1H, dd), 8.34 (1H, d) | m/z = 289 (M + H) |
| 136 | E | 2.47 (1H, s), 3.33 (3H, s), 4.22 (2H, t), 4.39 (2H, s), 7.38 (1H, d), 7.48 (1H, s), 7.81 (2H, s) | m/z = 372 (M + H) |
| 137 | F | 1.43 (3H, t), 3.37 (4H, m), 4.43 (2H, s), 4.67 (2H, q), 7.51 (1H, s) | m/z = 322 (M + H) |
| 138 | F | 1.26 (3H, t), 3.40 (2H, t × 2), 3.60 (2H, t × 2), 3.74, 4.06 (2H, q × 2), 4.43, 4.48 (2H, s × 2), 4.95, 5.30 (2H, s × 2), 7.20-7.40 (5H, m), 7.53, 7.56 (1H, s × 2) | m/z = 411.0286 (M + H) |
| 139 | A | 2.70 (3H, s), 2.97 (1H, m), 3.10 (1H, m), 3.51 (2H, m), 4.31 (2H, dd), 7.40 (1H, d), 7.76 (1H, dd), 8.40 (1H, d) | m/z = 258 (M + H) |
| 140 | A | 1.53 (6H, d), 4.24 (1H, m), 4.54 (2H, d), 7.35 (1H, d), 7.81 (1H, dd), 8.37 (1H, d) | m/z = 317 (M + H) |
| 141 | A | 0.83 (3H, t), 1.22 (2H, m), 1.55 (2H, m), 3.28 (2H, m), 4.61 (2H, m), 7.40 (1H, d), 7.74 (1H, dd), 8.34 (1H, d) | m/z = 331 (M + H) |
| 142 | A | 3.23 (2H, m), 3.70 (2H, m), 4.60 (2H, m), 7.24 (2H, m), 7.24-7.83 (7H, m), 8.32 (1H, d) | m/z = 443 (M + H) |

TABLE 8-continued

| Compound No. | Synthesis Method | ¹H-NMR (CDCl₃, δ, ppm) | IR (KBr, v, cm⁻¹) or MS |
|---|---|---|---|
| 143 | A | 3.70 (2H, m), 4.11 (2H, m), 4.74 (2H, m), 6.81 (2H, m), 7.26 (1H, d), 7.34 (3H, m), 7.75 (1H, d), 8.41 (1H, s) | m/z = 395 (M + H) |
| 144 | A | 1.16 (3H, t), 3.39 (2H, m), 4.74 (2H, m), 7.39 (1H, d), 7.75 (1H, dd), 8.35 (1H, d) | m/z = 303 (M + H) |
| 145 | A | 0.84 (3H, t), 1.53 (2H, m), 3.25 (2H, t), 4.55 (2H, m), 7.37 (1H, d), 7.76 (1H, dd), 8.32 (1H, d) | m/z = 317 (M + H) |
| 146 | A | 3.99 (2H, m), 4.72 (2H, m), 5.22 (1H, dd), 5.36 (1H, dd), 5.71 (1H, m), 7.39 (1H, d), 7.72 (1H, dd), 8.29 (1H, d) | m/z = 315 (M + H) |
| 147 | A | 4.44 (4H, m), 7.18 (2H, m), 7.25 (1H, d), 7.33 (2H, m), 7.53 (1H, dd), 8.03 (1H, d) | m/z = 365 (M + H) |
| 148 | A | 1.30 (3H, t), 3.05 (2H, q), 4.21 (2H, s), 7.00 (1H, dd), 7.86 (1H, td), 8.18 (1H, d) | m/z = 180 (M + H) |
| 149 | A | 1.29 (3H, t), 3.02 (2H, q), 4.18 (2H, s), 7.53 (1H, d), 7.61 (1H, dd), 8.32 (1H, d) | m/z = 240 (M + H) |

TABLE 9

| Compound No. | Synthesis Method | ¹H-NMR (CDCl₃, δ, ppm) | IR (KBr, v, cm⁻¹) or MS |
|---|---|---|---|
| 150 | A | 2.15 (6H, s), 3.36 (2H, t), 4.60 (4H, m), 7.38 (1H, d), 7.76 (1H, dd), 8.36 (1H, d) | m/z = 346 (M + H) |
| 151 | A | 1.04 (3H, t), 3.37 (2H, q), 4.52 (2H, s), 7.37 (1H, d), 7.80 (1H, dd), 8.32 (1H, d) | m/z = 401 (M + H) |
| 152 | A | 2.07 (1H, t), 2.43 (2H, m), 3.48 (2H, t),, 4.69 (2H, m), 7.40 (1H, d), 7.76 (1H, dd), 8.36 (1H, d) | m/z = 327 (M + H) |
| 153 | A | 1.32 (3H, t), 3.06 (2H, q), 4.21 (2H, s), 7.23 (1H, dd), 7.31 (1H, d), 8.42 (1H, d) | m/z = 196 (M + H) |
| 154 | A | 1.30 (3H, t), 3.14 (2H, q), 4.31 (2H, s), 7.30 (1H, d), 7.38 (1H, d), 7.72 (1H, d) | m/z = 196 (M + H) |
| 155 | A | 3.29 (3H, s), 3.45 (4H, m), 4.68 (2H, m), 7.36 (1H, d), 7.74 (1H, dd), 8.37 (1H, d) | m/z = 333 (M + H) |
| 157 | A | 1.17, 1.31 (3H t × 2), 3.48, 3.63 (2H, q × 2), 7.52 (1H, d), 7.60 (1H, d) | m/z = 268 (M + H) |
| 158 | A | 1.30 (3H, t), 3.01 (2H, q), 4.13 (2H, s), 7.23 (2H, s), 7.35 (1H, s) | m/z = 229 (M + H) |
| 159 | A | 2.58 (2H, m), 3.61 (2H, t), 4.52 (2H, s), 7.43 (1H, d), 7.78 (1H, dd), 8.41 (1H, d) | m/z = 328 (M + H) |
| 160 | A | 3.75 (3H, s), 3.94 (2H, m), 4.71 (2H, m), 7.39 (1H, d), 7.72 (1H, dd), 8.29 (1H, d) | m/z = 347 (M + H) |
| 161 | A | 4.03 (2H, m), 4.74 (2H, m), 7.40 (1H, d), 7.73 (1H, dd), 8.31 (1H, d) | m/z = 333 (M + H) |
| 163 | A | 4.26 (2H, m), 4.82 (2H, m), 7.63 (1H, s) | m/z = 320 (M + H) |
| 165 | A | 4.02 (2H, m), 4.84 (2H, m), 7.79 (1H, d), 8.00 (1H, dd), 8.78 (1H, d) | m/z = 348 (M + H) |
| 167 | A | 4.20 (2H, m), 4.64 (2H, m), 7.58 (1H, dd), 8.27 (1H, d) | m/z = 332 (M + H) |
| 170 | C | 1.90 (3H, d), 3.83 (1H, d), 4.27 (1H, d), 5.42 (1H, q), 7.43 (1H, d), 7.76 (1H, dd), 8.47 (1H, d) | m/z = 328 (M + H) |
| 171 | C | 1.86 (3H, d), 2.28 (1H, t), 3.78 (1H, d), 4.17 (1H, d), 5.34 (1H, q), 7.37 (1H, d), 7.78 (1H, d), 8.47 (1H, d) | m/z = 327 (M + H) |
| 172 | A | 2.51 (1H, t), 4.25 (2H, m), 4.81 (2H, m), 7.56 (1H, s) | m/z = 319 (M + H) |
| 176 | A | 1.62 (3H, t), 3.40 (2H, m), 4.03 (2H, m), 7.24 (1H, d), 7.36 (1H, d) | m/z = 335 (M) |
| 177 | A | 1.12 (3H, t), 3.36 (2H, m), 4.57 (2H, m), 7.38 (5H, m) | |
| 178 | A | 1.10 (3H, m), 3.31 (2H, m), 3.81 (2H, m), 4.43 (2H, s), 7.38 (1H, d), 7.78 (1H, dd), 8.33 (1H, d) | m/z = 317 (M + H) |
| 179 | A | 2.51 (1H, t), 3.97 (4H, m), 4.52 (2H, s), 7.37 (1H, d), 7.75 (1H, dd), 8.37 (1H, d) | m/z = 327 (M + H) |
| 180 | A | 1.14 (3H, t), 3.39 (2H, m), 4.50 (2H, m), 7.26 (2H, m), 7.34 (3H, m) | m/z = 301 (M) |
| 181 | A | 1.12 (3H, t), 3.36 (2H, m), 4.60 (2H, m), 7.30 (2H, d), 7.36 (2H, d) | m/z = 301 (M) |
| 182 | A | 1.15 (3H, t), 3.39 (2H, m), 4.50 (2H, m), 7.54 (1H, m), 7.67 (3H, m) | m/z = 292 (M) |
| 183 | A | 1.16 (3H, t), 3.42 (2H, m), 4.50 (2H, m), 7.54 (2H, d), 8.27 (2H, d) | m/z = 312 (M) |
| 184 | A | 2.50 (1H, t), 4.00 (2H, m), 4.65 (2H, m), 7.27 (2H, d), 7.38 (1H, m) | m/z = 345 (M) |
| 185 | A | 1.11 (3H, t), 2.36 (3H, t), 3.34 (2H, m), 4.49 (2H, m), 7.20 (2H, d), 7.24 (2H, d) | m/z = 281 (M) |
| 186 | A | 1.14 (3H, t), 3.39 (2H, m), 4.62 (2H, m), 7.48 (2H, d), 7.69 (2H, d) | m/z = 292 (M) |
| 187 | A | 1.11 (3H, t), 3.34 (2H, m), 3.82 (3H, s), 4.40 (2H, m), 6.88 (2H, d), 7.26 (2H, d) | m/z = 297 (M) |
| 188 | A | 1.12 (3H, t), 3.36 (2H, m), 4.51 (2H, m), 7.07 (2H, m), 7.33 (2H, m) | m/z = 285 (M) |
| 189 | A | 1.16 (3H, t), 3.40 (2H, m), 4.50 (2H, m), 7.43 (1H, d), 7.66 (1H, d) | |
| 190 | A | 1.12 (3H, t), 3.36 (2H, m), 4.56 (2H, m), 7.24 (2H, d), 7.52 (2H, d) | m/z = 345 (M) |
| 191 | A | 1.12 (3H, t), 2.32 (6H, s), 3.36 (2H, m), 4.51 (2H, m), 6.94 (2H, s), 6.97 (1H, s) | m/z = 295 (M) |
| 192 | A | 1.17 (3H, t), 3.42 (2H, m), 4.63 (2H, m), 7.62 (1H, m), 7.75 (1H, dd), 8.20 (1H, s), 8.22 (1H, d) | m/z = 312 (M) |
| 193 | A | 1.17 (3H, t), 3.43 (2H, m), 4.62 (2H, m), 7.37 (1H, d), 7.52 (1H, dd), 7.74 (1H, d) | m/z = 423 (M) |
| 194 | A | 1.92 (3H, t), 3.45 (2H, m), 4.60 (2H, m), 7.87 (1H, s), 8.14 (1H, s), 8.38 (1H, s) | m/z = 390 (M) |
| 195 | A | 1.19 (3H, t), 3.43 (2H, m), 4.68 (2H, m), 7.81 (2H, s), 7.89 (1H, s) | m/z = 403 (M) |
| 196 | E | 3.32 (2H, t), 3.63 (2H, t), 3.76 (3H, s), 4.19 (2H, s), 4.27 (2H, s), 7.39 (1H, d), 7.73 (1H, dd), 8.35 (1H, d) | 1740 (C=O), 2212 (CN) |
| 198 | E | 3.32 (2H, t), 3.40 (3H, s), 3.63 (2H, t), 4.28 (2H, s) 5.46 (2H, s), 7.39 (1H, d), 7.73 (1H, dd), 8.36 (1H, d) | 2212 (CN) |
| 199 | E | 2.22 (3H, s), 3.31 (2H, t), 3.63 (2H, t), 4.27 (2H, s), 4.46 (2H, s), 7.39 (1H, d), 7.73 (1H, dd), 8.36 (1H, d) | 2212 (CN) |
| 200 | E | 2.44 (3H, s), 3.31 (2H, t), 3.62 (2H, t), 4.26 (2H, s), 4.89 (2H, s), 7.30 (2H, d), 7.39 (1H, d), 7.72 (1H, dd), 7.90 (2H, d), 8.34 (1H, d) | 1684 (C=O), 2211 (CN) |
| 201 | A | 1.29 (3H, t), 1.63 (1H, m), 2.13 (1H, m), 2.63 (1H, m), 2.99 (2H, m), 3.08 (2H, m), 3.57 (1H, m), 3.76 (1H, q), 3.87 (2H, m) | 2209 (CN) |
| 202 | A | 1.64 (1H, m), 2.15 (4H, m), 2.75 (2H, t), 3.04 (2H, m), 3.24 (2H, t), 3.69 (1H, dd), 3.76 (1H, q), 3.86 (2H, m) | 2207 (CN) |
| 203 | A | 1.12 (3H, m), 3.25 (2H, m), 4.56 (2H, m), 7.32 (1H, d), 7.75 (1H, m), 8.37 (1H, m) | 1632, 1458, 1388 |
| 204 | A | 1.16, 1.24 (3H, t × 2), 3.31, 3.45 (2H, q × 2), 4.58, 4.66 (2H, s × 2), 6.16 (2H, td), 7.31, 7.36 (1H, d × 2), 7.56, 7.61 (1H, dd × 2), 8.30 (1H, d) | |
| 205 | A | 1.14 (3H, t), 3.23 (2H, q), 4.48 (2H, s), 5.08 (2Hm, brs), 7.29 (1H, d), 7.62 (1H, dd), 8.27 (1H, s) | |
| 206 | A | 1.13 (3H, t), 2.83 (3H, s), 3.20 (2H, q), 4.44 (1H, brs), 4.49 (2H, s), 7.27 (1H, d), 7.64 (1H, dd), 8.27 (1H, s) | |

TABLE 9-continued

| Compound No. | Synthesis Method | $^1$H-NMR (CDCl$_3$, δ, ppm) | IR (KBr, v, cm$^{-1}$) or MS |
|---|---|---|---|
| 207 | A | 1.14 (3H, t), 2.84 (6H, s), 3.14 (2H, m), 4.29 (2H, s), 7.25 (1H, d), 7.63 (1H, d), 8.30 (1H, s) | |
| 208 | A | 1.19 (3H, t), 3.85 (2H, q), 5.06 (2H, s), 7.35 (1H, d), 7.73 (1H, dd), 8.27 (1H, d) | m/z = 216 (M; H) |
| 211 | C | 1.70 (3H, d), 2.81 (3H, s), 5.33 (1H, q), 7.38 (1H, d), 7.71 (1H, dd), 8.41 (1H, d) | 1463, 1380, 1237 |

Synthesis Example 14: N-[1-((6-chloropyridin-3-yl)methyl)pyridin-2(1H)-ylidene]-2,2,2-trifluoroacetamide (Compound 212)

(1) 2-aminopyridine in an amount of 25 g (270 mmol) was dissolved in 200 mL of anhydrous dichloromethane, 41 mL (30 g, 300 mmol) of triethylamine was added, and the mixture was cooled to 0° C. Next, 38 mL (57 g, 270 mmol) of trifluoroacetic anhydride was added dropwise over 15 minutes, and the mixture was stirred at room temperature for 2 hours. Following reaction completion, the reaction mixture was poured into about 100 mL of ice water and stirred for 10 minutes. The mixture was then transferred to a separatory funnel and liquid-liquid extraction was carried out. The organic phase was washed twice with 150 mL of water, washed twice with 150 mL of a 1% aqueous HCl solution, then dried over anhydrous magnesium sulfate and concentrated under reduced pressure, giving 36 g of 2,2,2-trifluoro-N-(pyridin-2(1H)-ylidene)acetamide (yield, 71%).

$^1$H-NMR (CDCl$_3$, δ, ppm): 7.20 (1H, ddd), 7.83 (1H, td), 8.20 (1H, d), 8.35 (1H, d), 10.07 (1H, brs)

$^{13}$C-NMR (CDCl$_3$, δ, ppm): 115.3, 115.5 (q), 121.6, 139.1, 147.9, 149.5, 155.3 (q)

MS: m/z=191 (M+H)

(2) 2-chloro-5-chloromethylpyridine in an amount of 20 g (126 mmol) was dissolved in 200 mL of anhydrous acetonitrile, then 24 g (126 mmol) of 2,2,2-trifluoro-N-(pyridin-2(1H)-ylidene)acetamide obtained by the above method and 21 g (151 mmol) of potassium carbonate were added and refluxing under heating was carried out for 6 hours, followed by 10 hours of stirring at room temperature. Following reaction completion, the reaction mixture was filtered, and the filtrate was concentrated under reduced pressure. Diethyl ether was added to the concentrate to effect crystallization, and the resulting crystals were collected by filtration, then thoroughly washed with diethyl ether and water. The crystals thus obtained were dried at 60° C. and reduced pressure for 1 hour, giving 26 g of the target compound (yield, 66%).

$^1$H-NMR (CDCl$_3$, δ, ppm): 5.57 (2H, s), 6.92 (1H, td), 7.31 (1H, d), 7.80 (1H, td), 7.87 (1H, dd), 7.99 (1H, dd), 8.48 (2H, m)

$^{13}$C-NMR (CDCl$_3$, δ, ppm): 53.8, 115.5, 117.2 (q), 122.1, 124.7, 130.0, 139.2, 140.0, 142.5, 149.7, 151.8, 158.9, 163.5 (q)

MS: m/z=316 (M+H)

(3) Powder X-Ray Diffraction Analysis of Crystals

In powder x-ray diffraction analysis, measurement was carried out under the following conditions.

Apparatus: RINT-2200 (Rigaku Corporation)
X-rays: Cu—Kα (40 kV, 20 mA)
Scanning range: 4 to 40°
Sampling width: 0.02°
Scanning rate: 1°/min The results are given below (FIG. 1).

Diffraction angles (2θ): 8.7°, 14.2°, 17.5°, 18.3°, 19.8°, 22.4°, 30.9°, 35.3°

(4) Differential Scanning Calorimetry (DSC)

In differential scanning calorimetry, measurement was carried out under the following conditions.

Apparatus: DSC-60
Sample cell: aluminum
Temperature range: 50 to 250° C. (temperature rise rate, 10° C./min)

Figure 2:
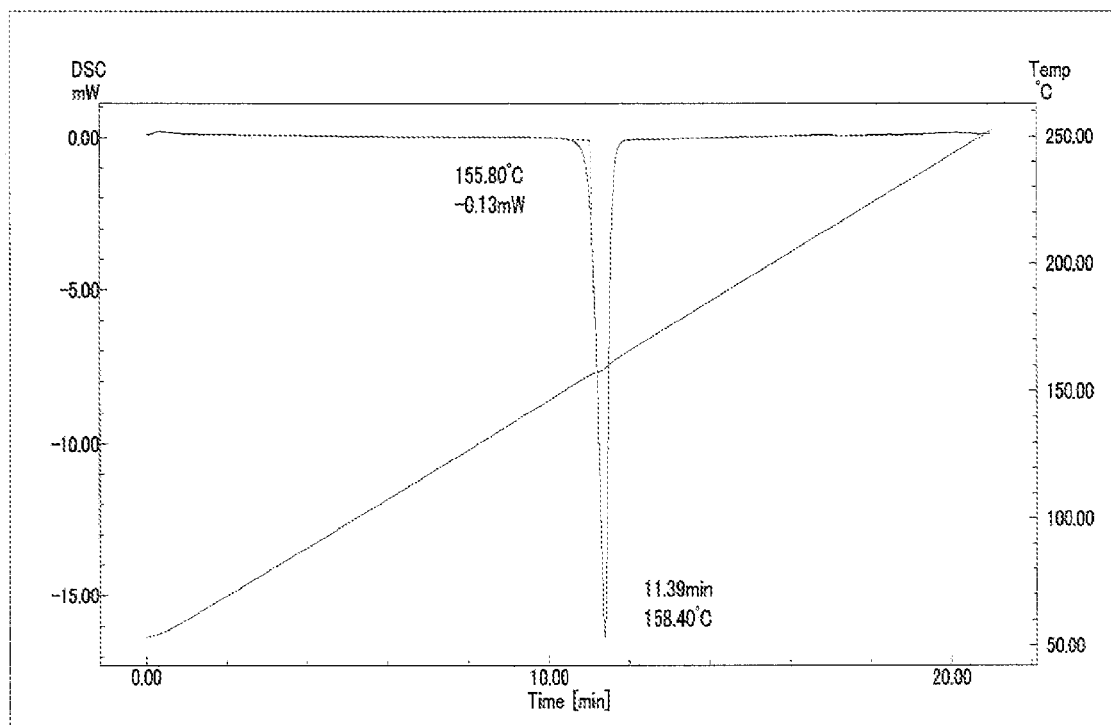
FIG. 2 is a graph showing the results of differential scanning calorimetry on the crystals of N-[1-((6-chloropyridin-3-yl)methyl)pyridin-2(1H)-ylidene]-2,2,2-trifluoroacetamide prepared by the first preparation method.

The results are shown in FIG. 2.

(5) In addition, similar crystals were obtained by using the methods described in (i) to (iv) below (second to fifth preparation methods) to carry out recrystallization. The resulting crystals were subjected to powder x-ray diffraction analysis and differential scanning calorimetry under the same measurement conditions as indicated above.

(i) Second Preparation Method

About 25 mL of hexane and about 25 mL of ethyl acetate were added to Compound 212 (700 mg) and the mixture was heated to 65° C. on a hot water bath, effecting complete dissolution. The solution was slowly returned to room temperature and left to stand overnight. The crystals that precipitated out were collected by filtration and washed with a small amount of a 95:5 solution of hexane and ethyl acetate. The washed crystals were placed in a desiccator and dried for 2 hours under reduced pressure, giving 349 mg of white crystals.

Figure 3:
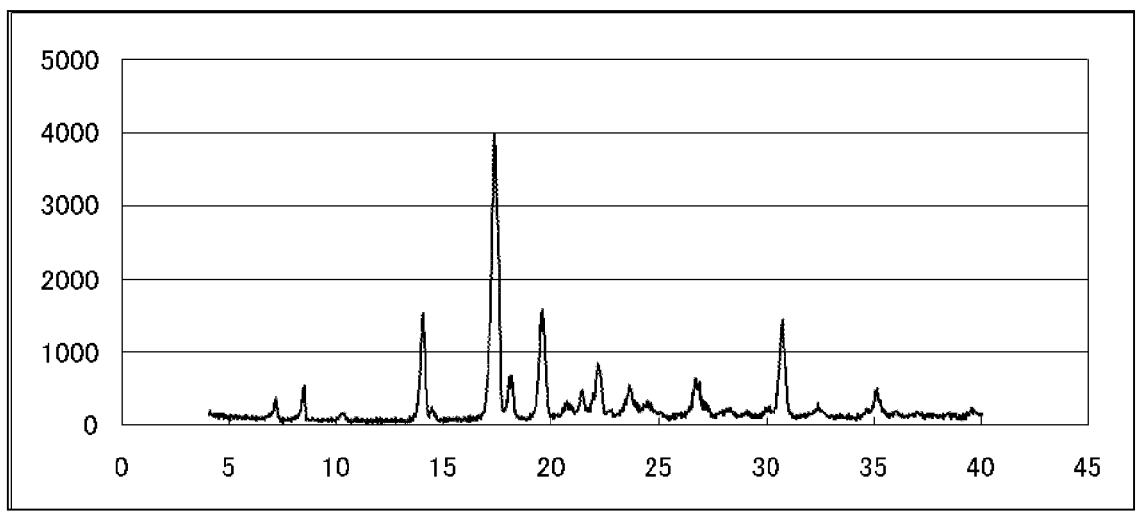
FIG. 3 is a graph showing the results of powder x-ray diffraction analysis on the crystals of N-[1-((6-chloropyridin-3-yl)methyl)pyridin-2(1H)-ylidene]-2,2,2-trifluoroacetamide prepared by a second preparation method.

The results of powder x-ray diffraction analysis were as follows (FIG. 3).

Diffraction angle (2θ): 8.5°, 14.0°, 17.3°, 18.1°, 19.6°, 22.2°, 30.8°, 35.2°

Figure 4:
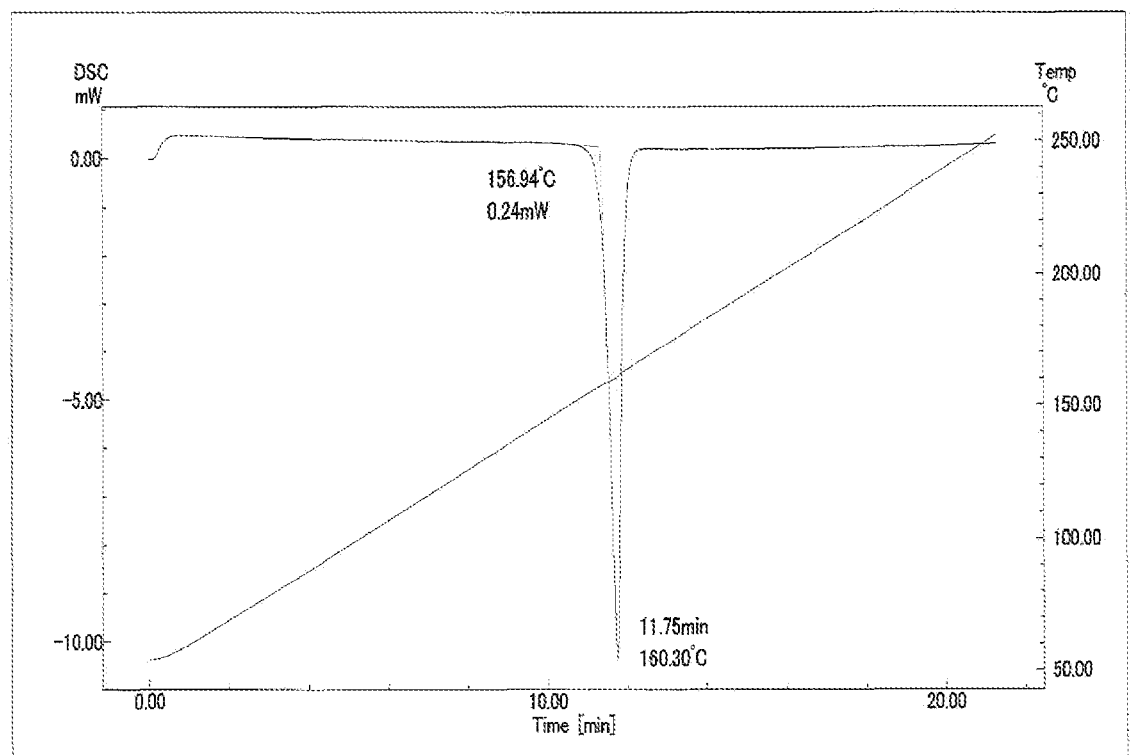
FIG. 4 is a graph showing the results of differential scanning calorimetry on the crystals of N-[1-((6-chloropyridin-3-yl)methyl)pyridin-2(1H)-ylidene]-2,2,2-trifluoroacetamide prepared by the second preparation method.

The results of differential scanning analysis are shown in FIG. 4.

(ii) Third Preparation Method

An amount of 28 mL of 2-propanol was added to Compound 212 (1.0 g) and the mixture was heated to 65° C. on a hot water bath, effecting complete dissolution. The solution was slowly returned to room temperature and left to stand overnight. The crystals that precipitated out were collected by filtration and washed with a small amount of 2-propanol. The washed crystals were then placed in a desiccator and dried for 2 hours under reduced pressure, giving 695 mg of white crystals.

Figure 5:
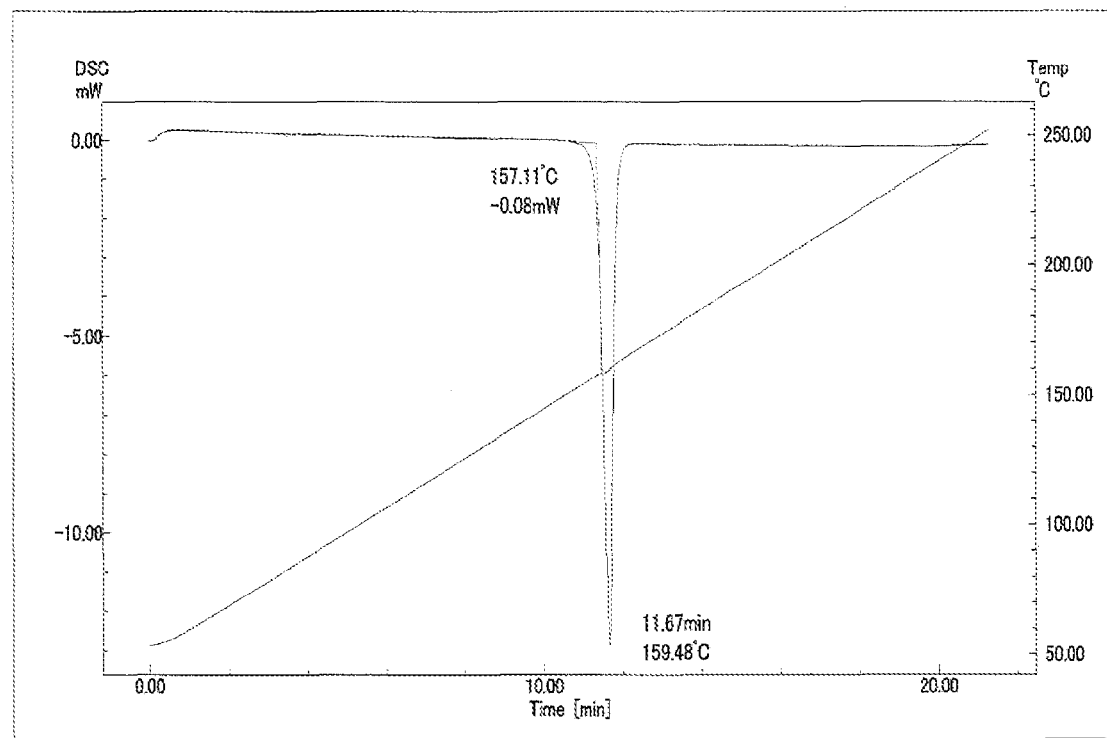
FIG. 5 is a graph showing the results of differential scanning calorimetry on the crystals of N-[1-((6-chloropyridin-3-yl)methyl)pyridin-2(1H)-ylidene]-2,2,2-trifluoroacetamide prepared by a third preparation method.

The results of differential scanning analysis are shown in FIG. 5.

(iii) Fourth Preparation Method

About 30 mL of toluene was added to Compound 212 (700 mg) and the mixture was heated to 65° C. on a hot water bath, effecting complete dissolution. The solution was slowly returned to room temperature and left to stand overnight. The crystals that precipitated out were collected by filtration and washed with a small amount of toluene. The washed crystals were then placed in a desiccator and dried for 2 hours under reduced pressure, giving 440 mg of white crystals.

Figure 6:
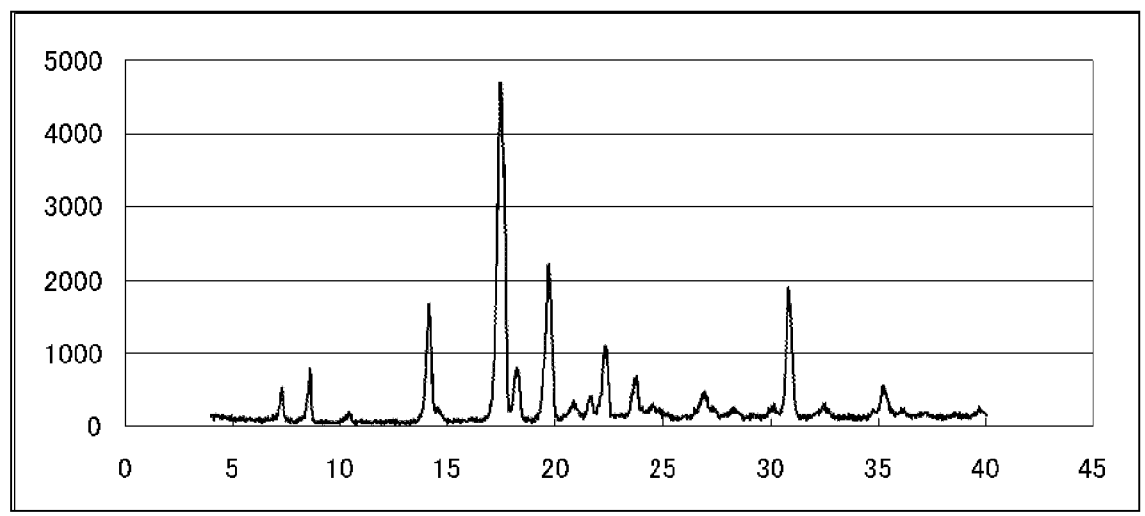
FIG. 6 is a graph showing the results of powder x-ray diffraction analysis on the crystals of N-[1-((6-chloropyridin-3-yl)methyl)pyridin-2(1H)-ylidene]-2,2,2-trifluoroacetamide prepared by a fourth preparation method.

The results of powder x-ray diffraction analysis were as follows (FIG. 6).

Diffraction angle (2θ): 8.6°, 14.2°, 17.5°, 18.3°, 19.7°, 22.3°, 30.9°, 35.3°

Figure 7:
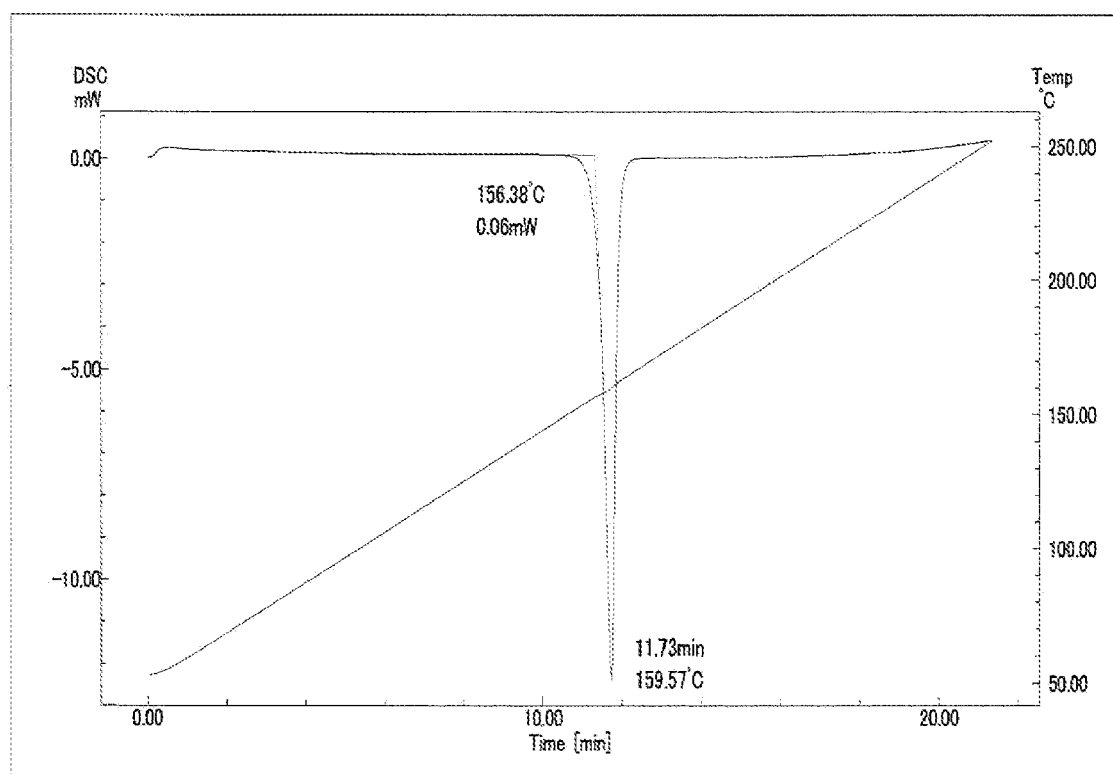
FIG. 7 is a graph showing the results of differential scanning calorimetry on the crystals of N-[1-((6-chloropyridin-3-yl)methyl)pyridin-2(1H)-ylidene]-2,2,2-trifluoroacetamide prepared by the fourth preparation method.

The results of differential scanning analysis are shown in FIG. 7.

(iv) Fifth Preparation Method

About 2 mL of methanol and about 2 mL of water were added to Compound 212 (50 mg) and the mixture was heated to 65° C. on a hot water bath, effecting dissolution. The solution was returned to room temperature and left to stand overnight. The crystals that precipitated out were collected by filtration, giving 16 mg of white crystals.

Figure 8:
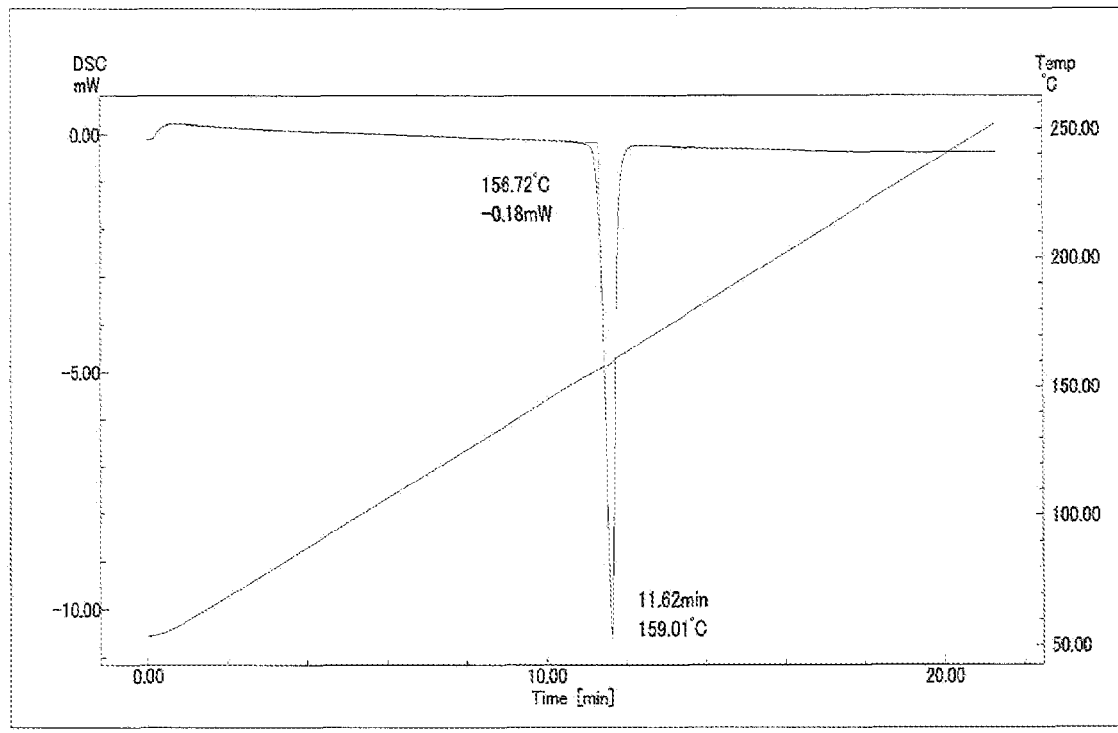
FIG. 8 is a graph showing the results of differential scanning calorimetry on the crystals of N-[1-((6-chloropyridin-3-yl)methyl)pyridin-2(1H)-ylidene]-2,2,2-trifluoroacetamide prepared by a fifth preparation method.

The results of differential scanning analysis are shown in FIG. 8.

Synthesis Example 14: Alternative Method for Step (1)

2-aminopyridine in an amount of 1.0 g (10.6 mmol) was dissolved in 10 mL of ethyl acetate, following which 1.78 mL (1.2 eq) of triethylamine was added, then 1.62 mL (1.1 eq) of trifluoroacetic anhydride was added under ice cooling. Stirring was subsequently carried out for 2 hours at room temperature, then 10 mL of ethyl acetate and 10 mL of water were added, after which the mixture was again stirred and liquid-liquid extraction was carried out. The ethyl acetate phase was washed twice with 10 mL of water, then dried over anhydrous magnesium sulfate and concentrated under reduced pressure, giving 1.56 g of 2,2,2-trifluoro-N-(pyridin-2(1H)-ylidene)acetamide (yield, 77.2%).

Synthesis Example 14: Alternative Method 2 for Step (1)

2-aminopyridine in an amount of 0.94 g (10 mmol) was dissolved in 20 mL of tetrahydrofuran (THF), following which 2.84 g (20 mmol) of ethyl trifluoroacetate and 1.22 g (10 mmol) of dimethylaminopyridine were added, and refluxing was carried out for 22 hours. THF was removed by distillation, following which purification was carried out with a silica gel column (developing solvent: 4:1 solution of hexane and ethyl acetate), giving 0.26 g of 2,2,2-trifluoro-N-(pyridin-2(1H)-ylidene)acetamide (yield, 13.7%).

Synthesis Example 14: Alternative Method 2-chloro-5-chloromethylpyridine in an amount of 3.00 g (18.6 mmol) was dissolved in 20 mL of anhydrous dimethylformamide (DMF), 1.75 g (18.6 mmol) of 2-aminopyridine was added, and the mixture was stirred out at 80° C. for 8 hours and at room temperature for 5 hours. Following reaction completion, DMF was distilled off under reduced pressure and acetonitrile was added, whereupon a solid separated out. The solid was collected by filtration, thoroughly washed with acetonitrile, then dried, giving 2.07 g of 1-[(6-chloropyridin-3-yl)methyl]pyridin-2(1H)-imine hydrochloride (yield, 44%).

$^1$H-NMR (DMSO-d$_6$, δ, ppm): 5.65 (2H, s), 6.96 (1H, t), 7.23 (1H, m), 7.57 (1H, d), 7.80 (1H, m), 7.91 (1H, m), 8.28 (1H, m), 8.49 (1H, d), 9.13 (2H, brs)

An amount of 50 mg (0.20 mmol) of 1-[(6-chloropyridin-3-yl)methyl]pyridin-2(1H)-imine hydrochloride obtained by the above method was dissolved in 5 mL of anhydrous dichloromethane, 122 mg (1.00 mmol) of DMAP and 50 mg (0.24 mmol) of trifluoroacetic anhydride were added in this order under ice cooling, and the mixture was stirred for 1 hour at room temperature. Following reaction completion, the reaction mixture was diluted with dichloromethane, washed with 1% hydrochloric acid, then dried over anhydrous magnesium sulfate. Dichloromethane was removed by distillation under reduced pressure, giving the target compound in an amount of 42 mg (yield, 67%). The NMR spectrum agreed with that of the product obtained by the method described above.

Synthesis Example 15: 2,2-dibromo-N-[1-((6-chloropyridin-3-yl)methyl)pyridin-2(1H)-ylidene]-acetamide (Compound 241)

An amount of 200 mg (0.78 mmol) of 1-[(6-chloropyridin-3-yl)methyl]pyridin-2(1H)-imine hydrochloride obtained in the method described under "Synthesis Example 14, Alternative Method," 238 mg (1.95 mmol) of DMAP and 224 mg (1.17 mmol) of EDC-HCl were dissolved in 10 mL of anhydrous dichloromethane, following which 101 μL (202 mg, 1.17 mmol) of dibromoacetic acid was added and the mixture was stirred overnight at room temperature. Following reaction completion, the reaction mixture was diluted with dichloromethane, washed once with water and twice with 1% aqueous HCl, then dried over anhydrous magnesium sulfate and concentrated under reduced pressure, giving the target compound in an amount of 50 mg (yield, 15%).

$^1$H-NMR (CDCl$_3$, δ, ppm): 5.56 (2H, s), 5.99 (1H, s), 6.78 (1H, td), 7.33 (1H, d), 7.69 (1H, td), 7.76 (1H, dd), 7.93 (1H, dd), 8.39 (1H, d), 8.50 (1H, d)

$^{13}$C-NMR (CDCl$_3$, δ, ppm): 44.6, 53.1, 113.7, 121.9, 124.8, 130.1, 138.2, 139.7, 141.2, 149.5, 152.0, 159.4, 172.2

Synthesis Example 16: N-[1-((6-chloro-5-fluoropyridin-3-yl)methyl)pyridin-2(1H)-ylidene]-2,2,2-trifluoroacetamide (Compound 227)

2-chloro-3-fluoro-5-methylpyridine in an amount of 4.00 g (27.6 mmol) was dissolved in 80 mL of carbon tetrachloride, following which 7.37 g (41.4 mmol) of N-bromosuccinimide and 20 mg of benzoyl peroxide were added and the mixture was refluxed overnight under heating. Following reaction completion, the reaction mixture was returned to room temperature, concentrated under reduced pressure, and purified by silica gel column chromatography (hexane/ethyl acetate=19:1), giving 3.06 g of 5-(bromomethyl)-2-chloro-3-fluoropyridine (yield, 51%).

$^1$H-NMR (CDCl$_3$, δ, ppm): 4.45 (2H, s), 7.54 (1H, dd), 8.23 (1H, s)

An amount of 50 mg (0.22 mmol) of 5-(bromomethyl)-2-chloro-3-fluoropyridine obtained by the above method was dissolved in 5 mL of anhydrous acetonitrile, following which mg (0.22 mmol) of 2,2,2-trifluoro-N-(pyridin-2(1H)-ylidene)acetamide obtained by the method in "Synthesis Example 14, Step (1)" and 36 mg (0.26 mmol) of potassium carbonate were added in this order and refluxing under heating was carried out for 7 hours. Following reaction completion, the reaction mixture was returned to room temperature, the insoluble matter was filtered off, and the filtrate was concentrated under reduced pressure. Diethyl ether was added to the resulting concentrate, whereupon a solid separated out. The solid was collected by filtration and washed with diethyl ether, then dried under reduced pressure in a desiccator, giving the target compound in an amount of 29 mg (yield, 40%).

$^1$H-NMR (CDCl$_3$, δ, ppm): 5.54 (2H, s), 6.89 (1H, td), 7.76 (1H, dd), 7.80 (1H, td), 7.85 (1H, d), 8.29 (1H, d), 8.57 (1H, d)

MS: m/z=334 (M+H)

Synthesis Example 17: N-[1-((6-fluoropyridin-3-yl)methyl)pyridin-2(1H)-ylidene)-2,2,2-trifluoroacetamide (Compound 229)

2-fluoro-5-methylpyridine in an amount of 500 mg (4.50 mmol) was dissolved in 50 mL of carbon tetrachloride, following which 1.20 g (6.76 mmol) of N-bromosuccinimide and 20 mg of benzoyl peroxide were added and refluxing under heating was carried out for 2.5 hours. Following reaction completion, the reaction mixture was returned to room temperature, the solvent was removed by distillation under reduced pressure, and purification was carried out by silica gel column chromatography (hexane/ethyl acetate=19:1), giving 300 mg of 5-bromomethyl-2-fluoropyridine (yield, 35%).

An amount of 57 mg (0.30 mmol) of 5-bromomethyl-2-fluoropyridine obtained from the above method was dissolved in 10 mL of anhydrous acetonitrile, following which 57 mg (0.30 mmol) of 2,2,2-trifluoro-N-(pyridin-2(1H)-ylidene)acetamide synthesized by the method in "Synthesis Example 14, Step (1)" and 69 mg (0.50 mmol) of potassium carbonate were added in this order and the mixture was refluxed under heating for 6 hours. Following reaction completion, the reaction mixture was returned to room temperature, the insoluble matter was filtered off, and the filtrate was concentrated under reduced pressure. Purification was carried out by silica gel column chromatography (hexane/ethyl acetate=1:1→3:1), giving 21 mg of the target compound (yield, 23%).

$^1$H-NMR (CDCl$_3$, δ, ppm): 5.56 (2H, s), 6.89 (1H, td), 6.94 (1H, d), 7.79 (1H, td), 7.87 (1H, d), 8.03 (1H, m), 8.31 (1H, s), 8.54 (1H, d)

MS: m/z=300 (M+H)

Synthesis Example 18: N-[1-((6-bromopyridin-3-yl)methyl)pyridin-2(1H)-ylidene]-2,2,2-trifluoroacetamide (Compound 231)

An amount of 500 mg (2.92 mmol) of 2-bromo-5-methylpyridine was dissolved in 15 mL of carbon tetrachloride, following which 623 mg (3.50 mmol) of N-bromosuccinimide and 10 mg of benzoyl peroxide were added and the mixture was refluxed under heating for 19 hours. Following reaction completion, the reaction mixture was returned to room temperature and concentrated under reduced pressure, then purified by silica gel column chromatography (hexane/ethyl acetate=19:1), giving 143 mg of 2-bromo-5-bromomethylpyridine (yield, 20%).

$^1$H-NMR (CDCl$_3$, δ, ppm): 4.42 (2H, s), 7.47 (1H, d), 7.59 (1H, dd), 8.38 (1H, d)

An amount of 70 mg (0.28 mmol) of 2-bromo-5-bromomethylpyridine obtained by the above method was dissolved in 10 mL of anhydrous acetonitrile, following which 54 mg (0.28 mmol) of 2,2,2-trifluoro-N-(pyridin-2(1H)-ylidene)acetamide synthesized by the method described in "Synthesis Example 14, Step (1)" and 46 mg (0.34 mmol) of potassium carbonate were added in this order and refluxing was carried out under heating for 6 hours. Following completion of the reaction, the reaction mixture was returned to room temperature, the insoluble matter was removed by filtration, and the filtrate was concentrated under reduced pressure. Diethyl ether was then added thereto, whereupon a solid separated out. The solid was collected by filtration, washed with diethyl ether, then dried under reduced pressure in a desiccator, giving the target compound in an amount of 81 mg (yield, 82%).

$^1$H-NMR (CDCl$_3$, δ, ppm): 5.52 (2H, s), 6.88 (1H, t), 7.48 (1H, d), 7.78 (2H, m), 7.84 (1H, d), 8.44 (1H, d), 8.53 (1H, d)

MS: m/z=360 (M+H)

Synthesis Example 19: 2-chloro-N-[1-((6-chloropyridin-3-yl)methyl)pyridin-2(1H)-ylidene]acetamide (Compound 236)

An amount of 70 mg (0.27 mmol) of 1-[(6-chloropyridin-3-yl)methyl]pyridin-2(1H)-imine hydrochloride obtained by the method described in "Synthesis Example 14, Alternative Method" was dissolved in 4 mL of anhydrous dichloromethane, following which 82 mg (0.67 mmol) of DMAP, 25 mg (0.27 mmol) of chloroacetic acid and 62 mg (0.32 mmol) of EDC-HCl were added in this order, and the mixture was stirred overnight at room temperature. Following reaction completion, the reaction mixture was diluted by adding dichloromethane, washed with water and 1% aqueous HCl, and dried over anhydrous magnesium sulfate, then concentrated under reduced pressure, giving the target compound in an amount of 4 mg (yield, 5%).

$^1$H-NMR (CDCl$_3$, δ, ppm): 4.17 (2H, s), 5.46 (2H, s), 6.64 (1H, td), 7.31 (1H, d), 7.60 (1H, td), 7.64 (1H, dd), 7.80 (1H, dd), 8.32 (1H, d), 8.45 (1H, d)

MS: m/z=296 (M+H)

Synthesis Example 20: N-[1-(1-(6-chloropyridin-3-yl)ethyl)pyridin-2(1H)-ylidene]-2,2,2-trifluoroacetamide (Compound 237)

An amount of 44 mg (0.23 mmol) of 2,2,2-trifluoro-N-(pyridin-2(1H)-ylidene)acetamide obtained by the method in "Synthesis Example 14, Step (1)" was dissolved in 8 mL of anhydrous acetonitrile, following which 72 mg (0.23 mmol) of 1-(6-chloropyridin-3-yl)ethyl 4-methylbenzenesulfonate synthesized by the method described in *Biosci. Biotechnol. Biochem.*, 67(5), 980-988 (2003) and 38 mg of potassium carbonate were added, and refluxing under heating was carried out for 100 minutes. Following reaction completion, the reaction mixture was returned to room temperature, the insoluble matter was removed by filtration, and the filtrate was concentrated under reduced pressure. The concentrate was purified by silica gel column chromatography (hexane/ethyl acetate=3:1), giving the target compound in an amount of 24 mg (yield, 32%).

$^1$H-NMR (CDCl$_3$, δ, ppm): 1.89 (3H, d), 6.89 (1H, td), 7.08 (1H, q), 7.32 (1H, d), 7.66 (1H, dd), 7.76 (2H, m), 8.44 (1H, d), 8.50 (1H, d)

$^{13}$C-NMR (CDCl$_3$, δ, ppm): 19.2, 55.1, 115.1, 117.4 (q), 122.0, 124.8, 133.7, 135.2, 138.4, 141.4, 148.6, 151.9, 159.1, 163.9 (q)

MS: m/z=330 (M+H)

Synthesis Example 21: N-[1-((6-chloropyridin-3-yl)methyl)pyridin-2(1H)-ylidene]-2,2-difluoroacetamide (Compound 238)

2-aminopyridine in an amount of 400 mg (4.26 mmol) was dissolved in 10 mL of anhydrous dichloromethane, following which 322 μL (490 mg, 5.11 mmol) of difluoroacetic acid, 982 mg (5.10 mmol) of EDC-HCl and 622 mg (5.11 mmol) of DMAP were added, and the mixture was stirred at room temperature for 61 hours. Following solution completion, the reaction mixture was diluted with dichloromethane, washed once with water and twice with 1% aqueous HCl, then dried over anhydrous magnesium sulfate, and concentrated under reduced pressure, giving 102 mg of 2,2-difluoro-N-(pyridin-2(1H)-ylidene)acetamide (yield, 14%).

$^1$H-NMR (CDCl$_3$, δ, ppm): 6.03 (1H, t), 7.15 (1H, m), 7.78 (1H, td), 8.20 (1H, d), 8.34 (1H, dd), 8.72 (1H, brs)

An amount of 100 mg (0.58 mmol) of 2,2-difluoro-N-(pyridin-2(1H)-ylidene)acetamide obtained by the above method was dissolved in 10 mL of anhydrous acetonitrile, then 94 mg (0.58 mmol) of 2-chloro-5-chloromethylpyridine dissolved in 5 mL of anhydrous acetonitrile was added, following which 84 mg (0.63 mmol) of potassium carbonate was added, and refluxing under heating was carried out for 140 minutes. Following reaction completion, the reaction mixture was returned to room temperature, the insoluble matter was removed by filtration, and the filtrate was concentrated under reduced pressure. Ether was added to the concentrate, whereupon a solid separated out. The solid was collected by filtration and thoroughly dried, giving 63 mg of the target compound (yield, 37%).

$^1$H-NMR (CDCl$_3$, δ, ppm): 5.52 (2H, s), 5.90 (1H, t), 6.79 (1H, td), 7.33 (1H, d), 7.71 (1H, m), 7.77 (1H, dd), 7.85 (1H, dd), 8.45 (1H, d), 8.50 (1H, d)

$^{13}$C-NMR (DMSO-d$_6$, δ, ppm): 53.0, 111.0 (t), 115.2, 120.7, 124.7, 131.7, 140.6, 141.6, 143.2, 150.4, 150.9, 158.3, 169.4 (t)

MS: m/z=298 (M+H)

Synthesis Example 22: 2-chloro-N-[1-((6-chloropyridin-3-yl)methyl)pyridin-2(1H)-ylidene]-2,2-difluoroacetamide (Compound 239)

2-aminopyridine in an amount of 200 mg (2.13 mmol) was dissolved in 5 mL of dichloromethane, following which 491 mg (2.55 mmol) of EDC-HCl, 311 mg (2.55 mmol) of DMAP and 187 μL (2.23 mmol, 290 mg) of chlorodifluoroacetic acid were added in this order and the mixture was stirred overnight. Following reaction completion, the reaction mixture was diluted with dichloromethane, washed with water and 1% hydrochloric acid, then dried over anhydrous magnesium sulfate, giving 105 mg of 2-chloro-2,2-difluoro-N-(pyridin-2(1H)-ylidene)acetamide (yield, 24%).

$^1$H-NMR (CDCl$_3$, δ, ppm): 7.19 (1H, dd), 7.82 (1H, m), 8.18 (1H, d), 8.36 (1H, d), 9.35 (1H, brs)

An amount of 53 mg (0.33 mmol) of 2-chloro-5-chloromethylpyridine dissolved in 6 mL of anhydrous acetonitrile was added to 68 mg (0.33 mmol) of 2-chloro-2,2-difluoro-N-(pyridin-2(1H)-ylidene)acetamide synthesized by the above method, following which 50 mg (0.36 mmol) of potassium carbonate was added and refluxing under heating was carried out for 1 hour. Following reaction completion, the reaction mixture was returned to room temperature then concentrated under reduced pressure. Diethyl ether was added to the concentrate, whereupon a solid separated out. The solid was collected by filtration and dried, affording the target compound in an amount of 49 mg (yield, 45%).

$^1$H-NMR (CDCl$_3$, δ, ppm): 5.56 (2H, s), 6.92 (1H, t), 7.33 (1H, d), 7.82 (1H, m), 7.91 (1H, dd), 8.02 (1H, d), 8.45 (1H, d), 8.48 (1H, d)

$^{13}$C-NMR (CDCl$_3$, δ, ppm): 53.8, 115.2, 120.1 (t), 122.1, 124.8. 139.0. 140.0. 142.3, 150.0, 151.9, 159.1, 159.1, 165.8 (t)

MS: m/z=332 (M+H)

Synthesis Example 23: 2,2,2-trichloro-N-[1-((6-chloropyridin-3-yl)methyl)pyridin-2(1H)-ylidene]acetamide (Compound 235)

An amount of 70 mg (0.27 mmol) of 1-[(6-chloropyridin-3-yl)methyl]pyridin-2(1H)-imine hydrochloride obtained by the method in "Synthesis Example 14, Alternative Method" was dissolved in 4 mL of anhydrous dichloromethane, following which 94 μL (0.68 mmol, 68 mg) of triethylamine and 33 μg (0.27 mmol, 49 mg) of trichloroacetyl chloride were added in this order, and the mixture was stirred at room temperature for 1 hour. Following reaction completion, water was added, stopping the reaction, and liquid-liquid extraction was carried out with dichloromethane and water. The organic phase was washed once with water and twice with 1% hydrochloric acid, then dried over anhydrous magnesium sulfate and concentrated under reduced pressure. Diethyl ether was added to the concentrate, whereupon a solid separated out. The solid was collected by filtration and dried, affording the target compound in an amount of 61 mg (yield, 62%).

$^1$H-NMR (CDCl$_3$, δ, ppm): 5.59 (2H, s), 6.86 (1H, t), 7.32 (1H, d), 7.78 (1H, td), 7.91 (2H, m), 8.43 (1H, d), 8.50 (1H, d)

MS: m/z=364 (M+H)

Synthesis Example 24: N-[1-((6-chloropyridin-3-yl)methyl)pyridin-2(1H)-ylidene]-2,2,3,3,3-pentafluoropropanamide (Compound 242)

2-aminopyridine (300 mg, 3.19 mmol) was dissolved in 15 mL of anhydrous dichloromethane, following which 919 mg (4.78 mmol) of EDC-HCl, 583 mg (4.78 mmol) of DMAP and 397 μL (628 mg, 3.83 mmol) of pentafluoropropionic acid were added in this order and the mixture was stirred overnight at room temperature. Following reaction completion, the reaction mixture was diluted with dichloromethane, washed once with water and twice with 1% hydrochloric acid, then dried over anhydrous magnesium sulfate and concentrated under reduced pressure, affording 85 mg of 2,2,3,3,3-pentafluoro-N-(pyridin-2(1H)-ylidene)propanamide (yield, 11%).

To 77 mg (0.32 mmol) of 2,2,3,3,3-pentafluoro-N-(pyridin-2(1H)-ylidene)propanamide obtained by the above method were added 52 mg (0.32 mmol) of 2-chloro-5-chloromethylpyridine dissolved in 8 mL of anhydrous acetonitrile and 49 mg (0.35 mmol) of potassium carbonate, after which the mixture was refluxed under heating for 11 hours. Following reaction completion, the reaction mixture was returned to room temperature, the insoluble matter was removed by filtration, and the filtrate was concentrated under reduced pressure. The concentrate was purified by silica gel column chromatography (hexane/ethyl acetate=1:3), affording the target compound in an amount of 12 mg (yield, 10%).

$^1$H-NMR (CDCl$_3$, δ, ppm): 5.56 (2H, s), 6.90 (1H, td), 7.32 (1H, d), 7.79 (2H, m), 7.84 (1H, d), 8.43 (1H, d), 8.56 (1H, d)

MS: m/z=366 (M+H)

Synthesis Example 25: N-[1-((2-chloropyrimidin-5-yl)methyl)pyridin-2(1H)-ylidene]-2,2,2-trifluoroacetamide (Compound 243)

2-chloro-5-methylpyrimidine (1.04 g, 8.13 mmol) was dissolved in 30 mL of carbon tetrachloride, 1.73 g (9.75 mmol) of N-bromosuccinimide and 20 mg of benzoyl peroxide were added, and the mixture was refluxed under heating for 6 hours. Following reaction completion, the reaction mixture was returned to room temperature, concentrated under reduced pressure, and purified by silica gel column chromatography (hexane/ethyl acetate=3:1), affording 641 mg of 5-bromomethyl-2-chloropyridine (yield, 38%).

$^1$H-NMR (CDCl$_3$, δ, ppm): 4.42 (2H, s), 8.66 (2H, s)

An amount of 104 mg (0.50 mmol) of 5-bromomethyl-2-chloropyridine obtained by the above method was dissolved in 6 mL of anhydrous acetonitrile, after which 96 mg (0.50 mmol) of 2,2,2-trifluoro-N-(pyridin-2(1H)-ylidene)acetamide obtained by the method in "Synthesis Example 14, Step (1)" and 76 mg (0.55 mmol) of potassium carbonate were added, and the mixture was refluxed under heating for 1 hour. Following reaction completion, the reaction mixture was returned to room temperature, the insoluble matter was removed by filtration, and the filtrate was concentrated under reduced pressure. Diethyl ether was added to the concentrate, whereupon a solid separated out. The solid was collected by filtration, washed with diethyl ether, then placed in a desiccator and dried under reduced pressure, affording the target compound in an amount of 92 mg (yield, 58%).

$^1$H-NMR (CDCl$_3$, δ, ppm): 5.54 (2H, s), 6.98 (1H, m), 7.87 (1H, m), 8.18 (1H, m), 8.48 (1H, m), 8.83 (2H, m)

$^{13}$C-NMR (CDCl$_3$, δ, ppm): 60.0, 115.6, 117.1 (q), 122.1, 127.5, 139.2, 142.9, 158.8, 160.3 (2C), 161.4, 163.8 (q)

MS: m/z=317 (M+H)

Spectral data for compounds obtained by methods similar to those in Synthesis Examples 14 to 25 are shown in Tables 10 and 11.

TABLE 10

| No. | $^1$NMR (CDCl$_3$, δ, ppm) | IR (KBr, v, cm$^{-1}$) or MS |
|---|---|---|
| 212 | 5.57 (2H, s), 6.92 (1H, td), 7.31 (1H, d), 7.80 (1H, td), 7.87 (1H, dd), 7.99 (1H, dd), 8.48 (2H, m) | m/z = 316 (M + H) |
| 213 | 5.61 (2H, s), 6.93 (1H, dd), 7.68 (1H, s), 7.83 (1H, td), 7.97 (1H, d), 8.53 (1H, d) | m/z = 322 (M + H) |
| 214 | 3.74 (3H, s), 5.40 (2H, s), 6.45 (1H, td), 7.29 (1H, d), 7.46 (2H, m), 7.73 (1H, dd), 8.12 (1H, dd), 8.40 (1H, d) | m/z = 278 (M + H) |
| 215 | 5.53 (2H, s), 7.34 (1H, d), 7.71 (1H, dd), 7.87 (1H, dd), 7.94 (1H, s), 8.49 (1H, d), 8.55 (1H, s) | m/z = 350 (M + H) |
| 216 | 5.54 (2H, s), 7.34 (1H, d), 7.70 (1H, m), 7.80 (1H, m), 7.88 (1H, dd), 8.48 (1H, d), 8.64 (1H, m) | m/z = 334 (M + H) |
| 217 | 5.49 (2H, s), 6.85 (1H, dd), 7.35 (1H, d), 7.76 (1H, dd), 7.85 (1H, dd), 8.44 (1H, d), 8.62 (1H, s) | m/z = 350 (M + H) |
| 218 | 5.56 (2H, s), 7.68 (1H, s), 7.74 (1H, dd), 7.84 (1H, d), 8.58 (1H, d) | m/z = 356 (M + H) |
| 219 | 5.60 (2H, s), 7.69 (1H, s), 7.72 (1H, td), 7.86 (1H, m), 8.67 (1H, m) | m/z = 340 (M + H) |
| 220 | 5.58 (2H, s), 6.90 (1H, d), 7.67 (1H, s), 7.90 (1H, d), 8.61 (1H, s) | m/z = 356 (M + H) |
| 221 | 2.31 (3H, s), 5.50 (2H, s), 6.98 (1H, m), 7.34 (1H, d), 7.73 (1H, dd), 7.77 (2H, m), 8.42 (1H, d) | m/z = 330 (M + H) |
| 222 | 2.40 (3H, S), 5.49 (2H, s), 6.70 (1H, dd), 7.32 (1H, d), 7.70 (1H, d), 7.86 (1H, dd), 8.37 (1H, s), 8.43 (1H, d) | m/z = 330 (M + H) |
| 223 | 2.29 (3H, s), 5.52 (2H, s), 7.32 (1H, d), 7.62 (1H, s), 7.65 (1H, dd), 7.88 (1H, dd), 8.46 (1H, d), 8.50 (1H, d) | m/z = 330 (M + H) |
| 224 | 5.58 (2H, s), 6.81 (1H, m), 7.37 (4H, m), 7.77 (2H, m), 8.50 (1H, d) | m/z = 281 (M + H) |
| 225 | 5.52 (2H, s), 6.85 (1H, m), 7.30 (2H, d), 7.36 (2H, d), 7.75 (1H, td), 7.84 (1H, d), 8.47 (1H, d) | m/z = 315 (M + H) |
| 226 | 5.57 (2H, s), 6.86 (1H, m), 7.26-7.35 (2H, m), 7.78 (1H, td), 7.86 (1H, m), 8.63 (2H, m), 8.67 (1H, d) | m/z = 282 (M + H) |
| 227 | 5.54 (2H, s), 6.89 (1H, td), 7.76 (1H, dd), 7.80 (1H, td), 7.85 (1H, d), 8.29 (1H, d), 8.57 (1H, d) | m/z = 334 (M + H) |
| 228 | 5.62 (2H, s), 6.90 (1H, t), 7.69 (1H, d), 7.81 (1H, t), 7.88 (1H, dd), 8.06 (1H, d), 8.56 (1H, d), 8.78 (1H, s) | m/z = 350 (M + H) |
| 229 | 5.56 (2H, s), 6.89 (1H, td), 6.94 (1H, d), 7.79 (1H, td), 7.87 (1H, d), 8.03 (1H, m), 8.31 (1H, s), 8.54 (1H, d) | m/z = 300 (M + H) |
| 230 | 5.49 (2H, s), 6.89 (1H, t), 7.79-7.90 (2H, m), 8.04 (1H, d), 8.37 (1H, d), 8.56 (1H, m) | m/z = 350 (M + H) |
| 231 | 5.52 (2H, s), 6.88 (1H, t), 7.48 (1H, d), 7.78 (2H, m), 7.84 (1H, d), 8.44 (1H, d), 8.53 (1H, d) | m/z = 360 (M + H) |
| 232 | 5.52 (2H, s), 6.71 (1H, m), 7.35 (1H, d), 7.86 (1H, dd), 7.94 (1H, m), 8.33 (1H, dd), 8.44 (1H, d) | m/z = 334 (M + H) |
| 233 | 5.53 (2H, s), 6.74 (1H, m), 7.33 (1H, d), 7.87 (1H, dd), 8.07 (1H, m), 8.29 (1H, dd), 8.45 (1H, d) | m/z = 334 (M + H) |
| 234 | 5.54 (2H, s), 6.02 (1H, s), 6.77 (1H, t), 7.32 (1H, m), 7.69 (1H, m), 7.77 (1H, d), 7.89 (1H, m), 8.42 (1H, m), 8.49 (1H, s) | m/z = 330 (M + H) |

TABLE 11

| No. | $^1$NMR (CDCl$_3$, δ, ppm) | IR(KBr, v, cm$^{-1}$) or MS |
|---|---|---|
| 235 | 5.59 (2H, s), 6.86 (1H, t), 7.32 (1H, d), 7.78 (1H, td), 7.91 (2H, m), 8.43 (1H, d), 8.50 (1H, d) | m/z = 364 (M + H) |
| 236 | 4.17 (2H, s), 5.46 (2H, s), 6.64 (1H, td), 7.31 (1H, d), 7.60 (1H, td), 7.64 (1H, dd), 7.80 (1H, dd), 8.32 (1H, d), 8.45 (1H, d) | m/z = 296 (M + H) |
| 237 | 1.89 (3H, d), 6.89 (1H, td), 7.08 (1H, q), 7.32 (1H, d), 7.66 (1H, dd), 7.76 (2H, m), 8.44 (1H, d), 8.50 (1H, d) | m/z = 330 (M + H) |

TABLE 11-continued

| No. | $^1$NMR (CDCl$_3$, δ, ppm) | IR(KBr, ν, cm$^{-1}$) or MS |
|---|---|---|
| 238 | 5.52 (2H, s), 5.90 (1H, t), 6.79 (1H, td), 7.33 (1H, d), 7.71 (1H, m), 7.77 (1H, dd), 7.85 (1H, dd), 8.45 (1H, d), 8.50 (1H, d) | m/z = 298 (M + H) |
| 239 | 5.56 (2H, s), 6.92 (1H, t), 7.33 (1H, d), 7.82 (1H, m), 7.91 (1H, dd), 8.02 (1H, d), 8.45 (1H, d), 8.48 (1H, d) | m/z = 332 (M + H) |
| 240 | 5.53 (1H, d), 5.58 (1H, d), 6.06 (1H, s), 6.76 (1H, td), 7.32 (1H, d), 7.69 (1H, m), 7.70 (1H, m), 7.90 (1H, dd), 8.40 (1H, d), 8.50 (1H, d) | m/z = 374 (M + H) |
| 241 | 5.56 (2H, s), 5.99 (1H, s), 6.78 (1H, td), 7.33 (1H, d), 7.69 (1H, td), 7.76 (1H, dd), 7.93 (1H, dd), 8.39 (1H, d), 8.50 (1H, d) | m/z = 418 (M + H) |
| 242 | 5.56 (2H, s), 6.90 (1H, td), 7.32 (1H, d), 7.79 (2H, m), 7.84 (1H, d), 8.43 (1H, d), 8.56 (1H, d) | m/z = 366 (M + H) |
| 243 | 5.54 (2H, s), 6.98 (1H, m), 7.87 (1H, m), 8.18 (1H, m), 8.48 (1H, m), 8.83 (2H, m) | m/z = 317 (M + H) |
| 244 | 4.17 (2H, s), 5.46 (2H, s), 6.63 (1H, td), 7.31 (1H, d), 7.60 (1H, td), 7.65 (1H, dd), 7.80 (1H, dd), 8.32 (1H, d), 8.47 (1H, d) | |

Comparative Example 1: N-[(6-chloropyridin-3-yl)methyl]cyanamide (JP 2003-26661 A, Compound 1)

Cyanogen bromide (220 mg, 2.09 mmol) was dissolved in 10 mL of anhydrous chloroform, and the solution was cooled to 0° C. To this was dropwise added a solution of 500 mg (3.49 mmol) of 2-chloro-5-aminomethylpyridine dissolved in 10 mL of anhydrous chloroform, and the resulting mixture was stirred at 0° C. for 1 hour. The reaction mixture was filtered, then water was added and liquid-liquid extraction was carried out, following which the chloroform phase was dried over anhydrous magnesium sulfate and concentrated under reduced pressure. The concentrate was purified by silica gel column chromatography (hexane/ethyl acetate=1:1), giving 122 mg (yield, 35%) of the target compound.

$^1$H-NMR (CDCl$_3$, δ, ppm): 4.21 (2H, s), 5.74 (1H, brs), 7.36 (1H, d), 7.71 (1H, dd), 8.30 (1H, d)
$^{13}$C-NMR (CDCl$_3$, δ, ppm): 46.5, 116.1, 124.8, 131.5, 138.9, 148.9, 151.4
MS: m/z=166 (M–H)

Comparative Example 2: N-[1-((6-chloropyridin-3-yl)methyl)pyridin-2(1H)-ylidene]cyanamide (Patent Document 6, Compound 20)

[Chem. 26]

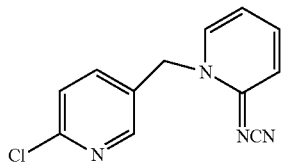

An amount of 128 mg (0.58 mmol) of 1-[(6-chloropyridin-3-yl)methyl]pyridine-2(1H)-imine obtained by the alternative method described in Synthesis Example 14 was dissolved in 5 mL of anhydrous dimethylformamide, NaH (as a 60% dispersion in oil) was added in an amount of 40 mg (net weight, 24 mg; 1.04 mmol), and the mixture was stirred at room temperature for 30 minutes. Next, 60 mg (0.57 mmol) of cyanogen bromide was added, and the resulting mixture was stirred overnight. Following reaction completion, water and ethyl acetate were added to the reaction mixture and liquid-liquid extraction was carried out. The organic phase was dried over anhydrous magnesium sulfate, then concentrated under reduced pressure. The concentrate was purified on a TLC plate (one 0.5 mm plate, developed with 100% ethyl acetate), giving 14 mg of the target compound (yield, 10%).

$^1$H-NMR (CDCl$_3$, δ, ppm): 5.28 (2H, s), 6.55 (1H, m), 7.33 (2H, m), 7.56 (2H, m), 7.75 (1H, dd), 8.40 (1H, d)

Comparative Example 3: N-[1-((6-chloropyridin-3-yl)methyl)pyridin-2(2H)-ylidene]acetamide (Patent Document 4, Compound 2)

[Chem. 27]

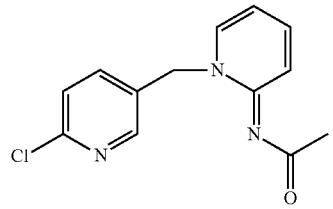

Anhydrous dichloromethane (20 mL) was added to 118 mg (0.46 mmol) of 1-[(6-chloropyridin-3-yl)methyl]pyridine-2(1H)-imine hydrochloride obtained by the alternative method described in Synthesis Example 14, following which 159 μL (1.16 mmol, 116 mg) of triethylamine and 33 μL of acetyl chloride were added and the mixture was stirred at room temperature for 15 minutes. The reaction was stopped by adding water to the reaction mixture, and liquid-liquid extraction was carried out with chloroform and water. The organic phase was washed with a saturated aqueous solution of ammonium chloride, then concentrated. With the addition of hexane thereto, a solid settled out. The solid was collected by filtration and washed, then thoroughly dried, giving 21 mg of the target compound (yield, 17%).

$^1$H-NMR (CDCl$_3$, δ, ppm): 2.21 (3H, s), 5.35 (2H, s), 6.46 (1H, m), 7.32 (1H, d), 7.48 (2H, m), 7.75 (1H, d), 8.10 (1H, dd), 8.45 (1H, dd)
MS: m/z=262 (M+H)

Comparative Example 4: 3-[1-((6-chloropyridin-3-yl)methyl)imidazolidin-2-ylidene]-1,1,1-trifluoropropan-2-one (Patent Document 5, Example 4)

[Chem. 28]

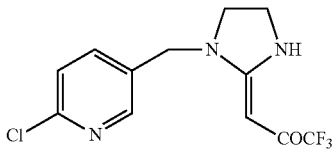

Anhydrous dimethylformamide (15 mL) was added to 1.30 g (33.9 mmol, 780 mg) of NaH (as a 60% dispersion in oil), and the mixture was cooled to 0° C. To this was dropwise added 1.52 mL (1.90 g, 17.0 mmol) of 1,1,1-trifluoroacetone, and stirring was carried out at 0° C. for 10 minutes. To this was added 7.0 mL (110 mmol, 8.35 g) of carbon disulfide, and stirring was carried out at 50° C. for 1 hour. Next, the reaction mixture was cooled to 0° C., 2.1 mL (34.0 mmol, 4.81 g) of methyl iodide was added, and the mixture was stirred overnight at room temperature. Following reaction completion, the reaction mixture was poured into ice water and stirring was carried out until the ice completely melted. The reaction mixture was transferred to a separatory funnel and extracted with ethyl acetate. The organic phase was washed with saturated saline, then dried over anhydrous magnesium sulfate and concentrated under reduced pressure. The concentrate was purified by silica gel chromatography (hexane/ethyl acetate=95:5), and the fractions containing the target compound were collected and concentrated under reduced pressure. Hexane was added thereto, whereupon a solid settled out. The solid was collected by filtration and washed with hexane, then thoroughly dried, giving 460 mg (yield, 13%) of 1,1,1-trifluoro-4,4-bis(methylthio)-3-buten-2-one.

$^1$H-NMR (CDCl$_3$, δ, ppm): 2.56 (3H, s), 2.58 (2H, s), 6.25 (1H, s)

Next, 20 mL of ethylenediamine was added to 2.0 g (12.4 mmol) of 2-chloro-5-chloromethylpyridine, and the mixture was stirred overnight. Following reaction completion, the reaction mixture was concentrated under reduced pressure, after which acetonitrile was added and insoluble matter were removed by filtration. The filtrate was concentrated under reduced pressure, giving 2.45 g (yield, 100%) of N-((6-chloropyridin-3-yl)methyl)ethane-1,2-diamine.

A solution of 77 mg (0.42 mmol) of the N-((6-chloropyridin-3-yl)methyl)ethane-1,2-diamine obtained by the foregoing method in 8 mL of anhydrous acetonitrile was added to 60 mg (0.28 mmol) of 1,1,1-trifluoro-4,4-bis(methylthio)-3-buten-2-one obtained by the foregoing method, and the mixture was refluxed under heating for 40 minutes. Following reaction completion, the reaction mixture was returned to room temperature and concentrated under reduced pressure, after which ethyl acetate and water were added, and liquid-liquid extraction was carried out. The organic phase was washed with anhydrous magnesium sulfate, then concentrated under reduced pressure, and the concentrate was purified by silica gel column chromatography (hexane/ethyl acetate=3:1), giving 59 mg of the target compound (yield, 69%).

$^1$H-NMR (CDCl$_3$, δ, ppm): 3.49 (2H, t), 3.78 (2H, t), 4.40 (2H, s), 5.13 (1H, s), 7.37 (1H, d), 7.56 (1H, dd), 8.31 (1H, d), 9.34 (1H, brs)
m/z=306 (M+H)

Comparative Example 5: 3-[3-((6-chloropyridin-3-yl)methyl)thiazolidin-2-ylidene]-1,1,1-trifluoropropan-2-one (Patent Document 5, Example 3)

[Chem. 29]

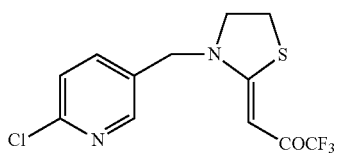

A solution of 36 mg (0.46 mmol) of 2-aminoethanethiol dissolved in 10 mL of ethanol was added to 100 mg (0.46 mmol) of 1,1,1-trifluoro-4,4-bis(methylthio)-3-buten-2-one obtained by the method described in Comparative Example 4, and the mixture was refluxed under heating for 6 hours, then stirred at room temperature for 13 hours. Following reaction completion, the ethanol was distilled off under reduced pressure, after which the condensate was dissolved in ethyl acetate and washed once with water. The washed product was dried over anhydrous magnesium sulfate, then concentrated under reduced pressure, giving 73 mg (yield, 81%) of 1,1,1-trifluoro-3-(thiazolidin-2-ylidene)propan-2-one.

$^1$N-NMR (CDCl$_3$, δ, ppm): 3.35 (2H, m), 4.02 (2H, m), 5.61 (1H, s), 10.40 (1H, brs), 2-chloro-5-chloromethylpyridine (80 mg, 0.50 mmol) dissolved in 8 mL of anhydrous acetonitrile, and potassium carbonate (69 mg, 0.50 mmol) were added to 65 mg (0.33 mmol) of 1,1,1-trifluoro-3-(thiaolidin-2-ylidene)propane-2-one obtained by the foregoing method, and the mixture was refluxed under heating for 2 hours. After reaction completion, the reaction mixture was returned to room temperature, insoluble matter was removed by filtration, and the filtrate was concentrated under reduced pressure. The concentrate was purified by silica gel column chromatography (hexane/ethyl acetate=1:1→4 1:3), giving 53 mg of the target compound (yield, 50%).

$^1$H-NMR (CDCl$_3$, δ, ppm): 3.20 (2H, t), 3.73 (2H, t), 4.61 (2H, s), 5.80 (1H, s), 7.36 (1H, d), 7.53 (1H, dd), 8.31 (1H, d)
MS: m/z=323 (M+H)

Comparative Example 6: 3-[1-((6-chloropyridin-3-yl)methyl)imidazolidin-2-ylidene]-1,1,1,5,5,5-hexafluoropentan-2,4-dione (Patent Document 5, Example 5)

[Chem. 30]

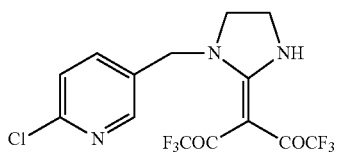

An amount of 31 mg (0.10 mmol) of the 3-[1-((6-chloropyridin-3-yl)methyl)imidazolidin-2-ylidene]-1,1,1-trifluoropropan-2-one obtained by the method described in Comparative Example 4 was dissolved in 2 mL of anhydrous dichloromethane, then 20 μL (0.25 mmol, 20 mg) of pyridine and 28 μL (0.20 mmol, 42 mg) of trifluoroacetic anhydride were added in this order, and the mixture was stirred at room temperature for 30 minutes. The progress of the reaction was checked by thin layer chromatography, whereupon there was found to be some starting material remaining in the system. As a result, another 84 μL (0.60 mmol, 62 mg) of trifluoroacetic anhydride was added, and stirring was carried out for 1 hour at room temperature. Following reaction completion, the reaction mixture was concentrated under reduced pressure, then purified on a TLC plate (one 0.5 mm plate, developed with hexane/ethyl=2:8), giving 30 mg of the target compound (yield, 75%).

$^1$H-NMR (CD$_3$OD, δ, ppm): 3.87 (4H, m), 4.51 (2H, s), 7.50 (1H, d), 7.82 (1H, dd), 8.35 (1H, d)

MS: m/z=402 (M+H)

Comparative Example 7: N-[1-((6-chloropyridin-3-yl)methyl)imidazolidin-2-ylidene]-2,2,2-trifluoroacetamide (Patent Document 5, Example 7)

[Chem. 31]

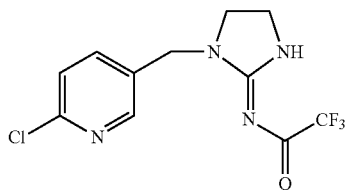

Dimethylcarbonimidodithioate methanesulfonic acid chloride (4.25 g, 18.2 mmol) was dissolved in 30 mL of pyridine, 3.80 mL (5.73 g, 27.3 mmol) of trifluoroacetic anhydride was added dropwise, and the mixture was stirred overnight at room temperature. The reaction mixture was concentrated under reduced pressure, and subjected to liquid-liquid extraction using dichloromethane and water. The resulting organic phase was dried over anhydrous magnesium sulfate, then concentrated, giving 5.36 g of dimethyl (2,2,2-trifluoroacetyl)carbonimidodithioate (yield, 100%).

N-((6-chloropyridin-3-yl)methyl)ethane-1,2-diamine (4.61 g, 24.9 mmol) was synthesized by the method described in Comparative Example 4. This was dissolved in 40 mL of anhydrous acetonitrile, 4.60 g (21.3 mmol) of the dimethyl(2,2,2-trichloroacetyl)carbonimidodithioate obtained by the above method was added, and the resulting mixture was refluxed under heating for 90 minutes. Following reaction completion, the reaction mixture was returned to room temperature, after which the solvent was distilled off under reduced pressure. The solid that settled out was collected by filtration and washed with a small amount of acetonitrile, giving 2.17 g of the target compound (yield, 33%).

$^1$H-NMR (CDCl$_3$, δ, ppm): 3.50 (2H, m), 3.76 (2H, m), 4.60 (2H, s), 7.34 (1H, d), 7.70 (1H, dd), 8.33 (1H, d)

Melting point: 168 to 170° C.

Comparative Example 8: N-[3-((6-chloropyridin-3-yl)methyl)thiazolidin-2-ylidene]-2,2,2-trifluoroacetamide (Patent Document 5, Example 6)

[Chem. 32]

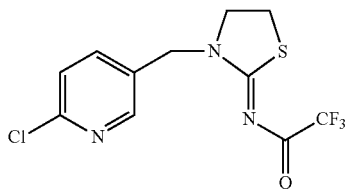

Ethanol (20 mL) was added to 77 mg (1.0 mmol) of 2-aminoethanethiol, 216 mmol (1.0 mmol) of the dimethyl (2,2,2-trifluoroacetyl)carbonimidodithioate synthesized by the method described in Comparative Example 7 was added, and the mixture was stirred overnight at room temperature. Following reaction completion, the solvent was distilled off under reduced pressure, and purification was carried out by silica gel column chromatography (hexane/ethyl acetate=1:1), giving 100 mg of 2,2,2-trifluoro-N-(thiazolidin-2-ylidene)acetamide (yield, 51%). This reaction was carried out once more by the same synthesis method, giving a combined amount of 350 mg of 2,2,2-trifluoro-N-(thiazolidin-2-ylidene)acetamide.

Dimethylformamide (2 mL) and tetrahydrofuran (18 mL) were added to 162 mg (0.82 mmol) of 2,2,2-trifluoro-N-(thiazolidin-2-ylidene)acetamide obtained by the above-described method, following which 198 mg of 2-chloro-5-chloromethylpyridine and 150 mg (1.09 mmol) of potassium carbonate were added, and the mixture was refluxed under heating for 20 hours. Following reaction completion, the reaction mixture was returned to room temperature, insoluble matter was filtered off, and the filtrate was concentrated under reduced pressure. The concentrate was purified on a TLC plate (two 0.5 mm plates, developed with 100% ethyl acetate), giving 230 mg of the target compound (yield, 87%).

$^1$H-NMR (CDCl$_3$, δ, ppm): 3.27 (2H, m), 3.73 (2H, m), 4.86 (2H, s), 7.36 (1H, d), 7.72 (1H, dd), 8.36 (1H, d)

Melting point: 96° C.

Example Formulations

Formulation Example 1: Granules

| | |
|---|---|
| Compound 1 | 5 wt % |
| Bentonite | 40 wt % |
| Talc | 10 wt % |
| Clay | 43 wt % |
| Calcium ligninsulfonate | 2 wt % |

The above ingredients were uniformly ground and mixed, following which water was added and the mixture was thoroughly kneaded. The kneaded material was granulated and dried, giving granules.

Formulation Example 2: Granules

| | |
|---|---|
| Compound 212 | 2 wt % |
| Sanx P-252 | 5 wt % |
| Binder | 1.5 wt % |
| Granulation enhancer | 0.5 wt % |
| Clay | 91 wt % |

The above ingredients were uniformly ground and mixed, following which water was added and the mixture was thoroughly kneaded. The kneaded material was granulated and dried, giving granules.

Formulation Example 3: Wettable Powder

| | |
|---|---|
| Compound 3 | 30 wt % |
| Clay | 50 wt % |
| White carbon | 2 wt % |
| Diatomaceous earth | 13 wt % |
| Calcium ligninsulfonate | 4 wt % |
| Sodium lauryl sulfate | 1 wt % |

The above ingredients were uniformly mixed and ground, giving a wettable powder.

Formulation Example 4: Water Dispersible Granules

| | |
|---|---|
| Compound 212 | 30 wt % |
| Clay | 60 wt % |
| Dextrin | 5 wt % |
| Alkyl-maleic acid copolymer | 4 wt % |
| Sodium lauryl sulfate | 1 wt % |

The above ingredients were uniformly ground and mixed, following which water was added and the mixture was thoroughly kneaded. The kneaded material was granulated and dried, giving water dispersible granules.

Formulation Example 5: Flowable Concentrate

| | |
|---|---|
| Compound 8 | 25 wt % |
| POE polystyryl phenyl ether sulfate | 5 wt % |
| Propylene glycol | 6 wt % |
| Bentonite | 1 wt % |
| Xanthan gum, 1% aqueous solution | 3 wt % |
| PRONAL EX-300 (Toho Chemical Industry Co., Ltd.) | 0.05 wt % |
| ADDAC 827 (KI Chemical Industry Co., Ltd.) | 0.02 wt % |
| Water | added to 100 wt % |

The entire amounts of the above ingredients, excluding the 1% aqueous solution of xanthan gum and a suitable amount of water, were premixed, then ground in a wet grinding mill. The 1% aqueous solution of xanthan gum and the remaining water were then added to the total amount of 100 wt %, giving a flowable concentration.

Formulation Example 6: Emulsifiable Concentrate

| | |
|---|---|
| Compound 1 | 15 wt % |
| N,N-dimethylformamide | 20 wt % |
| Solvesso 150 (Exxon Mobil Yugen Kaisha) | 55 wt % |
| Polyoxyethylene alkyl aryl ether | 10 wt % |

The above ingredients were uniformly mixed and dissolved, giving an emulsifiable concentrate.

Formulation Example 7: Dust Formulation

| | |
|---|---|
| Compound 14 | 2 wt % |
| Clay | 60 wt % |
| Talc | 37 wt % |
| Calcium stearate | 1 wt % |

The above ingredients were uniformly mixed, giving a dust formulation.

Formulation Example 8: Low-Drift Dust Formulation

| | |
|---|---|
| Compound 1 | 2 wt % |
| Low-drift clay | 94.5 wt % |
| White carbon | 2 wt % |
| Calcium stearate | 1 wt % |
| Light liquid paraffin | 0.5 wt % |

The above ingredients were uniformly mixed, giving a dust formulation.

Formulation Example 9: Fine Granules F

| | |
|---|---|
| Compound 3 | 2 wt % |
| Carrier | 94 wt % |
| White carbon | 2 wt % |
| Hisol SAS-296 | 2 wt % |

The above ingredients were uniformly mixed, giving a dust formulation.

Formulation Example 10: Liquid Formulation for Drop

| | |
|---|---|
| Compound 1 | 10 wt % |
| Benzyl alcohol | 74.9 wt % |
| Propylene carbonate | 15 wt % |
| BHT | 0.1 wt % |

The above ingredients were uniformly mixed, giving a liquefied drop formulation.

Formulation Example 11: Liquid Formulation for Drop

| | |
|---|---|
| Compound 212 | 48 wt % |
| Ethanol | 52 wt % |

The above ingredients were uniformly mixed, giving a liquefied drop formulation.

In addition, an example of a mixed formulation containing both a compound of the present invention and another pest control agent is provided below.

Formulation Example 12: Granules

| | |
|---|---|
| Compound 212 | 2 wt % |
| Propenazole | 24 wt % |
| Binder | 3.0 wt % |
| Granulation enhancer | 0.5 wt % |
| Clay | 70.5 wt % |

The above ingredients were uniformly ground and mixed, following which water was added and the mixture was thoroughly kneaded. The kneaded material was granulated and dried, giving granules.

Test Examples

Foliar Application Tests

Test Example 1-1: Diamondback Moth Control Test

Leaf discs 5.0 cm in diameter were cut from cabbage plants grown in pots, and these were sprayed with solutions of the inventive compounds at a predetermined concentration prepared to 50% acetone/water (containing 0.05% Tween 20). The treated leaf discs were air dried, following which second-instar larvae were released onto the discs. The leaf discs and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 500 ppm foliar application, Compounds 9, 10, 49, 196, 211, 81, 82, 89, 92, 104, 107, 108, 109, 110, 111, 112, 114, 128, 131, 140, 141, 144, 145, 146, 152, 165, 167, 170, 171, 172, 176, 179, 180, 181, 183, 184, 186, 188, 189, 190, 193, 194, 212, 219, 226, 227, 229, 230, 234, 235, 237, 239, 240, 241, 242 and 243 exhibited insecticidal activities having at least 80% mortality.

Test Example 1-2: Diamondback Moth Control Test

Leaf discs 5.0 cm in diameter were cut from cabbage plants grown in pots, and these were sprayed with solutions of the inventive compounds at a predetermined concentration prepared to 50% acetone/water (containing 0.05% Tween 20). The treated leaf discs were air dried, following which second-instar larvae were released onto the discs. The leaf discs and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 100 ppm foliar application, Compounds 81, 89, 92, 107, 111, 112, 114, 128, 152, 171, 183, 184, 186, 189, 190, 193, 194, 211, 212, 213, 215, 216, 218, 219, 227, 229, 230, 231, 234, 235, 237, 238, 239, 242 and 243 exhibited insecticidal activities having at least 80% mortality.

Test Example 2: Common Cutworm Control Test

Leaf discs 5.0 cm in diameter were cut from cabbage plants grown in pots, and these were sprayed with solutions of the inventive compounds at a predetermined concentration prepared to 50% acetone/water (containing 0.05% Tween 20). The treated leaf discs were air dried, following which third-instar larvae were released onto the discs. The leaf discs and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 500 ppm foliar application, Compounds 46, 202, 68, 82, 89, 92, 96, 104, 108, 128, 140, 176, 184, 189, 190, 193, 212, 219, 227, 229, 230 and 239 exhibited insecticidal activities having at least 80% mortality.

Test Example 3-1: Cotton Aphid Control Test

Leaf discs 2.0 cm in diameter were cut from cucumber plants grown in pots, and these were sprayed with solutions of the inventive compounds at a predetermined concentration prepared to 50% acetone/water (containing 0.05% Tween 20). The treated leaf discs were air dried, following which first-instar larvae were released onto the discs. The leaf discs and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 500 ppm foliar application, Compounds 1, 2, 3, 6, 7, 8, 9, 10, 12, 14, 15, 18, 20, 21, 22, 25, 27, 29, 30, 31, 32, 33, 34, 36, 37, 41, 42, 43, 44, 45, 46, 49, 50, 52, 58, 61, 68, 69, 71, 72, 73, 76, 77, 79, 81, 82, 83, 85, 88, 89, 92, 96, 100, 101, 102, 103, 104, 119, 122, 131, 132, 135, 139, 165, 167, 170, 179, 182, 183, 184, 186, 189, 192, 193, 194, 196, 199, 200, 202, 208, 210, 211, 212, 219, 221, 222, 223, 225, 226, 227, 228, 229, 230, 233, 234, 235, 237, 239 and 243 exhibited insecticidal activities having at least 80% mortality.

By contrast, when Compound 1 (N-[(6-chloropyridin-3-yl)methyl]cyanamide) in Patent Document 1 (Japanese Patent Application Publication No. 2003-26661) was tested by the same method, the cotton aphid mortality from foliar application at 500 ppm was 65%.

Test Example 3-2: Cotton Aphid Control Test

Leaf discs 2.0 cm in diameter were cut from cucumber plants grown in pots, and these were sprayed with solutions of the inventive compounds at a predetermined concentration prepared to 50% acetone/water (containing 0.05% Tween 20). The treated leaf discs were air dried, following which first-instar larvae were released onto the discs. The leaf discs and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 100 ppm foliar application, Compounds 1, 2, 3, 6, 7, 8, 9, 10, 14, 245, 18, 21, 34, 43, 49, 50, 71, 76, 83, 85, 86, 88, 89, 90, 91, 92, 93, 94, 96, 97, 102, 105, 113, 128, 131, 137, 138, 139, 140, 141, 145, 149, 152, 157, 163, 183, 186, 196, 199, 200, 204, 208, 212, 213, 214, 215, 216, 219, 222, 223, 225, 226, 227, 228, 229, 230, 232, 233, 234, 235, 236, 237, 238, 239, 240, 241, 242, 243 and 244 exhibited insecticidal activities having at least 80% mortality.

Test Example 3-3: Cotton Aphid Control Test

Leaf discs 2.0 cm in diameter were cut from cucumber plants grown in pots, and these were sprayed with solutions of the inventive compounds at a predetermined concentration prepared to 50% acetone/water (containing 0.05% Tween 20). The treated leaf discs were air dried, following which first-instar larvae were released onto the discs. The leaf discs and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 20 ppm foliar application, Compounds 1, 2, 3, 6, 7, 8, 14, 18, 21, 82, 86, 88, 89, 90, 91, 94, 95, 128, 137, 138, 157, 199, 200, 212, 213, 214, 219, 226, 227, 229, 230, 231, 233, 234, 235, 236, 237, 238, 239, 240, 241, 242, 243 and 244 exhibited insecticidal activities having at least 80% mortality.

Test Example 4: Green Peach Aphid Control Test

Leaf discs 2.8 cm in diameter were cut from cabbage plants grown in pots, and four adult aphids were released onto each disc. One day later, the adults were removed, and the number of first-instar larvae that had been deposited on each leaf disc was adjusted to 10. Next, the leaf discs parasitized by these first instar larvae were sprayed with solutions of the inventive compounds at a predetermined concentration prepared to 50% acetone/water (containing 0.05% Tween 20). The treated leaf discs were air dried, following which covers were placed over the Petri dishes and the leaf discs and larvae were held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 100 ppm foliar application, Compounds 1, 2, 3, 6, 7, 8, 9, 10, 11 and 212 exhibited insecticidal activities having at least 80% mortality.

Test Example 5: Small Brown Planthopper Control Test

Rice seedlings grown in pots were subjected to the foliar application of solutions of the inventive compounds at a predetermined concentration prepared to 50% acetone/water (containing 0.05% Tween 20). The treated seedlings were air dried, following which second-instar larvae were released onto the seedlings. The seedlings and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 100 ppm foliar application, Compounds 212, 213, 215, 216, 227, 229 and 230 exhibited insecticidal activities having at least 80% mortality.

Test Example 6: Brown Rice Planthopper Control Test

Rice seedlings grown in pots were subjected to the foliar application of solutions of the inventive compounds at a predetermined concentration prepared to 50% acetone/water (containing 0.05% Tween 20). The treated seedlings were air dried, following which second-instar larvae were released onto the seedlings. The seedlings and larvae were then held in an incubation chamber at 25° C. (16-hour period of light, 8-hour dark period). Six days after released, the numbers of live and dead insects were counted, and the mortality was calculated from the following formula. This was a two-replication test.

Mortality (%)=[number of dead insects/(number of live insects+number of dead insects)]×100

From these results, with 100 ppm foliar application, Compounds 1, 2, 3, 6, 7 and 8 exhibited insecticidal activities having at least 80% mortality.

Test Example 7: White-Backed Rice Planthopper Control Test

Rice seedlings grown in pots were subjected to the foliar application of solutions of the inventive compounds at a predetermined concentration prepared to 50% acetone/water (containing 0.05% Tween 20). The treated seedlings were air dried, following which second-instar larvae were released onto the seedlings. The seedlings and larvae were then held in an incubation chamber at 25° C. (16-hour period of light, 8-hour dark period). Four days after released, the numbers of live and dead insects were counted, and the mortality was calculated from the following formula. This was a two-replication test.

Mortality (%)=[number of dead insects/(number of live insects+number of dead insects)]×100

From these results, with 100 ppm foliar application, Compound 1 exhibited an insecticidal activity having at least 80% mortality.

Test Example 8: Green Rice Leafhopper Control Test

Rice seedlings grown in pots were subjected to the foliar application of solutions of the inventive compounds at a predetermined concentration prepared to 50% acetone/water (containing 0.05% Tween 20). The treated seedlings were air dried, following which second-instar were larvae released onto the seedlings. The seedlings and larvae were then held in an incubation chamber at 25° C. (16-hour period of light, 8-hour dark period). Four days after released, the numbers of live and dead insects were counted, and the mortality was calculated from the following formula. This was a two-replication test.

Mortality (%)=[number of dead insects/(number of live insects+number of dead insects)]×100

From these results, with 100 ppm foliar application, Compounds 1 and 212 exhibited insecticidal activities having at least 80% mortality.

Test Example 9: Greenhouse Whitefly Control Test

Adult greenhouse whiteflies were released onto cucumber plants grown in pots, and allowed to laid eggs overnight. One day after the start of oviposition, the adults were removed, and the plants and eggs were held in an incubation chamber at 25° C. (16-hour period of light, 8-hour dark period). Three days after the end of oviposition, leaf discs 2.0 cm in diameter were cut from the cucumber plants and, after confirming oviposition thereon, the leaf discs were sprayed with solutions of the inventive compounds at a predetermined concentration prepared to 50% acetone/water (containing 0.05% Tween 20). After spraying, the treated leaf discs were held in an incubation chamber at 25° C. (16-hour period of light, 8-hour dark period). Fourteen days after spraying, the numbers of live and dead insects were counted, and the mortality was calculated from the following formula. This was a two-replication test.

Mortality (%)=[(number of oviposited eggs−number of live insects)/number of oviposited eggs]×100

From these results, with 100 ppm foliar application, Compounds 212, 229 and 230 exhibited high insecticidal activities having at least 80% mortality.

With foliar application at 20 ppm, Compound 213 exhibited a high insecticidal activity having at least 80% a mortality.

Test Example 10-1: Western Flower Thrips Control Test

Leaf discs 2.8 cm in diameter were cut from bean plants grown in pots, and these were sprayed with solutions of the inventive compounds at a predetermined concentration prepared to 50% acetone/water (containing 0.05% Tween 20). The treated leaf discs were air dried, following which first-instar larvae were released onto the discs. The leaf discs and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 500 ppm foliar application, Compounds 49, 50, 85, 86, 90, 91, 93, 94, 104, 107, 108, 114, 128, 131, 135, 137, 140, 141, 144, 145, 146, 147, 152, 167, 170, 171, 172, 176, 181, 182, 183, 184, 186, 189, 190, 193, 196, 199, 200, 208, 211, 212, 222, 226, 227, 229, 230, 231, 237, 240, 242 and 243 exhibited high insecticidal activities having at least 80% mortality. With 200 ppm foliar application, Compounds 1, 2, 3, 6, 7, 8, 9 and 10 exhibited high insecticidal activities having at least 80% mortality.

Test Example 10-2: Western Flower Thrips Control Test

Leaf discs 2.8 cm in diameter were cut from bean plants grown in pots, and these were sprayed with solutions of the inventive compounds at a predetermined concentration prepared to 50% acetone/water (containing 0.05% Tween 20). The treated leaf discs were air dried, following which first-instar larvae were released onto the discs. The leaf discs and larvae were then held in an incubation chamber at 25° C. (16-hour period of light, 8-hour dark period). Three days after released, the numbers of live and dead insects were counted, and the mortality was calculated from the following formula. This was a two-replication test.

Mortality (%)=[number of dead insects/(number of live insects+number of dead insects)]×100

From these results, with 100 ppm foliar application, Compounds 2, 3, 6, 7, 8, 9, 10, 90, 91, 104, 128, 137, 186, 193, 212, 213, 216 and 238 exhibited high insecticidal activities having at least 80% mortality.

Test Example 11: Rice Leaf Bug Control Test

Wheat seedling shoots four days after sowing were immersed for 30 seconds in solutions of the inventive compounds at a predetermined concentration prepared to 50% acetone/water (containing 0.05% Tween 20). The treated seedlings were air-dried, then each was placed in a glass cylinder and two second-instar rice leaf bug larvae were released within the same glass cylinder. Following release of the insects, the tube was capped and held in an incubation chamber at 25° C. (16-hour period of light, 8-hour dark period). In order to supply water to the wheat plant during the test, the plant was allowed to take up water from below the glass cylinder. Three days after released, the numbers of live and dead insects were counted, and the mortality was calculated from the following formula.

Mortality (%)=[number of dead insects/(number of live insects+number of dead insects)]×100

From these results, with 50 ppm foliar application, Compounds 132, 141, 144, 183, 184, 189, 190, 192, 193, 194, 212, 227, 229, 230, 231, 233, 236, 239, 242 and 243 exhibited high insecticidal activities having at least 80% mortality.

Test Example 12: Brown-Winged Green Bug Control Test

Young apples that had been collected in the field were sprayed with solutions of the inventive compounds at a predetermined concentration prepared to 50% acetone/water (containing 0.05% Tween 20). The treated fruits were air-dried, placed in plastic cups and two adult brown-winged green bugs were released into each cup. Following release of the insects, the fruits and insects were held in an incubation chamber at 25° C. (16-hour period of light, 8-hour dark period). Six days after released, the numbers of live and dead insects were counted, and the mortality was calculated from the following formula.

Mortality (%)=[number of dead insects/(number of live insects+number of dead insects)]×100

From these results, with 50 ppm foliar application, Compound 212 exhibited a high insecticidal activity having at least 80% mortality.

Test Example 13: Rice Leaf Beetle Control Test

The inventive compounds prepared to a predetermined concentration in acetone were locally applied in an amount of 1 μL (per insect) to the backs of field-collected adult beetles using a microsyringe. Following chemical treatment, the beetles were transferred to rice seedlings, with five beetles being placed on each plant, and the seedlings and beetles were held in an incubation chamber at 25° C. (16-hour period of light, 8-hour dark period). Forty-eight hours after treatment, the numbers of live and dead insects were counted, and the mortality was calculated from the following formula.

Mortality (%)=[number of dead insects/(number of live insects+number of dead insects)]×100

From these results, at a dosage of 0.5 μg/insect, Compounds 1, 8 and 212 exhibited high insecticidal activities having at least 80% mortality.

Test Example 14: House Fly Control Test

The inventive compounds prepared to a predetermined concentration in acetone were applied in an amount of 1 μL (per insect) to the backs of adult female flies raised indoors. Following chemical treatment, the flies were transferred to plastic cups, with five flies being placed in each cup, and held in an incubation chamber at 25° C. (16-hour period of light, 8-hour dark period). Twenty-four hours after treatment, the state of knockdown among the flies was observed, and the knockdown rate was calculated from the following formula. The test was carried out as two replications.

Knockdown rate (%)=[number of knocked down insects/(number of live insects+number of knocked down insects)]×100

From these results, at a dosage of 2 μg/insect, Compounds 33, 212, 213, 214 and 216 exhibited high insecticidal effects having a knockdown rate of at least 80%.

Root Immersion Treatment Test

Test Example 15: Small Brown Planthopper Control Test

Wheat seedling roots 48 hours after sowing were treated with solutions of the inventive compounds at a predetermined concentration prepared to 10% acetone/water. After allowing the roots to absorb the chemical for 72 hours, ten second-instar small brown planthopper larvae were released onto each seedling. The treated seedlings and larvae were then held in an incubation chamber at 25° C. (16-hour period of light, 8-hour dark period). Four days after released, the numbers of live and dead insects were counted, and the mortality was calculated from the following formula. The test was carried out as two replications.

Mortality (%)=[number of dead insects/(number of live insects+number of dead insects)]×100

From these results, at a dosage of 20 μg/seedling, Compounds 212, 213, 215, 216, 222, 223, 226, 227, 228, 230, 231, 233, 234, 235, 237, 212, 213, 214, 215, 216, 222, 223, 227, 228, 229, 231, 233, 234, 235, 237, 238, 239, 240 and 241 exhibited high insecticidal activities having at least 80% mortality.

Soil Drenching Treatment Tests

Test Example 16: Small Brown Planthopper Control Test

Rice seedlings grown in pots were subjected to soil drenching treatment with solutions of the inventive compounds at a predetermined concentration prepared to 10% acetone/water. Three days following treatment, ten second-instar small brown planthopper larvae were released onto each seedling. The treated seedlings and larvae were then held in an incubation chamber at 25° C. (16-hour period of light, 8-hour dark period). Three days after released, the numbers of live and dead insects were counted, and the mortality was calculated from the following formula. The test was carried out as two replications.

Mortality (%)=[number of dead insects/(number of live insects+number of dead insects)]×100

From these results, at a dosage of 0.05 mg/seedling, Compounds 212, 227, 229, 231, 233, 237, 238, 239, 242 and 243 exhibited high insecticidal activities having at least 80% mortality, and at a dosage of 0.005 mg/seedling, Compound 212 exhibited a high insecticidal activity having 95% mortality.

Test Example 17: White-Backed Rice Planthopper Control Test

Rice seedlings grown in pots were subjected to soil drenching treatment with solutions of the inventive compounds at a predetermined concentration prepared to 10% acetone/water. Three days following treatment, ten second-instar white-backed rice planthopper larvae were released onto each seedling. The treated seedlings and larvae were then held in an incubation chamber at 25° C. (16-hour period of light, 8-hour dark period). Three days after released, the numbers of live and dead insects were counted, and the mortality was calculated from the following formula. The test was carried out as two replications.

Mortality (%)=[number of dead insects/(number of live insects+number of dead insects)]×100

From these results, at a dosage of 0.05 mg/seedling, Compounds 212, 227, 229 and 231 exhibited high insecticidal activities having at least 80% mortality.

Test Example 18: Rice Water Weevil Control Test

Rice seedlings grown in pots were subjected to soil drenching treatment with solutions of the inventive compounds at a predetermined concentration prepared to 10% acetone/water. Two days after treatment, five adult rice water weevils were released onto each seedling. The seedlings and insects were then held in an incubation chamber at 25° C. (16-hour period of light, 8-hour dark period). Three days after released, the numbers of live and dead insects were counted, and the mortality was calculated from the following formula. The test was carried out as two replications.

Mortality (%)=[number of dead insects/(number of live insects+number of dead insects)]×100

From these results, at a dosage of 0.1 mg/seedling, Compound 212 exhibited a high insecticidal activity having at least 80% mortality.

Effects on Pests Having a Low Susceptibility to Insecticides

Test Example 19: Brown Rice Planthopper Control Test

Rice seedlings grown in pots were subjected to soil drenching treatment with solutions of the inventive compounds at a predetermined concentration prepared to 10% acetone/water. Three days after treatment, ten second-instar brown rice planthopper larvae having a low susceptibility to insecticides were released onto each seedling. The seedlings and insects were then held in an incubation chamber at 25° C. (16-hour period of light, 8-hour dark period). Three days after released, the numbers of live and dead insects were counted, and the mortality was calculated from the following formula. The test was carried out as two replications.

Mortality (%)=[number of dead insects/(number of live insects+number of dead insects)]×100

The pests used in this test were insects that had been raised indoors for successive generations over a long period of time (susceptible line), and insects that had been raised indoors for successive generations after being collected (I) in 2007 within Kumamoto Prefecture and (II) in 2005 within Fukuoka Prefecture (field-collected lines).

As a result, Compound 212 exhibited a mortality of 100% on all the lines in treatment at a dosage of 0.05 mg/seedling, and exhibited a mortality of at least 90% on all the lines at a dosage of 0.005 mg/seedling. By contrast, when applied at a dosage of 0.05 mg/seedling, imidacloprid exhibited a mortality of 100% in the susceptible line and mortalities of 40% on (I) and 60% on (II).

From these results, Compound 212 exhibited a high insecticidal activity against brown rice planthoppers having a low susceptibility to imidacloprid.

Test Example 20: Small Brown Planthopper Control Test

Rice seedlings grown in pots were subjected to soil drenching treatment with solutions of the inventive compounds at a predetermined concentration prepared to 10% acetone/water. Three days after treatment, ten second-instar small brown planthopper larvae having a low susceptibility to insecticides were released onto each seedling. The seedlings and insects were then held in an incubation chamber at 25° C. (16-hour period of light, 8-hour dark period). Three days after released, the numbers of live and dead insects were counted, and the mortality was calculated from the following formula. The test was carried out as two replications.

Mortality (%)=[number of dead insects/(number of live insects+number of dead insects)]×100

The pests used in this test were insects that had been raised indoors for successive generations over a long period of time (susceptible line), and insects that had been raised indoors for successive generations after being collected in 2006 within Kumamoto Prefecture (field-collected line).

As a result, Compound 212 exhibited a mortality of 100% on both lines at a dosage of 0.01 mg/seedling, and exhibited a mortality of at least 90% on both lines at a dosage of 0.005 mg/seedling. By contrast, when applied at a dosage of 0.01 mg/seedling, imidacloprid exhibited a mortality of 100% in the susceptible line and a mortality of 50% in the field-collected line. When applied at a dosage of 0.01 mg/seedling, fipronil exhibited a mortality of 100% in the susceptible line and a mortality of 70% in the field-collected line.

From these results, Compound 212 exhibited a high insecticidal activity against small brown planthoppers having a low susceptibility to imidacloprid and fipronil.

Test Example 21: In Vitro Metabolic Tests of Compound 212 and Imidacloprid Using House Fly Crude Enzyme Extract As mentioned in Pest Management Science, 59(3), 347-352 (2003) and the Journal of Pesticide Science, 29(2), 110-116 (2004), imidacloprid is known to be inactivated by incurring oxidative metabolism, which is thought to be one mechanism of acquiring resistance to this agent. The following experiment was carried out to confirm the effects in pests which have acquired such resistance.

An amount of 10 mL of a potassium phosphate buffer solution (pH 7.4, containing 1 mM EDTA) was added to adult house flies (0.645 g), and the flies were thoroughly homogenized in a Physcotron (Niti-On Medical and Physical Instruments Manufacturing Co.). The homogenate was then centrifuged at 10,000 g for 15 minutes. The resulting supernatant was additionally centrifuged at 100,000 g for 60 minutes, giving a precipitate. The precipitate was dissolved in 1 mL of a potassium phosphate buffer, and the resulting solution was used as the crude enzyme extract. The enzyme extraction operations were all carried out on ice or at 4° C.

The reagents were mixed in the following proportions within a 1.5 mL tube, and the reaction was effected at 25° C. for 40 hours. Following the reaction, 1 mL of acetone was added and the mixture was stirred, following which the precipitate that formed was centrifuged at 12,000 rpm for 5 minutes. The supernatant acetone was distilled off, and the precipitate was injected into a liquid chromatograph-mass spectrometer (LC/MS) and analysis was carried out.

Above crude enzyme extract: 300 µL
DMSO solution of compound: 5 µL
Glucose 6 phosphoric acid solution: 5 µL
NADP$^+$ solution: 5 µL
Glucose 6 phosphoric acid dehydrogenase solution: 5 µL
Potassium phosphate buffer (pH 7.4, containing 1 mM EDTA): 180 µL <Analysis Conditions>
Column: Capcell Pak C18MG
Mobile Phase Composition:
0 to 3 minutes: 85% water, 5% acetonitrile, 10% aqueous formic acid solution (0.1% v/v)
3 to 30 minutes: 85→25% water, 5→65% acetonitrile, 10% aqueous formic acid solution (0.1% v/v)
30.1 to 36 minutes: 90% acetonitrile, 10% aqueous formic acid solution (0.1% v/v)
Column temperature: 40° C.
Flow rate: 0.35 mL/min
Injected amount: 100 µL
UV wavelength: Compound 212: 325 nm
Imidacloprid: 300 nm As a result, the sum of the surface area percentages for the metabolites was 0.08% in the case of Compound No. 212 and 2.55% in the case of imidacloprid, indicating that the amount of metabolites of Compound No. 212 was lower than the amount of metabolites of imidacloprid. The above results suggest that Compound 212 can effectively control even resistant pests which metabolically deactivate imidacloprid.

Control Effects on Animal Parasitic Pests

Test Example 21: Tick (*Haemaphysalis longicornis*) Control Test

Glass vials having a capacity of 4 mL were each filled with 30 µL of an acetone solution containing 200 ppm or 10 ppm of the respective compounds. These filled vials were placed on a shaker and air-dried while being spun, thereby forming dry films of the compounds on the inner walls of the vials. After the vials had been dried for at least 24 hours, ten larval ticks (*Haemaphysalis longicornis*) were released into each vial, following which the vials were capped. The vials were then left at rest in an incubation chamber at 25° C., 85% humidity and complete darkness. One day after released, the numbers of live and dead ticks were counted, and the mortality was calculated from the following formula. This test was carried out as two replications.

Mortality (%)=[number of dead ticks/(number of live ticks+number of dead ticks)]×100

As a result, at a dosage of 200 ppm, Compounds 1, 2, 3, 6, 7, 8, 9, 10, 11, 15, 18, 19, 20, 21, 39, 41, 42, 43, 45, 49, 50, 53, 58, 61, 72, 86, 88, 89, 91, 92, 93, 94, 96, 97, 101, 102, 105, 107, 108, 109, 111, 112, 114, 115, 119, 120, 130, 131, 132, 135, 137, 138, 165, 196, 199, 200, 204, 212, 213 and 214 exhibited tickcidal effects having at least 80% mortality.

At a dosage of 10 ppm, Compounds 1, 2, 3, 6, 7, 8, 9, 10, 18, 19, 42, 43, 58, 88, 91, 93, 94, 165, 196, 208, 212, 213 and 214 exhibited tickcidal effects having at least 80% mortality.

In similar tests, the mortality from treatment with 10 ppm of imidacloprid was 4%.

Test Example 22: Tick (*Haemaphysalis longicornis*) Control Test on Body Surface of Mouse Ventral fur was shaved from an area having a diameter of about 2 cm in mice (ICR, 5-week-old males), and a 15 mL polystyrene conical tube cut to a length of about 1.5 cm was attached to the shaved area using instant glue.

An amount of 20 μL of a 1,000-fold dilution of the pest control agent prepared in the same way as in Formulation Example 11 was added dropwise onto the body surface of the mice within the attached tube. After the solution was allowed to dry thoroughly, ten or more larval ticks (*Haemaphysalis longicornis*) were released into the tube, which was then capped. Three days after released, the numbers of live and dead ticks were counted, and the mortality was calculated from the following formula.

Blood-feeding inhibition (%)=100−[number of feeding ticks/(number of live ticks+number of dead ticks)]×100

As a result, Compound 212 below exhibited a blood-feeding inhibition of 91%.

Test Example 23: Effects on Canine Heartworm

The activities of the compounds were evaluated based on changes in the motility of microfilariae in canine heartworm. The respective compounds were dissolved in a RPMI1640 liquid culture medium to a concentration of 3.13 ppm, following which about 20 canine heartworm microfilariae were placed in each culture fluid and cultured at 37° C. The motility of the canine heartworm microfilariae was observed for 48 hours following the start of culturing, and the activities of the compounds were rated according to the following criteria.

Criteria A: At least two-thirds of the heartworms died
B: Substantially all the heartworms were affected in some way, or at least one-third died
C: No influence, or less than one-third of the heartworms died As a result, at a dosage of 3.13 ppm, Compounds 1, 2, 6, 7, 8, 9 and 10 had a microfilaricidal effect at or higher than level B.

The microfilaricidal effects of Compound Nos. 212, 227, 229, 231, 237, 238, 239, 242 and 243, which are especially preferred compounds according to the invention, are summarized in Table 12.

TABLE 12

| | Insecticidal effects (mortality) in various pests | | | | | | | | | | | | | | | | | |
|---|---|---|---|---|---|---|---|---|---|---|---|---|---|---|---|---|---|---|
| | Diamondback moth | | | Common cutworm | | Cotton aphid | | | | | Western flower thrips | | | Small brown planthopper second-instar larvae | | | | |
| | second-instar larvae | | | third-instar larvae | | first-instar larvae | | | | | first-instar larvae | | | Foliar application (ppm) | | | Soil drenching treatment (mg/pot) | |
| Compound | | | | | | Foliar application (ppm) | | | | | | | | | | | | |
| No. | 500 | 100 | 20 | 500 | 100 | 500 | 100 | 20 | 5 | 1.25 | 500 | 100 | 20 | 100 | 5 | 1.25 | 0.313 | 0.05 | 0.01 |
| 212 | 100 | 100 | 100 | 100 | 30 | 100 | 100 | 100 | 95 | 100 | 100 | 100 | 65 | | 100 | 100 | 75 | 100 | 100 |
| 227 | 100 | 100 | 100 | 100 | 56 | 100 | 100 | 100 | 100 | 95 | 90 | 65 | | | 100 | | | 90 | 100 |
| 229 | 100 | 100 | 40 | 100 | 30 | 100 | 100 | 100 | 95 | 80 | 100 | 60 | | | 95 | | | 100 | 100 |
| 231 | | 100 | 100 | 0 | 0 | | | 100 | 100 | 74 | 85 | 55 | | 100 | | | | 100 | 100 |
| 237 | 100 | 100 | 100 | 33 | | 100 | 100 | 85 | | | 90 | | | | | | | 100 | 75 |
| 238 | | 100 | 60 | 0 | | | 100 | 100 | 100 | 100 | | 95 | | | | | | 100 | 100 |
| 239 | 100 | 100 | 100 | 90 | | 100 | 100 | 100 | | | 40 | | | | | | | 100 | 80 |
| 242 | 100 | 100 | | 60 | | | 100 | 100 | 80 | 35 | 100 | 76 | | | | | | 100 | |
| 243 | 100 | 100 | | 10 | | 100 | 100 | | 80 | 100 | 100 | | | | | | | 100 | |

| | Insecticidal effects (mortality) in various pests | | | | | | | | | | | | | | |
|---|---|---|---|---|---|---|---|---|---|---|---|---|---|---|---|---|
| | Soil drenching treatment (mg/pot) | | Wheat root immersion treatment (mg/seedling) | | | | | | | | Brown rice planthopper second-instar larvae Soil drenching treatment (mg/pot) | | Rice leaf bug, second-instar larvae 3 or 4 DAA | | | Adult house flies Dosage mg/fly |
| Compound | | | | | | | | | | | | | | | | |
| No. | 0.005 | 0.002 | 20 | 2 | 0.5 | 0.25 | 0.125 | 0.063 | 0.031 | 0.016 | 0.0078 | 0.05 | 0.02 | 50 | 10 | 2 | 2 |
| 212 | 95 | 85 | 100 | 100 | 100 | 100 | 100 | 100 | 100 | 50 | 50 | 100 | 100 | 100 | 100 | 100 | 100 |
| 227 | 75 | | | 100 | 75 | 50 | | | | | | | | 100 | 100 | 83 | |

TABLE 12-continued

| 229 | 30 |     | 100 | 100 | 75  |     | 25 | 100 | 100 | 100 |
|-----|----|-----|-----|-----|-----|-----|----|-----|-----|-----|
| 231 | 70 | 100 | 75  | 25  |     |     |    | 100 |     |     |
| 237 |    | 100 | 100 | 50  |     |     |    |     | 67  |     |
| 238 | 33 | 100 | 100 | 100 |     | 25  |    | 100 |     |     |
| 239 | 30 | 100 | 100 | 100 | 100 |     |    | 100 |     |     |
| 242 |    |     | 100 | 100 | 100 |     |    | 100 |     |     |
| 243 |    |     | 100 | 100 | 100 |     |    | 100 |     |     |

In addition, the effects against pests having a low susceptibility to insecticides by Compound Nos. 212, 227, 229, 231, 237, 238, 239, 242 and 243, which are especially preferred compounds according to the invention, are summarized in Table 13.

TABLE 13

|  | Small brown planthopper (rice soil drenching) | | | | Brown rice planthopper, Kumamoto low susceptibility (rice soil drenching) | |
|---|---|---|---|---|---|---|
|  | 0.05 mg/pot | 0.01 mg/pot | 0.005 mg/pot | 0.002 mg/pot | 0.05 mg/pot | 0.005 mg/pot |
| 212 | 100 | 100 | 95 | 85 | 100 | 90 |
| 227 | 90 | 100 | 75 |  |  |  |
| 229 | 100 | 100 | 30 |  |  |  |
| 231 | 100 | 100 | 70 |  |  |  |
| 237 | 100 | 75 |  |  |  |  |
| 238 | 100 | 100 | 33 |  |  |  |
| 239 | 100 | 80 | 30 |  |  |  |
| 242 | 100 |  |  |  |  |  |
| 243 | 100 |  |  |  |  |  |
| Comparative Example 2 (Patent Document 6, Compound 20) | 20 |  |  |  |  |  |
| Comparative Example 3 (Patent Document 4, Compound 2) | 10 |  |  |  |  |  |
| Comparative Example 4 (Patent Document 5, Example 4) | 100 | 20 |  |  | 45 |  |
| Comparative Example 5 (Patent Document 5, Example 3) | 95 | 15 |  |  | 25 |  |
| Comparative Example 6 (Patent Document 5, Example 5) | 100 | 20 |  |  | 25 |  |
| Comparative Example 7 (Patent Document 5, Example 7) | 63 | 5 |  |  | 20 |  |
| Comparative Example 8 (Patent Document 5, Example 6) | 20 |  |  |  |  |  |

INDUSTRIAL APPLICABILITY

The amine derivatives of the present invention have excellent insecticidal effects against the diamondback moth, the common cutworm, the cotton aphid, the small brown planthopper, the brown rice planthopper, the green rice leafhopper, the hard-bodied tick Haemaphysalis longicornis, and many other pests. Also, they are able to exhibit strong effects even against insects having a low insecticide susceptibility, particularly delphacid planthoppers. Moreover, they are effective also in treating soil and plant cultivation media and, because they are able to mitigate the chances of worker exposure to chemicals, can be safely used to control pests. Therefore, the present invention is capable of being highly beneficial in the field of pest control.

The invention claimed is:

1. A method for controlling agricultural/horticultural pests, comprising the step of treating a subject in need of treatment with an effective amount of an amine derivative or a salt thereof or with a composition comprising an effective amount of the amine derivative or salt thereof and at least one of a carrier and an adjuvant, wherein the amine derivative is N-[1-((6-chloropyridin-3-yl)methyl)pyridine-2(1H)-ylidene]-2,2,2-trifluoroacetamide, wherein the agricultural/horticultural pest is at least one selected from the group consisting of cabbage armyworm, armyworm, cabbage butterfly caterpillar, beet armyworm, rice stem borer, grass leaf roller, rice green caterpillar, leaf roller moth, leaf miner moth, oriental tussock moth, pests belonging to the genus Agrotis, pests belonging to the genus Heliothis, Aphis fabae, corn leaf aphid, pea aphid, foxglove aphid, Aphis craccivora, Macrosiphum euphorbiae, Macrosiphum avenae, Methopolophium dirhodum, Schizaphis graminum, cabbage aphid, turnip aphid, spiraea aphid, rosy apple aphid, woolly apple aphid, Toxoptera aurantii, brown citrus aphid, silverleaf whitefly, sweet potato whitefly, citrus mealybug, white peach scale, California red scale, yellow mealworm, cupreous chafer, soy bean beetle, codling moth larvae, longicorn beetles, two-spotted spider mite, Kanzawa spider mite, Panonychus citri, sawflies, grasshoppers, locusts, leaf miner flies, melon thrips, root knot nematode, root lesion nematode, rice white-tip nematode, and pine wood nematode.

* * * * *